(12) United States Patent
Mueller-Wolf

(10) Patent No.: US 10,692,589 B2
(45) Date of Patent: Jun. 23, 2020

(54) "INDIMA APPARATUS" SYSTEM, METHOD AND COMPUTER PROGRAM PRODUCT FOR INDIVIDUALIZED AND COLLABORATIVE HEALTH CARE

(71) Applicant: Martin Mueller-Wolf, Zug (CH)

(72) Inventor: Martin Mueller-Wolf, Zug (CH)

(*) Notice: Subject to any disclaimer, the term of this patent is extended or adjusted under 35 U.S.C. 154(b) by 863 days.

(21) Appl. No.: 14/373,575

(22) PCT Filed: Jan. 20, 2013

(86) PCT No.: PCT/IB2013/000183
§ 371 (c)(1),
(2) Date: Jul. 21, 2014

(87) PCT Pub. No.: WO2013/108122
PCT Pub. Date: Jul. 25, 2013

(65) Prior Publication Data
US 2015/0025903 A1    Jan. 22, 2015

Related U.S. Application Data

(60) Provisional application No. 61/588,721, filed on Jan. 20, 2012, provisional application No. 61/752,887, filed on Jan. 15, 2013.

(51) Int. Cl.
*G16H 10/20* (2018.01)
*G16H 80/00* (2018.01)
(Continued)

(52) U.S. Cl.
CPC ............ *G16H 10/20* (2018.01); *G16H 10/60* (2018.01); *G16H 50/20* (2018.01); *G16H 80/00* (2018.01)

(58) Field of Classification Search
USPC ........................................................ 705/2–4
See application file for complete search history.

(56) References Cited

U.S. PATENT DOCUMENTS 5,851,186 A    12/1998 Wood et al.
5,915,036 A *  6/1999 Grunkin ................ G06T 7/0012
                                                          382/132
(Continued)

FOREIGN PATENT DOCUMENTS

DE    3929077       1/1997
EP    1351181 A1   10/2003

OTHER PUBLICATIONS

Reuter, M. et al. ((2004). Computing with activities II: ruling robots by the activity patterns of hierarchical sums. 441-446. 10.1109/WAC.2004.185447).*

(Continued)

*Primary Examiner* — Mark Holcomb
(74) *Attorney, Agent, or Firm* — David Guerra

(57) ABSTRACT

A system and method for 'Individualized Life Management' focusing on individualized and collaborative health care involving a plurality of individuals, using groups of state parameters for defining a state of each individual, and using groups of action parameters for defining 'treatment options' and/or 'behavior options' targeted at an individual. The system includes a data processor for processing input data, based on the groups of state parameters, into output data, which are the basis for the groups of action parameters, using defined relationships/assignments between groups of state parameters and groups of action parameters. Data storage stores the groups of state parameters and action parameters and the defined relationships/assignments between groups of the state and action parameters. A data communication system/platform communicates state parameters and/or action parameters among the individuals. The data processor means can include an adaptive structure (e.g., neural networks) where the defined relationships/assignments between groups are redefined/updated using empirical pairs of action parameter groups and state parameter groups.

38 Claims, 53 Drawing Sheets

(51) Int. Cl.
*G16H 10/60* (2018.01)
*G16H 50/20* (2018.01)

(56) References Cited

U.S. PATENT DOCUMENTS

| | | | | |
|---|---|---|---|---|
| 6,725,163 | B1 * | 4/2004 | Trappe | G01V 1/28 |
| | | | | 702/14 |
| 8,069,055 | B2 | 11/2011 | Keen | |
| 2004/0122704 | A1 * | 6/2004 | Sabol | G06F 19/321 |
| | | | | 705/2 |
| 2004/0215489 | A1 * | 10/2004 | Abraham-Fuchs | G06F 19/326 |
| | | | | 705/2 |
| 2007/0185391 | A1 * | 8/2007 | Morgan | A61B 5/0002 |
| | | | | 600/301 |
| 2010/0313157 | A1 * | 12/2010 | Carlsson | G06F 16/287 |
| | | | | 715/769 |
| 2013/0080184 | A1 * | 3/2013 | Streat | G06Q 50/24 |
| | | | | 705/2 |

OTHER PUBLICATIONS

Halpern, Michael T., et al. "Health and economic outcomes modeling practices: a suggested framework." Value in Health 1.2 (1998) : 131-147.*

* cited by examiner

SIX KEY BENEFITS (InDiMa 4S CCS)
InDiMa 4 Step Collaborative Care System

1. Easy to Use
   Self-Explaining System: Information ⇔ Questions ⇔ Report ⇔ Follow-up Options & Actions 2. Complete 'Systemic Approach'
   (Bio-Medical- + Psycho- + Perso- + Socio-„(BPPS-)Marker")

3. Action-Oriented & Solution-Oriented ⇔ 'Need for Action' is indicated:
   ■ = 'Urgent Need for Action'  ■ = 'Definite Need for Action'  ■ = 'Optimize' (Improve)  ■ = 'Okay' (Continue)

4. Efficiently Supporting the Patient and the Doctor:
   Health Care Visit Preparation, Results, Documentation (and Progress by 'Predictive Models')

5. Full Picture through '360° View Report' with Self-Assessment and Assessment by Medical Team, Family and Diabetes-Group

6. Outcome Improvement and Cost Reduction through 'Individualized Collaborative Care':

6.1 Categorization of 3 Stages: Efficiency Increase through 'Stage-Oriented' Diabetes Management
   Stage1: Empowerment & Enabling, Stage2: Cooperation & Control, Stage3: Coping & Adaptation of Lifestyle 6.2 Outcome Improvement through Person-Centered '4 Steps Collaborative Care':
   (1) 'Analyzer'   (2) 'Supporter'   (3) 'Engager'   (4) 'Realizer'
       Analysis  ⇔  Support       ⇔  Engagement ⇔  Results /Realization

FIG. 6

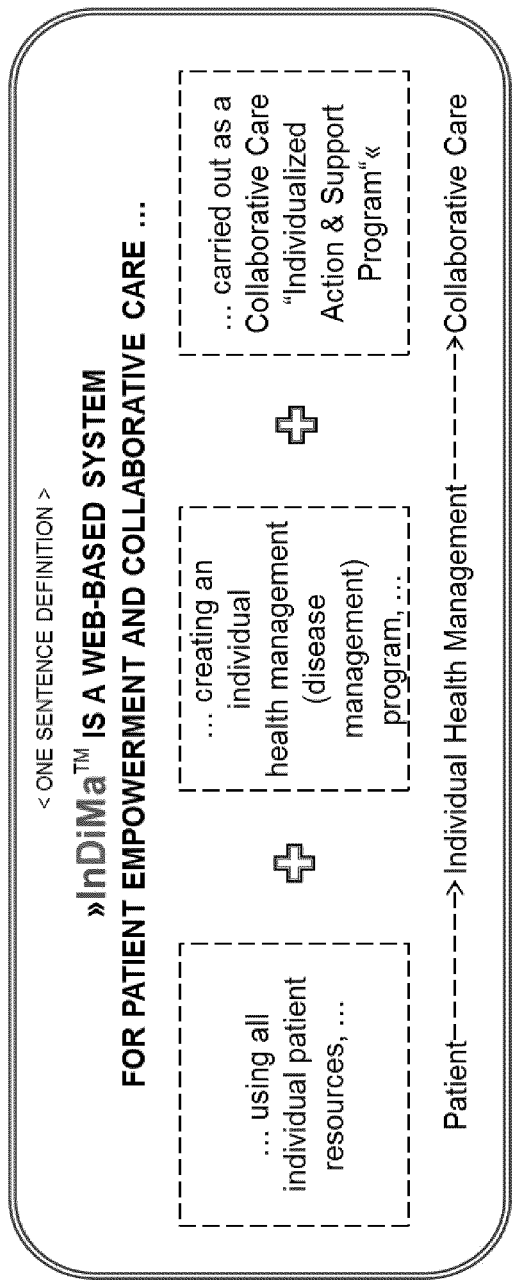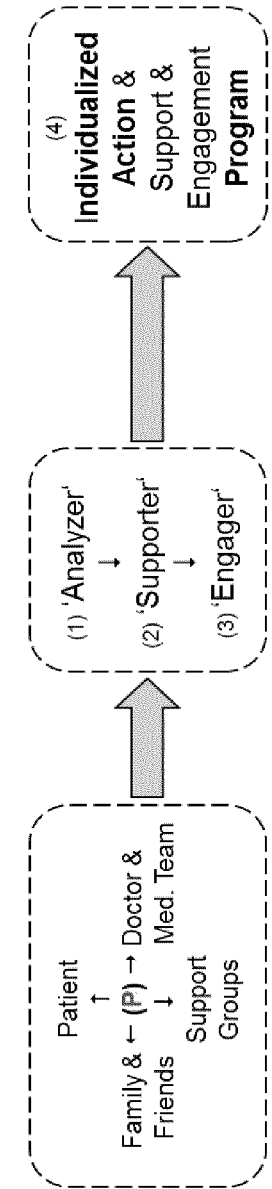
FIG. 8

PARADIGM SHIFT IN INDIVIDUALIZED AND COLLABORATIVE HEALTH AND DISEASE MANAGEMENT

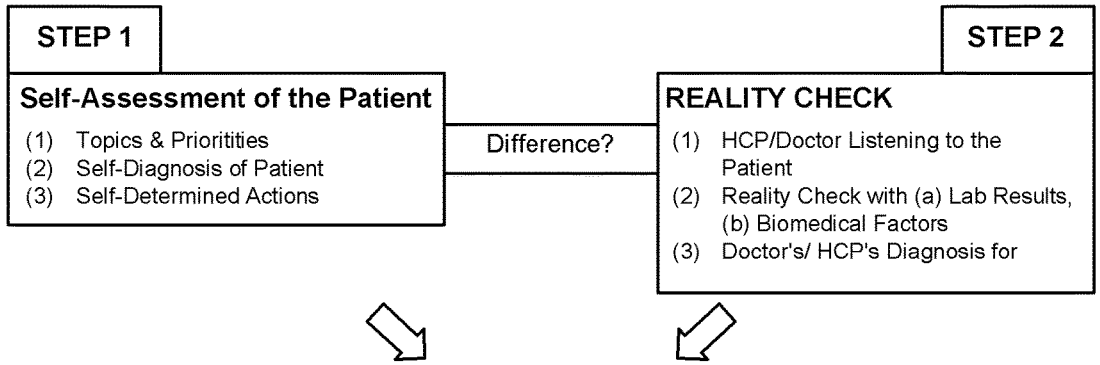

STEP 1

Self-Assessment of the Patient
(1) Topics & Priorities
(2) Self-Diagnosis of Patient
(3) Self-Determined Actions Difference?

STEP 2

REALITY CHECK
(1) HCP/Doctor Listening to the Patient
(2) Reality Check with (a) Lab Results, (b) Biomedical Factors
(3) Doctor's/ HCP's Diagnosis for

STEP 3A: "Reality Deviance" as Predictor
Resuliting from Step 1 and 2, the difference between self-assessment (subjective reality) and biomedical facts / HCP's diagnosis (reality check) is determined.

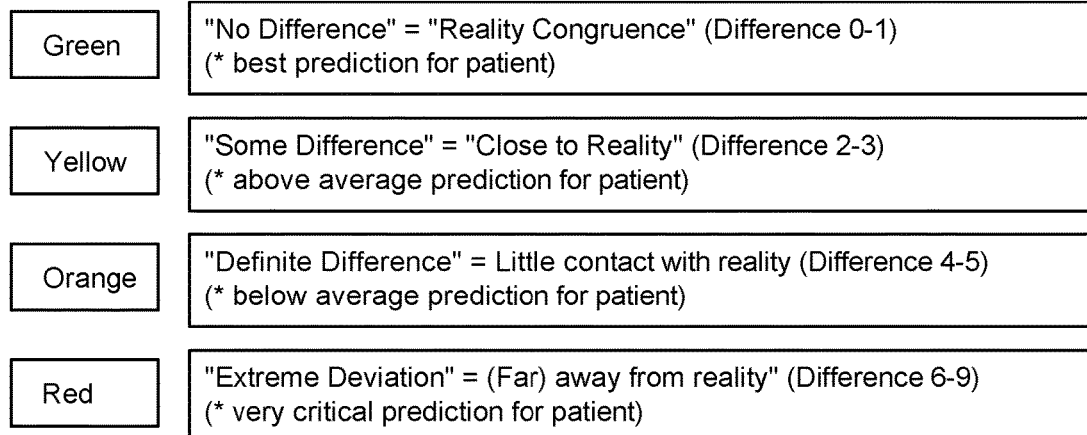

| Green | "No Difference" = "Reality Congruence" (Difference 0-1) (* best prediction for patient) |
| Yellow | "Some Difference" = "Close to Reality" (Difference 2-3) (* above average prediction for patient) |
| Orange | "Definite Difference" = Little contact with reality (Difference 4-5) (* below average prediction for patient) |
| Red | "Extreme Deviation" = (Far) away from reality" (Difference 6-9) (* very critical prediction for patient) |

STEP 3B: Based upon "Reality Deviance" as Predictor: Pateint Action Program
The biomedical facts are explained and the HCP's diagnosis (reality check) is discussed with teh patient in order to come to a Collaborative Care Action Program - the "Patient-Doctor Agreement".

*) Definition: "Health" is successful coping with reality of life.

FIG. 12 http://www.indimasurvey.com/portfolio/InDiMaDRMType2_0GUIDE_Patient/index.asp?step=1

InDiMa
Individualized Diabetes Management

Welcome

On this page you will find a questionnaire that your doctor composed especially for you.

You are free to leave any questions blank that you do not wish to answer.
In that case please use the "NA" = "No Answer" possibility next to the scales.

After finishing the questionnaire, your report will appear. This report is only for you to open. You can decide which elements of this report will be used for the final report to be sent to your doctor as preparation for your next health care visit.

If you want to have a break ("Pause"), you can go to the end of this page and click on "Pause, finish the survey later another time".

You can finish the survey later on. Therefore, you need to log in again with your password.

To enlarge the following questions for better reading, use the zoom function of yoru tablet. Touch the surface with two fingers and spread them apart. To resize the zoom function, close your fingers again.

Answering the 10 'InDiMa Guide' questions, you are reflecting your health, fitness, the success of your diabetes management, the three medical key criteria, and your quality of life:

Please, use the scale from "1" to "4":

| 1 | okay - good (continue and maintain ++ secure sustainability) |
| 2 | improve (think it over and improve ?! - partner or group - support? act!) |
| 3 | must change (don't wait - act now!! - see doctor! action program) |
| 4 | urgent action (danger? urgency program !!! - must see doctor now!) |

(if you do not want to answer any question, please mark " NA" = "No Answer ".)

1 = okay - good  [2] = improve  [3] = must change  [4] = urgen action

| | 1 | 2 | 3 | 4 | N/A |
|---|---|---|---|---|---|
| 1  My overall physical and psychological health: | ● | ○ | ○ | ○ | ○ |

1 = okay - good  [2] = improve  [3] = must change  [4] = urgen action

| | 1 | 2 | 3 | 4 | N/A |
|---|---|---|---|---|---|
| 2  Positive energy and motivation for ocping with diabetes (vs. lack of energy, depression tendencies, and burn out: | ● | ○ | ○ | ○ | ○ |
| 3  My blood pressure and fitness (healthy eating and weight control): | ○ | ● | ○ | ○ | ○ |
| 4  My cholesterol, lipids and cardiovascular status (physical activity and no smoking): | ○ | ● | ○ | ○ | ○ |
| 5  My blood glucose control (HbA1c long-term value; avoiding glucose 'hypos' and 'hypers'): | ● | ○ | ○ | ○ | ○ |

Pause, finish survey another time        Next

FIG. 16

FIG. 16 - Continued http://www.indimasurvey.com/portfolio/DRMType2_0GUIDE_Doctor/index.asp?step=1

InDiMa
Individualized Diabetes Management

Welcome

On this page you will find a questionnaire that your doctor composed especially for you.

You are free to leave any questions blank that you do not wish to answer.
In that case please use the "NA" = "No Answer" possbility next to the scales.

After finishing the questionnaire, your report will appear. This report is only for you to open. You can decide which elements of this report will be used for the final report to be sent to your doctor as preparation for your next health care visit.

If you want to have a break ("Pause"), you can go to the end of this page and click on "Pause, finish the survey later another time".

You can finish the survey later on. Therefore, you need to log in again with your password.

*mouse wheel* and *scroll up and down* to adjust the size of the print for your neds.

Note for Tablet:
To *enlarge* the following questions for better reading, use the zoom function of your table. Touch the surface with *two fingers* and *spread them apart*. To *resize* the screen, *close* your *fingers* again.

Please, asses the health, fitness, success of diabetes management, the three medical key criteria, and the quality of life of your patient:

Please, use the scale from "1" to "4":

| 1 | okay - good (continue and maintain ++ - secure sustainability) |
| 2 | improve (think it over and improve ?! - partner or group - support? act!) |
| 3 | must change (don't wait - act now!! - see doctor! action program) |
| 4 | urgent action (danger? urgency program !!! - must see doctor now!) |

*(if you do not want to answer any question, please mark " NA " = "No Answer".)*

1 = okay - good   2 = improve   3 = must change   4 = urgen action

|   |   | 1 | 2 | 3 | 4 | N/A |
|---|---|---|---|---|---|---|
| 1 | Overall physical and psychological health: | ○ | ● | ○ | ○ | ○ |
| 2 | Positive energy and motivation for ocping with diabetes (vs. lack of energy, depression tendencies, and burn out: | ○ | ● | ○ | ○ | ○ |
| 3 | Blood pressure and fitness (healthy eating and weight control): | ○ | ○ | ● | ○ | ○ |
| 4 | Cholesterol, lipids and cardiovascular status (physical activity and no smoking): | ○ | ● | ○ | ○ | ○ |
| 5 | Blood glucose control (HbA1c long-term value; avoiding glucose 'Hypos' and 'Hypers')": | ○ | ● | ○ | ○ | ○ |

Pause, finish survey another time

Next

FIG. 17

FIG. 17 - Continued http://www.indimasurvey.com/portfolio/DRMType2_0GUIDE_Doctor/index.asp?step=1#/?p=2

InDiMa
Individualized Diabetes Management

Welcome

No text defined [HEADER_STEP1]

Page 2 of 5

| 1 | = good - okay | 2 | = need more | 3 | = definitely needed | 4 | = urgently needed |

| | | 1 | 2 | 3 | 4 | N/A |
|---|---|---|---|---|---|---|
| 6 | The support for a healthy lifestyle with my diabetes in my social environment (healthy eating, physical activity, no smoking): | ○ | ○ | ● | ○ | ○ |
| 7 | Acceptance of guidance and support by my doctor, and cooperation with my medical teacm and readiness to act consequently: | ○ | ○ | ● | ○ | ○ |

[ Next ]

Pause, finish survey another time

--- http://www.indimasurvey.com/portfolio/DRMType2_0GUIDE_Doctor/index.asp?step=1#/?p=3

InDiMa
Individualized Diabetes Management

Welcome

No text defined [HEADER_STEP1]

Page 3 of 5

| 1 | = normal weight | 2 | = some overweight | 3 | = definte overweight | 4 | = obesity (adiposity) |

| | | 1 | 2 | 3 | 4 | N/A |
|---|---|---|---|---|---|---|
| 8 | Eating behavior (weight control, healthy eating, and physical activity) | ○ | ○ | ● | ○ | ○ |

[ Next ]

Pause, finish survey another time

--- http://www.indimasurvey.com/portfolio/DRMType2_0GUIDE_Doctor/index.asp?step=1#/?p=4

InDiMa
Individualized Diabetes Management

Welcome

No text defined [HEADER_STEP1]

Page 3 of 5

| 1 | = normal weight | 2 | = some overweight | 3 | = definte overweight | 4 | = obesity (adiposity) |

| | | 1 | 2 | 3 | 4 | N/A |
|---|---|---|---|---|---|---|
| 9 | Knowledge about self-care, my therapy adherence and quality of self-care: | ○ | ○ | ● | ○ | ○ |
| 10 | Coping with diabetes, adaptation of lifestyle with physical activity and quality of life in total: | ○ | ● | ○ | ○ | ○ |

[ Next ]

Pause, finish survey another time

InDiMa DRM TYPE 2_0 GUIDE_PATIENT

| Code number: | 754-365-128-001 | Name: | Barnie Miller | Date: | January 18, 2013 |

*Legend:*

| "4" = red: urgent action | "3" = orange: must change | "2" = yellow: improve | "1" = green: okay - good |
|---|---|---|---|

InDiMa GUIDE (DIABETES TYPE 2)
Patient's Self-Assessment (and 'Reality Check' by Doctor): Collaborative Care 1. My overall physical and psychological health:
   - Self-rating: is (very) good (☺ ☺ ☺ MAINTAIN IT; PROVIDE SUSTAINABILITY ☺)
   - Medical assessment: ① Blood Pressure (140/90mmHg) ② Cholesterol (220mg/dL) ③ HbA1c 6.8

2. Positive energy and motivation for coping with diabetes (vs. lack of energy, depressive tendencies, and burn out):
   - Self-assessment: is strong (☺ ☺ ☺ CHECK IT; IF OKAY - MAINTAIN YOUR POSITIVE ENERGY ☺)
   - Medical rating: Suppression? (Diabetes does not hurt) - Group support?

3. My blood pressure and fitness (healthy eating and weight control):
   - Self-rating: is to be improved (☺ EATING? WEIGHT? FITNESS GROUP? DOCTOR! ☺)
   - Assessment of doctor: 140/90mmHg, 34 pounds overweight - eating control & physical activity 4. My cholesterol, lipids and cardiovascular status (physical activity and no smoking):
   - Self-rating: is to be improved (☺ SUPPORT? HOW? DOCTOR SOLUTION? ☺)
   - Assessment of doctor: cholesterol and lipids: 220mg/dL improvement program (IAP)

5. My blood glucose control (HbA1C long-term value; avoiding glucose 'hypos' and 'hypers'):
   - Self-rating: is (very) good (☺ ☺ ☺ MAINTAIN IT. CONTINUE LIFESTYLE AND CONTROL ☺)
   - Assessment of doctor: HbA1c 6.8; "Eating addition?" (fat diet?) - Diabetes support group?

6. The support for a healthy lifestyle with my diabetes in my social environment (healthy eating, physical activity, no smoking:
   - Self-assessment: iI need more support (☺ HELP? GROUP? THERAPY? SOLUTION? ACTION! ☺)
   - Medical impression: Wife is cooking heavy polish food? ↓ Partner control or support group?

7. My acceptance of support, individualized support by my doctor, cooperation with my medical team and readiness to act consequently:
   - Self-assessment: (☺ HOW? 'SUPPORT'? GROUP? DOCTOR: ACTION ☺)
   - Medical rating: ① Change eating (wife) Suggestion: ② fitness group and ③ support group 8. Eating behavior (weight control, healthy eating and physical activity):
   - Self-assessment: to be improved (☺ EATING CONTROL: PARTNER? GROUP? ACTION ☺)
   - Medical rating: realization is not satisfactory (see question 7): Group support 9. My knowledge about self-care, my therapy adherence and quality of self-care:
   - Self-assessment: should be improved (☺ HOW TO IMPOVE? LIKE THIS! SUPPORT? ACTION! ☺)
   - Medical rating: ① Positive energy? (green) ② Severe deficits in self-care (orange) ③ Urgent: change of lifestyle (red)

10. My coping with diabetes, adaptation of lifestyle with physical activity and quality of life in total:
    - Self-assessment: is difficult (☺ HOW TO IMPROVE? GROUP? SOLUTION WITH DOCTOR ☺)
    - Medical rating: Definite need for action: URGENT Ind. Action Program (Support!)

FIG. 18

InDiMa DRM TYPE 2_0 GUIDE_PATIENT

| Code number: | 754-365-128-001 | Name: | Barnie Miller | Date: | January 18, 2013 |

*Legend:*

| | | | |
|---|---|---|---|
| "4" = red: urgent action | "3" = orange: must change | "2" = yellow: improve | "1" = green: okay - good |

InDiMa GUIDE (DIABETES TYPE 2)
Patient's Self-Assessment (and 'Reality Check' by Doctor): Collaborative Care 1. My overall physical and psychological health:

Self-rating: | | | ⊠⊠⊠ is (very) good (☺ ☺ ☺ MAINTAIN IT; PROVIDE SUSTAINABILITY ☺)
   Medical assessment: ||||||⊠⊠⊠┼┼┼┼⊠⊠⊠ _____
   (please mark one box)        (comment)

2. Positive energy and motivation for coping with diabetes (vs. lack of energy, depressive tendencies, and burn out):

Self-assessment: | | | ⊠⊠⊠ is strong (☺ ☺ ☺ CHECK IT; IF OKAY - MAINTAIN YOUR POSITIVE ENERGY ☺)
   Medical rating: ||||||⊠⊠⊠┼┼┼┼⊠⊠⊠ _____
   (please mark one box)        (comment)

3. My blood pressure and fitness (healthy eating and weight control):

Self-rating: | | ┼┼┼┼ | is to be improved (☺ EATING? WEIGHT? FITNESS GROUP? DOCTOR! ☺)
   Assessment of doctor: ||||||⊠⊠⊠┼┼┼┼⊠⊠⊠ _____
   (please mark one box)        (comment)

4. My cholesterol, lipids and cardiovascular status (physical activity and no smoking):

Self-rating: | | ┼┼┼┼ | is to be improved (☺ SUPPORT? HOW? DOCTOR SOLUTION? ☺)
   Assessment of doctor: ||||||⊠⊠⊠        ⊠⊠⊠ _____
   (please mark one box)        (comment)

5. My blood glucose control (HbA1C long-term value; avoiding glucose 'hypos' and 'hypers'):

Self-rating: | | | ⊠⊠⊠ is (very) good (☺ ☺ ☺ MAINTAIN IT. CONTINUE LIFESTYLE AND COHbA1c 6.8;
   Assessment of doctor: ||||||⊠⊠⊠┼┼┼┼⊠⊠⊠ _____
   (please mark one box)        (comment)

6. The support for a healthy lifestyle with my diabetes in my social environment (healthy eating, physical activity, no smoking:

Self-assessment: | | ┼┼┼┼ | iI need more support (☺ HELP? GROUP? THERAPY? SOLUTION? ACTION! ☺)
   Medical impression: ||||||⊠⊠⊠┼┼┼┼⊠⊠⊠ _____
   (please mark one box)        (comment)

7. My acceptance of support, individualized support by my doctor, cooperation with my medical team and readiness to act consequently:

Self-assessment: | | ┼┼┼┼ | (☺ HOW? 'SUPPORT'? GROUP? DOCTOR: ACTION ☺)
   Medical rating: ||||||⊠⊠⊠┼┼┼┼⊠⊠⊠ _____
   (please mark one box)        (comment)

8. Eating behavior (weight control, healthy eating and physical activity):

Self-assessment: | | ┼┼┼┼ | to be improved (☺ EATING CONTROL: PARTNER? GROUP? ACTION ☺)
   Medical rating: ||||||⊠⊠⊠┼┼┼┼⊠⊠⊠ _____
   (please mark one box)        (comment)

9. My knowledge about self-care, my therapy adherence and quality of self-care:

Self-assessment: | | ┼┼┼┼ | should be improved (☺ HOW TO IMPOVE? LIKE THIS! SUPPORT? ACTION! ☺)
   Medical rating: ||||||⊠⊠⊠┼┼┼┼⊠⊠⊠ _____
   (please mark one box)
                    _____
                    (comment)

10. My coping with diabetes, adaptation of lifestyle with physical activity and quality of life in total:

Self-assessment: | | ┼┼┼┼ | is difficult (☺ HOW TO IMPROVE? GROUP? SOLUTION WITH DOCTOR ☺)
    Medical rating: ||||||⊠⊠⊠┼┼┼┼⊠⊠⊠ _____
    (please mark one box)        (comment)

FIG. 19

InDiMa DRM TYPE 2_0 GUIDE_PATIENT

| Code number: | 754-365-128-001 | Name: | Barnie Miller | Date: January 18, 2013 |
|---|---|---|---|---|

0. Your Health and Diabetes Management: What is Your Status? (Questions 1, 2, 6, 7 and 8)
   (1) Your health, (2) your energy and motivation for coping with diabetes, (6) support for your diabetes management,
   (7) your cooperation with your medical team, and (8) your eating behavior is rated by you as?

Self-rating:

| STADIUM 2 | NEED FOR IMPROVEMENT ( ☺ DISCUSS IT WITH YOUR DOCTOR - SOLUTION ☺ ) |

Analyze your situation and discuss it with your partner and whoever is supporting you: *"What can I improve and how?"*
   Discuss with your doctor, where and how improvement is possible.

Suggestion:
   For further analysis you might go back to your personal Portfolio Page and continue with the 10 questions of the 'ANALYZER' in order to asses the '10 Success Factors for diabetes management'.

I. Three Medical Cor Criteria: Congruence of Self-Assessment and 'Reality Check' (Questions 3, 4 and 5)
   You rated your (1) blood pressure, (2) cholesterol and lipids and (3) blood glucose as:

Self-rating:

| STADIUM 2 | NEED FOR IMPROVEMENT ( ☺ DISCUSS IT WITH YOUR DOCTOR - SOLUTION ☺ ) |

Check first whether your doctor and hte medical team share y our self-rating.
   Analyze your situation and discuss it with your partner and whoever is supporting you: *'What should I improve and how?'*
   Discuss with your doctor where and how improvement is possible. Think about support, which may be helpful in your situation.

Suggestion:
   To develop your best 'Individualized Action Program' you might go back to your personal Portfolio Page, please:
   (1) answer the 'ANALYZER' with the '10 Success Factors for your diabetes management'
   (2) continue with the 'SUPPORTER' in order to develop your "Individualized Support System'
   (3) finally, evaluate of your inner situation, your eating behavior, your energy and stress management
       by continuing with the 'ENGAGER'.
   This is the best way to develop and confirm your 'Individualized Action Program'. click here II. Support for Diabetes Management (Questions 6 and 7)
    The support for your diabetes management for a healthy lifestyle by partner, family and friends, your acceptance of
    help and y our cooperation with your medical team as well as your readiness to act is:

Self-rating:

| STADIUM 2 | ☺ NEED FOR IMPROVEMENT SUPPORT ANALYZE AND IMPROVE YOUR SUPPORT SITUAION ☺ ) |

Think about support, which may be helpful in your situation and try to find out, what is working for you with your partner, family and friends. Discuss with your doctor, where and how you could get improved support.

Suggestion:
    The basis for your successful diabetes management should be improved: so you might go back to your personal Portfolio Page and continue with the 'SUPPORTER' to get some insight and ideas how to create the best possible 'Support System' for you. click here

FIG. 20

InDiMa DRM TYPE 2_0 GUIDE_PATIENT

| Code number: | 754-365-128-001 | Name: | Barnie Miller | Date: January 18, 2013 |
|---|---|---|---|---|

III. Positive Energy, Stress Management (with Burn Out Prevention) and Eating Addiction (Questions 2 and 8)
*The positive energy and motivation for my coping with diabetes to avoid lack of energy, depressive tendencies and burn out as well as my eating behavior is:*

Self-assessment:

| STADIUM 2 | ☺ SOME NEED FOR IMPROVEMENT ( FURTHER ANALYSIS AND IMPROVEMENT ☺ ) |

Reflect the stress factors in your life and answer the questions of hte instrument 'Individual Stress-Test' (IST: Instrument 031) in order to get a more differentiated picture of your situation.

Suggestion:
You might go back to your personal Portfolio Page:
(1) Continue with the 'ENGAGER'
(2) After this you might answer the 'Individual Stress Test' (IST: Instrument 031) for a detailed analysis of your stress and energy situation and Instrument 033: 'Controlled Healthy Eating'.  click here IV. Overall Health and Coping with Diabetes (Questions 1, 9 and 10)
*In relation to your health, your diabetes management and coping with diabetes your assessment is:*

Self-assessment:

| STADIUM 2 | NEED FOR IMPROVEMENT ( ☺ ANALYZE IT - DOCTOR? IMPROVEMENT ☺ ) |

If your positive evaluation is shared by the impression of the medical team:
Reflect your situation and discuss it with your support partner: 'What can I improve and how?' 'Who (else) could support me?'
Discuss your plan with your doctor: where and how improvement is possible.
Define an improved "Individualized Action Program'.
In order to prepare your improvement program:
Suggestion: *Please, go back to your personal Portfolio Page and continue for further analysis with the 'SUPPORTER' and 'ENGAGER'.*  click here

If your positive evaluation is NOT confirmed by the medical team:

Advice:
For '3' and '4' ( 'orange' and 'red') by the medical team: go back to your personal Portfolio Page and continue for further analysis with the
(1) 'SUPPORTER',
(2) 'ENGAGER' and finally go to the
(3) 'REALIZER'.  click here FIG. 20 - Continued http://www.indimasurvey.com/PortfolioPSP/index.asp?state=3

InDiMa
Individualized Diabetes Management

Personal Portfolio Page
Barne Miller
barnie.miller@gmx.com

→ Welcome
→ Surveys
→ Reports
→ Language
→ Log off

Surveys

This page provides an overview of all questionnaires due to completion or which you have completed already. Here you also can follow the data entry status of your respondents.

| Surveys | Start Date | Deadline | | |
|---|---|---|---|---|
| Adam Miller Case Study_ANALYZER | 8-1-2013 | 31-12-2013 | barnie.miller@gmx.com | ☑ |
| Adam Miller Case Study_ENGAGER | 8-1-2013 | 31-12-2013 | barnie.miller@gmx.com | ☑ |
| Adam Miller Case Study_GUIDE | 8-1-2013 | 31-12-2013 | barnie.miller@gmx.com | ☑ |
| Adam Miller Case Study_REALIZER | 8-1-2013 | 31-12-2013 | barnie.miller@gmx.com | ☑ |
| Adam Miller Case Study_SUPPORTER | 8-1-2013 | 31-12-2013 | barnie.miller@gmx.com | ☑ |
| DRM Type 2_0 GUIDE_Doctor | 1-12-2012 | 1-12-2013 | barnie.miller@gmx.com | ☑ |
| DRM Type 2_S1 ANALYZER_Doctor | 1-12-2012 | 1-12-2013 | barnie.miller@gmx.com | ☑ |
| DRM Type 2_S2 SUPPORTER_Doctor | 1-12-2012 | 1-12-2013 | barnie.miller@gmx.com | ☑ |
| DRM Type 2_S3 ENGAGER_Doctor | 1-12-2012 | 1-12-2013 | barnie.miller@gmx.com | ☑ |
| DRM Type 2_S4 REALIZER_Doctor | 1-12-2012 | 1-12-2013 | barnie.miller@gmx.com | ☑ |

| Core | | WerteUmfang: | FragenUmfang: |
|---|---|---|---|
| General Questions | ☐ | - | - |
| Core 1: IDS-Individualized Diabetes Status | ☑ | 1000 | 64 |
| Core 2: IPP-Individual Personal Profile | ☐ | - | - |
| Core 4: ISG-Individual Support and Guidance | ☐ | - | - |
| Core 5: FIN-Focus of Improvement Needs | ☐ | - | - |
| Core 6: IST-Individual Stress Test | ☐ | - | - |
| Core 7: ISG-Individual Support and Guidance | ☐ | - | - |
| Core 8: IBM-Individual Behavior Modification | ☐ | - | - |
| Core 9: IOS-Individualized Outcome Support | ☐ | - | - |
| Core 10: IRM-Individual Resource Management | ☐ | - | - |
| Core 11: IGS-Individualized Group Support | ☐ | - | - |
| Core 12: IGC-Individual Glycemic Control | ☐ | - | - |

FIG. 25

UnterAbschnitte — IngB RT&S

| | WerteUmfang: | FragenUmfang: |
|---|---|---|
| SF1 Support of Family and Friends ☑ | 1000 | 9 |
| SF2 Acceptance of Support an Guidance ☐ | 1000 | 8 |
| SF3 Motivation and Energy for Self-Care ☐ | 1000 | 3 |
| SF4 Knowledge of Diabetes Self-Care ☐ | 1000 | 3 |
| SF5 Open and Trustful Communication about Diabetes ☐ | 1000 | 3 |
| SF6 Understanding and Supporting Doctor ☐ | 1000 | 5 |
| SF7 Focus of Improvement Needs ☐ | 1000 | 9 |
| SF8 Individually Supporting Doctor and Diabetes Team ☐ | 1000 | 6 |
| SF9 Quality of Self-Care (and Health) ☐ | 1000 | 8 |
| SF10 Coping - Adaptation with Quality of Life ☐ | 1000 | 8 |

Zu lernende Personen(-gruppen)
baueKonditioniereMatrix
Personengruppe: von: 1  bis: 500
LadePersonenEin

GesamtÜberblick
Gesamtanzahl aller Fragen: 9
gesamtanzahl Personen: 100
maximaler Range: 5
minimaler Range: 1

Neuronale Analyse — NetzArten
SelfOrganizingMap(SOM) ☑
Nerual Gas ☐
BackPorpagation (BPP) ☐

Analyse — PersonenAnalyse
Person: 
Statisticshe Analyse — Analyse

Exit

| | Frage | Range | von | bis | aktiv | aktiv von | aktiv bis |
|---|---|---|---|---|---|---|---|
| 1 | I get very little help from family and friends to change my lifestyle | 5 | 1 | 5 | aktiv | 1 | 5 |
| 2 | I feel ashamed to ask for help with my diabetes self-management | 5 | 1 | 5 | aktiv | 1 | 5 |
| 3 | My family and friends do not support me with my diabetes self-management | 5 | 1 | 5 | aktiv | 1 | 5 |
| 4 | My family and friends do not supprt me in reaching my weight goals | 5 | 1 | 5 | aktiv | 1 | 5 |
| 5 | I feel [left alone] with my diabetes problems | 5 | 1 | 5 | aktiv | 1 | 5 |
| 6 | I cannot give up my lifestyle because it gives me great quality of life | 5 | 1 | 5 | aktiv | 1 | 5 |
| 7 | When I eat my recommended [diet] and carry out my [self-management], I feel like an outsider | 5 | 1 | 5 | aktiv | 1 | 5 |
| 8 | It is hard for me to decide whether to take the risk of an [unhealthy life] or to lose [quality of life] | 5 | 1 | 5 | aktiv | 1 | 5 |
| 9 | I have difficulty changing my lifestyle because my family and others in my environment have a similar lifestyle | 5 | 1 | 5 | aktiv | 1 | 5 |

Kategorisierung

| Patient | W.N. | Aktiv. | W.N. Assoz. | Akt. Assoz. | AnzAss.WN | AnzAss.Akt |
|---|---|---|---|---|---|---|
| 1 | 247 | 21,1110744 | ,100,121,54,78,98,151,177,48,191,113, | ,1,8,20,21,29,33,35,36,39,41, | 50 | 56 |
| 2 | 258 | 20,0176143 | ,65,40,161,148,167,139,157,71,31,58, | ,2,3,4,6,9,11,17,18,23,27,31, | 91 | 45 |
| 3 | 258 | 20,0176143 | | | | |
| 4 | 153 | 19,6466312 | ,6,183,33,36,95,194,55,96,190,127,61, | ,54,76,80,97,107,119,133,144 | 36 | 11 |
| 5 | 293 | 17,4528865 | ,102,125,44,14,13,16,37,38,70,105,112 | ,5,7,12,14,15,19,24,40,43,44, | 15 | 53 |
| 6 | 13 | 19,6587257 | ,22,90,137,87,12,115 | | 6 | |
| 7 | 256 | 16,8411121 | | ,25,32,137,155,159 | | 5 |
| 8 | 93 | 20,8651618 | | | | |
| 9 | 217 | 19,7054920 | | | | |
| 10 | 252 | 33,8189201 | | ,10,26,28,30 | | 4 |
| 11 | 331 | 19,2237434 | | ,22,34,84,116,139,140 | | 6 |

Werte Tabelle

Welche Spalte? 3

Welche Reihe? 1

Winner: 35, 101, 154, 42, 174, 52, 11, 173, 77, 181, 176, 18, 80

Aktiv.: 158, 160, 162, 164, 166, 167, 168, 175, 176, 178, 179, 182, 190, 194, 195, 197, 199

Kategorisierung

| Patient | W.N. | Aktiv. | W.N. Assoz. | Akt. Assoz. | AnzAss.WN | AnzAss.Akt |
|---|---|---|---|---|---|---|
| 1 | 247 | 21,1110744 | ,100,121,54,78,98,151,177,48,191,113, | ,1,8,20,21,29,33,35,36,39,41, | 50 | 56 |
| 2 | 258 | 20,0176143 | ,65,40,161,148,167,139,157,71,31,58, | ,2,3,4,6,9,11,17,18,23,27,31, | 91 | 45 |
| 3 | 258 | 20,0176143 | | | | |
| 4 | 153 | 19,6466312 | 6,183,33,36,95,194,55,96,190,127,61, | 54,76,80,97,107,119,133,144 | 36 | 11 |
| 5 | 293 | 17,4528865 | ,102,125,44,14,13,16,37,38,70,105,112 | ,5,7,12,14,15,19,24,40,43,44, | 15 | 53 |
| 6 | 13 | 19,6587257 | ,22,90,137,87,12,115 | | 6 | |
| 7 | 256 | 16,8411121 | | ,25,32,137,155,159 | | 5 |
| 8 | 93 | 20,8651618 | | | | |
| 9 | 217 | 19,7054920 | | | | |
| 10 | 252 | 33,8189201 | | ,10,26,28,30 | | 4 |
| 11 | 331 | 19,2237434 | | ,22,34,84,116,139,140 | | 6 |

Werte Tabelle

Welche Spalte?
3

Welche Reihe?
1

Winner: 150, 158, 1, 135, 92, 147, 145, 20, 109, 83, 35, 101, 154

Aktiv.: 129, 135, 136, 158, 160, 164, 166, 168, 175, 176, 178, 182, 190, 194, 195, 197, 199

Kategorisierung

| Patient | W.N. | Aktiv. | W.N. Assoz. | Akt. Assoz. | AnzAss.WN | AnzAss.Akt |
|---|---|---|---|---|---|---|
| 1 | 247 | 21,1110744 | ,100,121,54,78,98,151,177,48,191,113, | ,1,8,20,21,29,33,35,36,39,41, | 50 | 56 |
| 2 | 258 | 20,0176143 | ,65,40,161,148,167,139,157,71,31,58, | ,2,3,4,6,9,11,17,18,23,27,31, | 91 | 45 |
| 3 | 258 | 20,0176143 | | | | |
| 4 | 153 | 19,6466312 | ,6,183,33,36,95,194,55,96,190,127,61, | ,54,76,80,97,107,119,133,144 | 36 | 11 |
| 5 | 293 | 17,4528865 | ,102,125,44,14,13,16,37,38,70,105,112 | ,5,7,12,14,15,19,24,40,43,44, | 15 | 53 |
| 6 | 13 | 19,6587257 | ,22,90,137,87,12,115 | | 6 | |
| 7 | 256 | 16,8411121 | | ,25,32,137,155,159 | | 5 |
| 8 | 93 | 20,8651618 | | | | |
| 9 | 217 | 19,7054920 | | | | |
| 10 | 252 | 33,8189201 | | ,10,26,28,30 | | 4 |
| 11 | 331 | 19,2237434 | | ,22,34,84,116,139,140 | | 6 |

Werte Tabelle

Welche Spalte? 3

Welche Reihe? 1

Winner
42
174
52
11
173
77
181
176
18
80
102
125
44

Aktiv.
184
185
186
187
188
189
190
191
192
193
194
195
196
197
198
199
200

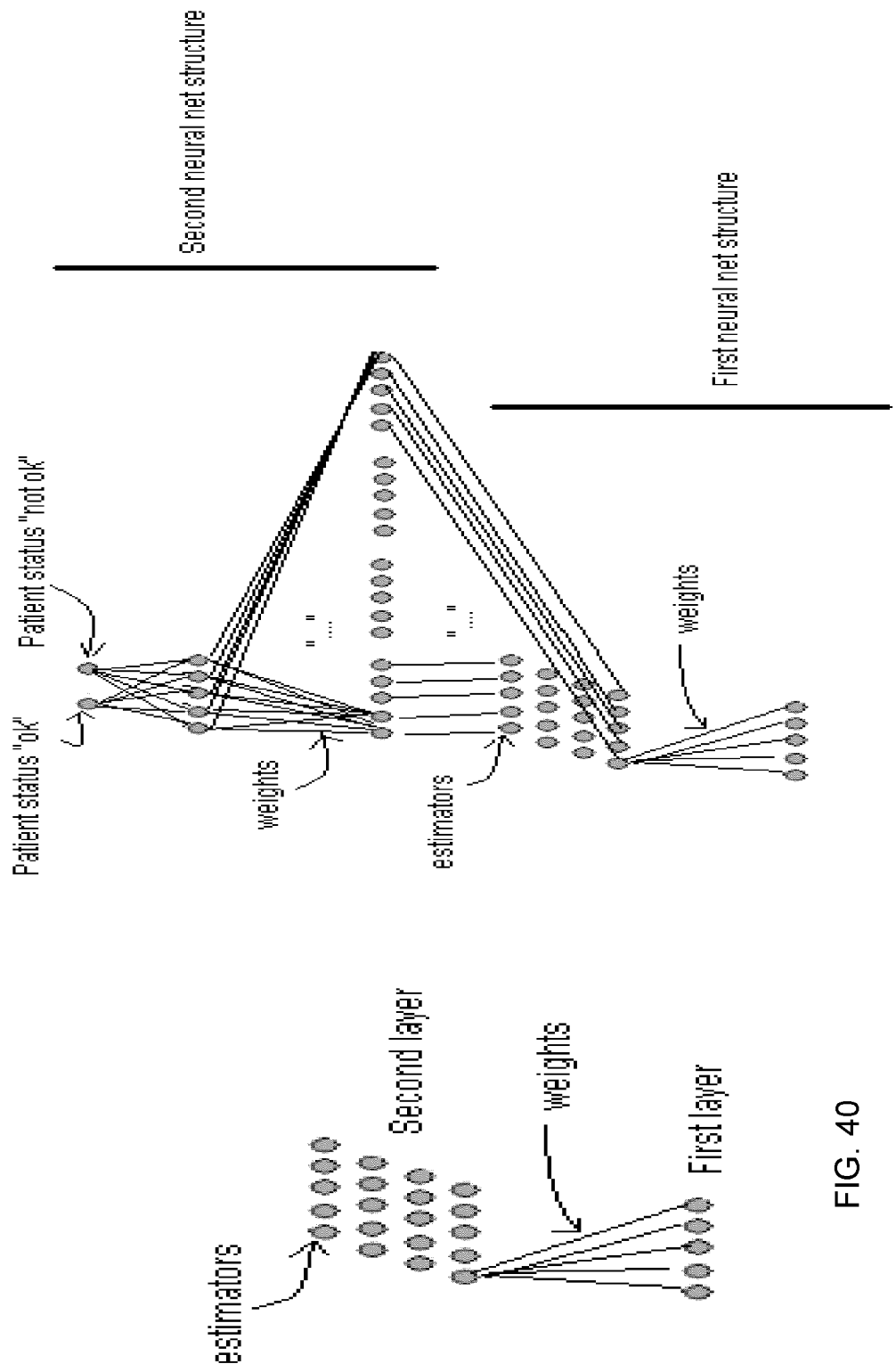

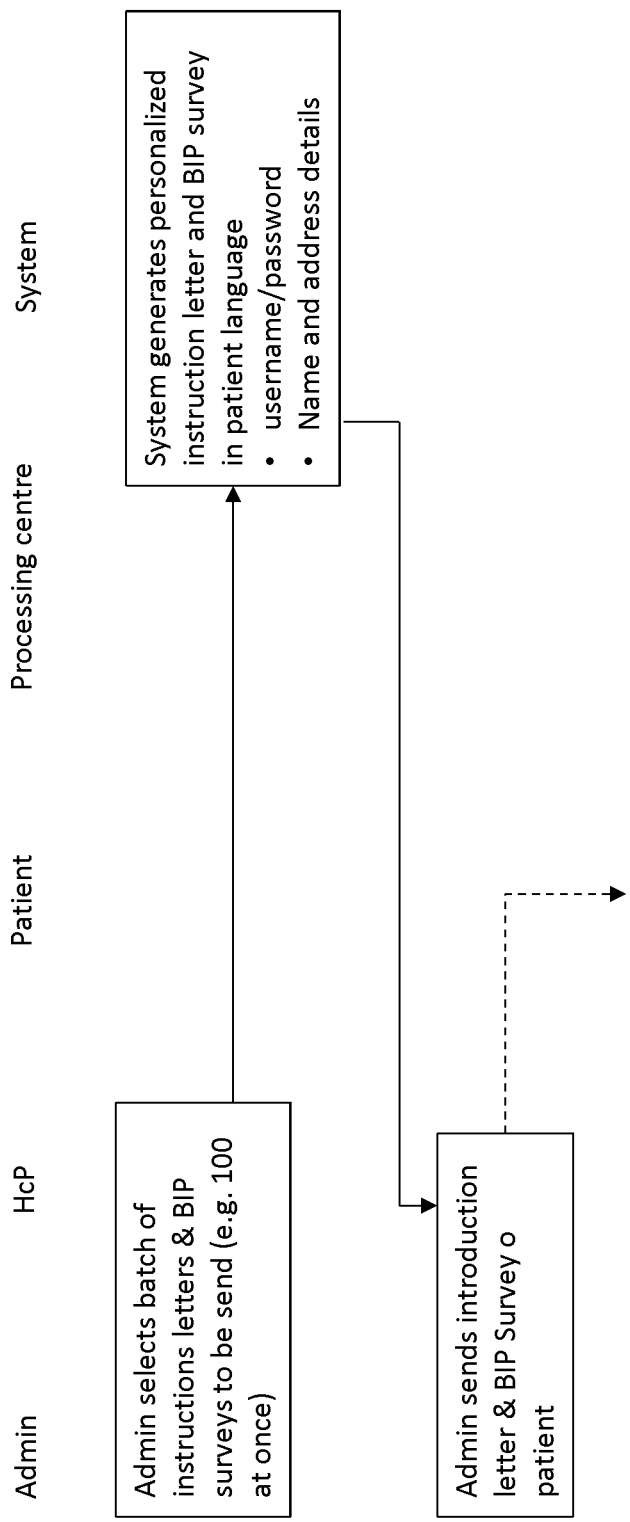
FIG. 49 - Continued

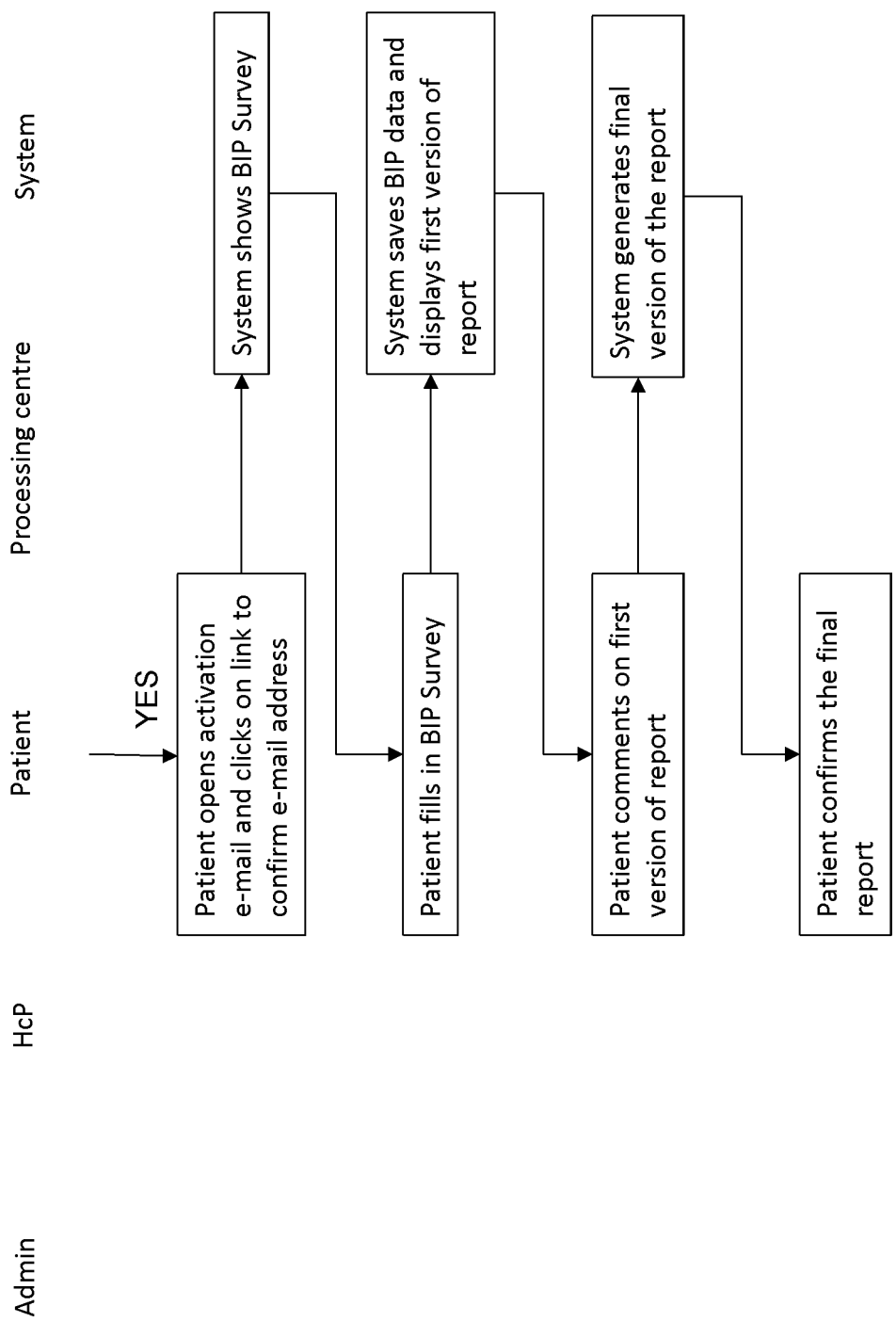
FIG. 50 - Continued

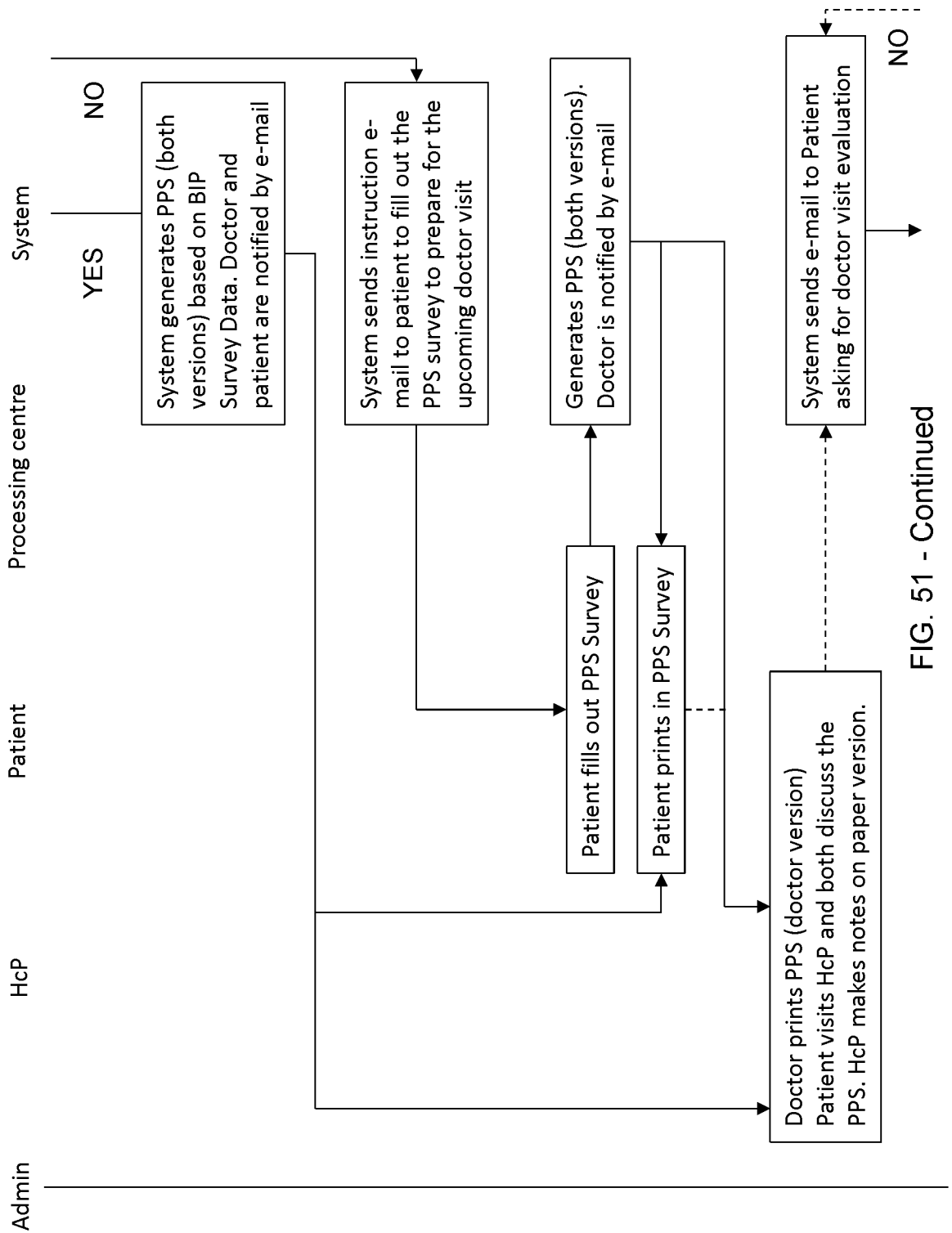
FIG. 51 - Continued

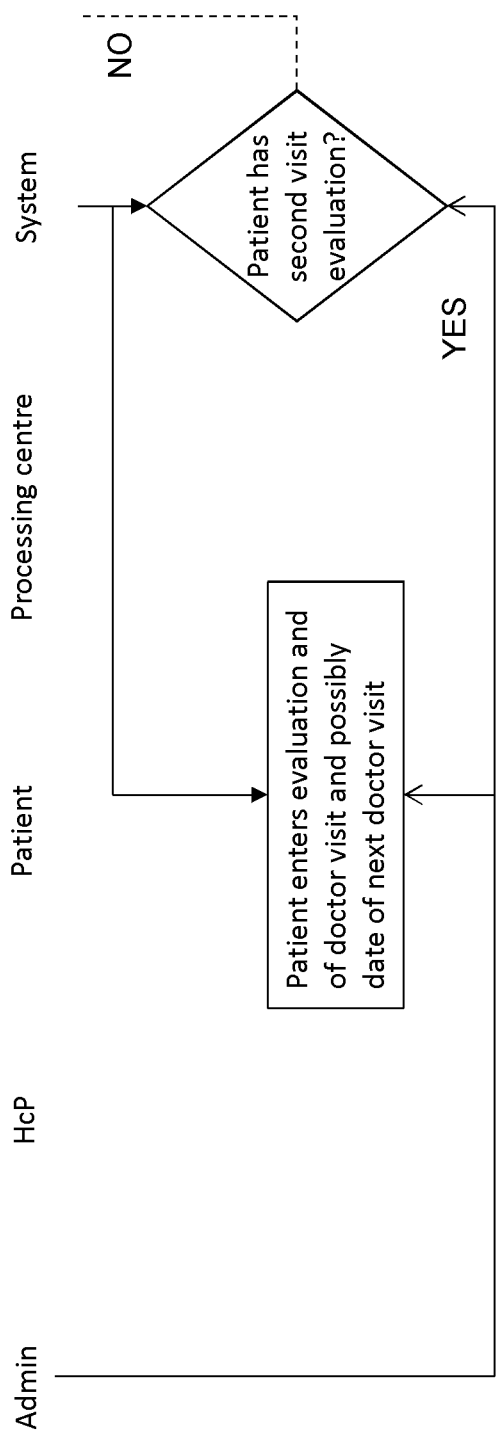
FIG. 51 - Continued

"INDIMA APPARATUS" SYSTEM, METHOD AND COMPUTER PROGRAM PRODUCT FOR INDIVIDUALIZED AND COLLABORATIVE HEALTH CARE

CROSS-REFERENCE TO RELATED APPLICATIONS

This patent application claims priority from U.S. patent application Ser. No. 61/752,887, filed Jan. 15, 2013 and U.S. patent application Ser. No. 61/588,721, filed Jan. 20, 2012, both of which are incorporated herein by reference in their entireties.

COPYRIGHT AUTHORIZATION

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

TECHNICAL FIELD

The present technology relates to a system and method for individualized life management in connection with individualized and collaborative health care involving a plurality of individuals, using groups of state parameters for defining a state of each individual, and using groups of action parameters for defining treatment options and/or behavior options targeted at an individual.

BACKGROUND DESCRIPTION

A systemic analysis of "Health Care Management of Today" would fill a book which is not possible for giving just background information.
1.1 "Health Management" Instead of "Disease Management"
Some 3000 years ago, in China, "Health Management" was literally "health-oriented". It was therefore comprehensive and integrative and therefore necessarily preventive: The ancient Chinese "Health Care Professionals" (HCP's) were rewarded for the health of their "clients" (unlike the Latin origin word "patient", literally translated "suffering ones") and not for treating diseases.
On the contrary, today's health care systems can be defined as "health reparation" systems or "disease management" systems for which it is a common saying in the American Medical Community that there are "rushed doctors" working "in a fragmented system".
1.2 Alienation from Individual Health Management: The Fragmented Health Care System
It seems that the citizens of the First World countries in the so-called "Trias" (North America with USA, Canada; Europe; Japan plus ASEAN) are "separated" from their health to use a strong term.
Especially in the United States of America, the pharmaceutical companies and the "payors", the insurance companies, are more or less in one hand. Thus, the doctor working in an HMO is very much in a situation of an "economically dependent" person (and economic "victim") with the patient so to say being the "victim of the victim".

The United States of America make up 4% of the First World population. They spend 40% (factor 10 !) for "disease management" with very poor results: 66% of the population are overweight, 34% are "obese", and the rate of diabetics type 2 (which is a result of the "individual health management" of the persons concerned) is by far the highest in all First World countries. This situation has been described by Prof. Dr. Paul Ciechanowski, a leading US expert for Diabetes Management, Depression Management, "Diapression" ("An Integrated Model for Understanding the Experience of Individuals With Co-Occurring Diabetes and Depression", 2011): "the rushed doctor in a fragmented system".

Therefore, a comprehensive and integrative person/patient-centered "health care" model is needed. Health education is not dealt with in elementary, secondary or high schools—nor in colleges or at universities. Although it is the most valuable good of mankind, it is not treated and protected as such.
1.3 Role Concepts of Patients and Doctors in the Western World of Today (Examples USA and Germany/Europe)
An analysis of the role concepts of "patients" and doctors/HCP's.

The research in Europe (in Germany) which also reflects results in the USA and Japan (although the frequency in the groups is certainly different in these countries and the social background influences the results so that in each country a specific analysis is needed) is described in the following in order to give some basic insight.
The following pattern of patients exist:
Group 1 "DETERMINISTIC GROUP": "Health is determined by fate (good or back luck)."
Group 2 "MEDICAL" BELIEVER GROUP": "I cannot do anything. My (high quality) doctor is in charge of my health."
Group 3 "NATURE GROUP": "Avoid the doctor and the medical institutions. Live healthy—and everything will be fine."
Group 4 "ENLIGHTENED COLLABORATIVE CARE GROUP": "I am aware of the fact that it is my health and my life: So I am looking for a doctor/HCP as a professional partner and act as a more or less self-conscious and responsible partner of my doctor and/or the health care professionals."
The doctors have corresponding role concepts:
Authoritarian doctors like the deterministic group patients. These patients listen to the doctor as if he was "fate" or even "God".
The paternalistic doctors prefer the medical believer group. They are seen as an authority and the patients cling to their lips.
All groups of doctors are somewhat distant and skeptical about the nature group which avoids contact with the doctors and is more of an "anti business model". The "enlightened collaborative care group" is officially preferred by all doctors. But one thing is what is said in theory ("We all like and strive for 'collaborative care'")—the reality may be far away from it. According to several research results, 80% of the patients in the USA receive about 20% of the health care visit time of the American doctors. The other 20%, the "system-preferred" receive 80% of the health care visit time.
1.4 Standardized Medical Treatment
It is evident and need not be proved that first of all, standardized medical care is necessary for all patients to create a basis ("basic service").

1.5 the Patient as an "Object" Vs. The Responsible "Empowered" Self-Conscious Patient Again, there is no need to argue that the patient as an object certainly receives the minimum care and has good chances to survive.

For an optimum life span, for best quality of life, and for a best medical treatment in the case of illness, however, clearly the "empowered" patient, showing initiative, empowerment and being able to carry out a "high quality self-care" has the better life.

1.6 Openness, Trust, and a Positive Doctor-Patient Relationship are the Basis for Collaborative Care This again is obvious and need not be proved (although there is a huge amount of research data proving this as an empirical fact).

1.7 Individualized and Person-Centered Health Care for Chronic Diseases (ISM)

Medical care has improved enormously in the last century. The life expectancy of today's generations has been increased significantly. Where, however, addictive patterns and very change-resisting behavior patterns are prevalent, the classical care situation with a short contact between patient and doctor reaches its limits.

This is true for all chronic diseases. So there is a need for the patients with chronic diseases to receive "treatment support" or even "adaptation and behavior modification support".

1.8 Lifelong Support for Chronical Disease Patients is Necessary ("Individualized Support Management"=ISM)

All the existing research has shown that patients with chronic diseases need support and there are altogether four sources:
  (1) the person himself/herself (self-motivation, internet contacts, health care education, training etc.);
  (2) the direct social environment (support by partner, family, and friends);
  (3) the "second" social environment and groups (like patient support groups, training groups, and self-care groups);
  (4) the medical support by doctors and health care practitioners (as the last—and financially most expensive and also limited—resource).

2. The Corresponding Challenges and Solutions for the Existing Problems 2.1 "Standardized" Treatment The "Health Care Repair Systems" of today (with the "rushed doctor in a fragmented system") are disease-focused with patients as (more or less) an "object" of a (more or less) standardized treatment.

2.2 "Separation" from the Own Health

The modern patients are more or less "separated" from or "alienated" by their own health; only very few (less than 10% of the population) are really fully empowered and "in charge of their individual health management".

2.3 Need for Help

Both, patients and doctors, need help.

Let us take the example of the US American society: More than 50% of the doctors suffer from burnout syndrome and doctors starting show the normal depression rate of the population (4%) which increases after one year up to striking 25%.

Let us take the following examples of diabetes care: Only 7% of the US patients reach the three objectives which are relevant to preserve their lives: reaching the blood pressure goals, reaching the objectives for lipids/cholesterol, and reaching the average level $HbA_{1c}$ for blood sugar, avoiding extreme hypoglycemic and hyperglycemic states.

2.4 Standardized Vs. Individualized Treatment of Diabetes Type 2 Patients

All diabetes type 2 patients are certainly checked in terms of bio-medical status (level 1). This is, however, only the "Peak of the Iceberg" (see Annex I).

2.5 Treatment of the Patient as an "Object" in a "Standardized Procedure"

If the patient is treated as an "object" in a "standardized treatment procedure", the results are inferior (especially in person- and psychology-related chronic diseases).

Example 1

More than 30% of diabetes patients with strong depression (about 12%) and some 20% with clear depressive tendencies (Paul Ciechanowski, MD, PHD, article on "Diapression": "Diapression: An Integrated Model for Understanding the Experience of Individuals With Co-Occurring Diabetes and Depression", 2011) are not reached. It is evident that a person suffering from depression is not open for a high quality self-care diabetes treatment.

Example 2

Some 50-70% of the patients with diabetes mellitus type 2 suffer from an "eating addiction" (F. Kiefer, M. Grosshans, "Beitrag der Suchtforschung zum Verstandnis der Adipositas", 2009), and show the same symptoms/activity patterns in their brain when looking at their favorite "juicy hamburger" or other favorite food as alcoholics do when looking at alcohol.

Example 3

It is also evident that "Adipositas Patients" who are "eating addicts" in diabetes mellitus type 2 need support and a psychiatric treatment (Prof. F. Kiefer, University of Heidelberg, Central Institute for Addictive Diseases, Mannheim) and that a normal "rational appeal" will help as little as telling a heroin or alcohol addict: "It would be better if you did not take heroin or if you did not drink alcohol."

2.6 the Patient as an "Object" within a Highly Complex Technological Process

The cost-driven medical care and health care systems of today have the effect that the patients have become more and more an "object" within a highly complex technological process. The very disappointing results with chronic diseases and with all diseases which need "to take into account the needs of the person" show that there is a definite need for change.

2.7 The Threshold Between Patients and Doctors

There is a threshold and barrier between many patients and doctors which needs to be overcome. This, however, is very difficult especially for the complex topics and needs of treating chronic diseases and treating diseases with intimate personal aspects which require to understand the psychology and the personal situation of a "patient" in order to empower him to be a "client".

2.8 Rational Appeals or "Logic" are not Helpful

Lifestyle adaption and behavior modification for diabetes type 2 patients as well as for patients with depression or the combination of both, patients with diapression as well as support for patients with diabetes type 1 (psychological treatment support) is not achieved by rational appeals or "logic".

2.9 Coping with Crisis Situations

All patients with chronic diseases facing (for depressive patients twice in a lifespan) a crisis where they need definite and urgent support. Leaving patients with chronic diseases alone for themselves does not lead to best results.

SUMMARY OF EMBODIMENTS OF THE DISCLOSURE

First Aspect

A First Aspect of the disclosure pertains to a system for individualized and collaborative health care involving a plurality of individuals, using groups of state parameters for defining a state of each individual, and using groups of action parameters for defining treatment options, support options and/or behavior options targeted at an individual within the plurality of individuals. The system includes a data processor means adapted for processing input data, which are based on the groups of state parameters, into output data, which are the basis for the groups of action parameters, using defined relationships/assignments between groups of state parameters and groups of action parameters. A data storage means is adapted for storing the groups of state parameters, the groups of action parameters and the defined relationships/assignments between groups of state parameters and groups of action parameters. A data communication system/platform is adapted for communicating state parameters selected from the groups of state parameters and/or action parameters selected from the groups of action parameters among the plurality of individuals.

Referring now to specific features of the First Aspect, the data processor means can comprise an adaptive structure where the defined relationships/assignments between groups are redefined/updated using empirical or by neural network analysis defined relations and correspondences pairs of action parameter groups and state parameter groups. The adaptive structure can include one or more of (e.g., is selected from the group consisting of) expert systems, fuzzy logic, neural networks, genetic and/or evolutionary algorithms and combinations thereof. The system can be web-based including one or more of PC-application, tablet application, iPhone and smartphone-technology and other electronic communication devices. The groups of state parameters can include one or more of (e.g., are selected from the group consisting of) biomedical/physiological (B), psychological (P), personal (P) and socio-economic (S) characteristics/attributes of health care clients. A health care client-specific state parameter group can be based on assessment of the health care client using a questionnaire for the self-assessment.

Second Aspect

A Second Aspect of this disclosure pertains to a method for individualized and collaborative health care involving a plurality of individuals, using groups of state parameters that define a state of each individual, and using groups of action parameters that define individualized treatment options, individualized support options and/or individualized behavior options targeted at an individual within the plurality of individuals. The method includes processing input data, which are based on the groups of state parameters, into output data, which are the basis for the groups of action parameters, using defined relationships/assignments between groups of state parameters and groups of action parameters. The groups of state parameters, the groups of action parameters and the defined relationships/assignments between groups of state parameters and groups of action parameters are stored. State parameters selected from the groups of state parameters and/or action parameters selected from the groups of action parameters are communicated among the plurality of individuals.

Referring to specific features of the Second Aspect, the defined relationships/assignments between groups can be redefined/updated using empirical pairs/empirically defined relations and neural networks determined relations of action parameter groups and state parameter groups. The groups of state parameters can include one or more of (e.g., are selected from the group consisting of) biomedical/physiological, psychological, personal and socio-economic characteristics/attributes of health care clients. A health care client-specific state parameter group can be determined by assessing the health care client using a questionnaire. The health care client-specific state parameter group can be repeatedly determined throughout the health care client's affiliation to the plurality of individuals. Communication and information exchange can be made available: among individuals belonging to a first subset (HCC), and family, friends, social environment of the plurality of individuals; among individuals belonging to a second subset (HCP) of the plurality of individuals; and between individuals belonging to the first subset (HCC) and individuals belonging to the second subset (HCP). Defined relationships/assignments between action parameter groups and state parameter groups can be made available for communication and information exchange among the plurality of individuals. The individuals of the plurality of individuals can be categorized into different categories of individuals based on their respective state parameter groups and corresponding action parameter groups.

Third Aspect A

A Third Aspect A of this disclosure features a method for individualized and collaborative health care involving a plurality of individuals, including providing state parameters for defining a state of each individual health care client (HCC), wherein the state parameters are based on information including one or more of (e.g., selected from the group consisting of) biomedical, physiological, psychological, personal and socio-economic information about the HCC and combinations thereof. The HCC, who has a health management task, conducts a self-assessment based on the state parameters. A report of the self-assessment of the HCC is provided to a health care professional (HCP). The HCP has physiological and biomedical tests conducted on the HCC and has biomedical facts obtained from the HCC concerning the health management task, which can include facts as to health development, an individualized prevention program, self-care, and individualized support. Need-for-action levels are determined indicating urgency in need for action in addressing the health management task (e.g., treating the disease or the health problem) of the HCC. The need-for-action levels are determined by comparing an extent of a deviation between results of the self-assessment compared to results of the physiological and biomedical tests and the biomedical facts, and thereby evaluating the HCC's risks and chances. The HCP conveys to the HCC the need-for-action levels, thereby providing the HCC with a learning model in self-care and individualized disease management. The HCP uses the need-for-action levels to determine appropriate action parameters including an individualized and collaborative health care action plan ("Individualized Action Program") for the HCC.

Referring to specific features of the Third Aspect A, defined relationships/assignments between the action parameters and the state parameters can be made available for communication and information exchange among the plurality of individuals. The need-for-action levels can include one or more of (e.g., are selected from the group consisting of) a first level where the deviation is determined to be extreme, a second level where the deviation is determined to be definite, a third level where the deviation is determined to be some difference, and a fourth level where no deviation is found. The action parameters can include medical therapy groups and/or prevention or support groups of the HCCs and others exchanging information about the health management task (e.g., disease or the health problem) or a life management task (see ILM task), which medications, the support groups and the medical therapies have been successful, partially successful or were a failure or create experience-based options that can be used for the Individualized Action Program. The self-assessment can be a web-based questionnaire which is sent to the HCC via a communication network linking places or things including one or more of (e.g., selected from the group consisting of) individual hospitals, health care professionals' practices or clinics, offices of support groups, the HCCs homes, mobile wireless communication devices of the HCCs and the HCPs, and combinations thereof. The prevention or support program or the health management task (e.g., treating or preventing a disease or health problem) can pertain to one or more of cardiovascular disease, diabetes, depression, alcoholism, obesity, overweight, stress, burn-out, psychosomatic disease, gastro-intestinal disease, chronic orthopedic disease, chronic pain-related disease, any other chronic disease, drug addiction and combinations thereof. The health management task can be treating or preventing diabetes and the Individualized Action Program for the HCC is tailored to reaching blood pressure goals, reaching objectives for lipids/cholesterol, and reaching an average level $HbA_{1c}$ for blood sugar, avoiding extreme hypoglycemic and hyperglycemic states. The health management task can comprise treating or preventing diabetes and the physiological tests pertain to one or more of blood glucose or $HbA_{1c}$ level, lipid level and cholesterol level of the HCC and measurements of one or both of weight and blood pressure can be used with the physiological tests.

Third Aspect B

The Third Aspect B of this disclosure includes all of the features of the Third Aspect A and also includes utilizing at least the need-for-action levels and the action parameters in connection with a neural network system to determine a prediction of future development of the disease or the health problem.

Referring to specific features of the Third Aspect B, the neural network can further source the groups of state parameters defined in the state of each individual to determine the prediction of future development of the disease or health problem, a related cost of disease management or health and prevention. The neural network can further source a validated database of pairs of groups of state parameters and groups of action parameters. This method can include the step of iteratively conducting the HCC's self-assessment and the HCP's obtaining of the physiological and biomedical tests, to update the need-for-action levels and the action parameters. This method can include the step of iteratively determining the prediction of future development of the disease or health problem, management, related cost or health and prevention, based on the updating of the need-for-action levels and the action parameters.

A self-organizing map is a type of neural network that can produce low-dimensional representations of an input space, which typically comprises high-dimensional data. The self-organizing map is self-learning in that the network is built via unsupervised learning (i.e., an unknown structure is derived from unlabeled data) and, thus, particularly useful in situations where a relationship between input and output is not fully known. The self-organizing map is also capable of preserving topological properties of the input space. Regarding another specific feature of Aspect 3B or any other neural network Aspect described herein, the neural network system comprises a self-organizing map constructed, via unsupervised learning, from a set of predetermined action parameters, a set of predetermined action levels, and corresponding predetermined disease progression data.

Fourth Aspect

A Fourth Aspect of this disclosure features a method for individualized and collaborative action planning for an individual, including obtaining information, from the individual and a professional responsible to the individual, related to a set of parameters, the set of parameters including one or more of biomedical and physiological parameters, psychological parameters, personality parameters, and socio-economic parameters. Another step is determining, for each of a plurality of success factors, a priority indicating a level of urgency of action in order to achieve the success factor. Another step is classifying the individual, utilizing a neural network structure, into a group among a set of groups based on priorities respectively determined for the plurality of success factors. Yet another step is determining an individualized and collaborative action plan for the individual ("Individualized Action Program") based on the group to which the individual is classified.

Referring to specific features of the Fourth Aspect, the priority can include one or more of (e.g., can be selected from the group consisting of) no need for action, some need for action, definite need for action, and urgent need for action. The Individualized Action Program can include option for actions to be undertaken by at least one of the individual or the professional to achieve the plurality of success factors. The method can include the step wherein at least one of the options for action and the Individualized Action Program to be undertaken by the individual or the professional relate to a condition selected from the group consisting of a health condition, financial condition, socialization condition, political condition, economical condition, and life culture condition of the individual, and combinations thereof.

Fifth Aspect

A Fifth Aspect of this disclosure features an apparatus including a processor coupled to a memory, the processor being configured to:
  generate a model of a state of an individual relative to a condition of the individual;
  generate, utilizing a set of neural networks, a predicted state of the individual at a pre-determined time period and classify the individual to a category of a plurality of categories according to the predicted state; and
  determine a customized action, based on the predicted state and the category associated with the individual, for the individual to perform to align an actual state at the pre-determined time period with a pre-determined goal state, thereby creating a controlling system for "Individualized Action Programs" based on predictions, goals and comparisons with achievements.

Referring to specific features of the Fifth Aspect, the condition of the individual can include one or more of (e.g., is selected from the group consisting of) a health condition, self-care condition, support condition, treatment adherence condition, financial condition, socialization condition, political condition, economical condition and life culture condition, of the individual, and combinations thereof. The health condition can include one or more of (e.g., is selected from the group consisting of): cardiovascular disease, diabetes, depression, alcoholism, obesity, overweight, stress, burn-out, psychosomatic disease, gastro-intestinal disease, chronic orthopedic disease, chronic pain-related disease, any other chronic disease, drug addiction and combinations thereof. The model of the state of the individual can include a set of parameters that includes at least one of a biomedical or physiological-based parameter, a communication style or psychological-based parameter, a personality-based parameter, and a socio-economical-based parameter. The set of parameters can be at least partially derived from one or more questionnaires completed by the individual. The category to which the individual is classified can indicate a level of risk and expected costs for health management to which the individual is exposed according to the predicted state. The apparatus can be integrated in a blood glucose monitor or programmed on a blood glucose meter, PC, tablet, iPhone or smart phone device.

Sixth Aspect

A Sixth aspect of this disclosure features a method for treating diabetes, including generating a patient model that specifies individual physiological and psychological parameters of a patient. The patient model is applied to a neural network system to determine a predicted state of blood pressure, cholesterol, lipids and blood glucose levels for the patient at a pre-determined time in the future. An "Individualized Action Program" is determined based at least in part on the physiological parameters of the patient model, to control blood pressure, cholesterol, lipids and blood glucose levels of the patient to a desired state or value within a pre-determined time interval or series of time intervals.

Referring to specific features of the Sixth aspect, the Individualized Action Program can include at least one of healthy eating, physical activity, support groups, medical therapy groups, insulin dose, no smoking, treatment of depression and treatment of eating addiction. The method can include utilizing a classifier to assign the patient to a category corresponding to a specific level of risk for blood pressure or weight problems, cholesterol or lipid risks or severe hyperglycemic or hypoglycemia. The level of risk can be associated with at least one of a short-term or long-term risk. The method can include utilizing the predicted state to establish a target function for an optimization system such as the Individualized Action Program, implementable by a computer. The method can include utilizing a measure of effectiveness of the Individualized Action Program to establish the target function. The method can include the step of continuously updating the patient model based on psychological data and bio-medical and physiological data and treatment adherence as well as self-care behavior of the patient over time.

Another specific feature of the Sixth Aspect can include the step of which determining the Individualized Action Program comprises applying the predicted state at the pre-determined time in the future to a second neural network system predicting and measuring validation criteria that can include at least one of health, success of disease management and costs of disease management over time.

Seventh Aspect

A Seventh Aspect of the disclosure features a method of using a computer system including a server and a database for individualized and collaborative action planning for treating a patient, including registering a patient into the system by inputting patient contact information into the system. The patient contact information is stored in the database. The server transmits a patient questionnaire to a remote device of the patient over a communication network. The server receives patient answers to questions on the patient questionnaire from the remote device of the patient. The patient answers include:

information regarding a patient self-assessment of the patient's medical and physiological condition, information regarding the patient's psychological condition, information regarding the patient's personality traits, genetic factors, and/or behavior patterns, and information regarding a patient's fitness, activities, and/or lifestyle; storing the patient answers in the database.

The method includes the step of inputting medical information about the patient from a doctor treating the patient into the server for storing in the database. The computer system processes an assessment of the patient by comparing information from the patient answers and the medical information. The computer system automatically generates a report including action parameters for treating the patient.

Specific features of the Seventh Aspect can include the following. The following step can be included in the method: wherein the step of comparing the information from patient answers to the medical information includes the step of determining a deviation from the information regarding the patient self-assessment of the patient's medical and physiological condition and the medical information input from the doctor. The method can also include the step wherein the report includes need-for-action levels indicating an urgency in a need for action based on the determined deviation. Another step can be used wherein the need-for-action levels include a first level where the deviation is determined to be extreme, a second level where the deviation is determined to be definite, a third level where the deviation is determined to be some difference, and a fourth level where no deviation is found. The database can include assessments of a plurality of other patients, and wherein the step of processing the assessment of the patient utilizes the assessments of the plurality of other patients. The medical information input by the doctor can include information derived from a review of the answers of the patient. The patient can access one or both of the assessment of the patient and the report.

Eighth Aspect

An Eight Aspect of the disclosure features a method of using a computer system including a server and a database for individualized and collaborative action planning for a particular patient, including registering a plurality of patients into the system by inputting patient contact information into the system. The patient contact information is stored in the database. The server transmits patient questionnaires to remote devices of the patients over one or more communication networks. The server receives patient answers to questions on the patient questionnaires from the remote devices of each of the patients. The patient answers are stored in the database. Also included is the step of storing medical information about the patients from one or more doctors treating the patients into the database. The computer system determines state parameters for each of the patients from the patient answers. The computer system processes assessments of each of the patients utilizing the answers and/or state parameters for any given patient and the medical information of the given patient. The computer system automatically generates action parameters for treating each of the patients based on the assessments of the patients. The computer system generates groupings of the state parameters of a given patient with the action parameters of the given patient for storing in the database. Included is the step of automatically categorizing patients into categories of patients having similarities to each other. The computer system updates the action parameters of the particular patient for storing in the database, the updating step including consideration of the action parameters of the patients in the same category as the particular patient. The computer system automatically generates a report including the updated action parameters for treating the particular patient.

Specific features of the Eighth Aspect can include the step of the patient accessing one or both of the assessment of the patient and the report. The patient answers to the questions can comprise:

information regarding self-assessments of the medical and physiological condition of each of the patients,
information regarding the psychological condition of each of the patients,
information regarding the personality traits, communication style, genetic factors, and/or behavior patterns of each of the patients, and
information regarding fitness, activities, and/or lifestyle of each of the patients.

The information of the self-assessments of the patients can include information regarding blood pressure, cholesterol and lipids, and blood glucose levels of the patients. The assessments can be made by determining deviations between the answers and/or state parameters of a given patient and the medical information of the given patient. The report can include need-for-action levels indicating an urgency in a need for action based on the determined deviation.

Ninth Aspect

A Ninth Aspect of the disclosure features a method for individualized treatment of a patient having diabetes, including providing the patient with a questionnaire including questions pertaining to groups of success factors, wherein the questions in each success factor group pertain to at least one of biomedical information, psychological information, social environment information and personality trait information about the patient, the biomedical information including information about the patient's blood pressure, lipids and blood glucose levels. The patient provides answers to the questions of the questionnaire. A report is provided to the patient based on the patient's answers, rating the patient's condition in each group of success factors. A doctor conveys to the patient information that is suitable for diabetes care of the patient based on the report, which brings about patient-driven behavior change affecting the patient's survival.

A specific feature that may be part of the method of the Ninth Aspect is wherein the diabetes care addresses biomedical development of the patient pertaining to at least one of the following: eating, weight, physical activity, support groups, blood glucose, $HbA_{1c}$, lipids, variability of hyperglycemia and hypoglycemia, smoking, and general health state.

Tenth Aspect

A tenth aspect of the disclosure features a method for individualized treatment and collaborative care of diabetes, including providing a patient with a questionnaire including questions pertaining to groups of success factors for the patient. The questions to each success factor group pertain to at least one of (1) biomedical information (Bio-Marker), (2) psychological information (Psycho-Marker), (3) personality trait information (Perso-Marker), and (4) social environment and socio-economic information (Socio-Marker) about the patient including information about the patient's blood pressure, lipids and blood glucose levels. The patient provides answers to the questions of the questionnaire, supported by a view including partner, family, friends, diabetes group(s), medical group(s), health care professionals (HCP's) and diabetes team to work out an "Individualized Action Plan". A series of reports are provided to the patient based on the patient's answers with the facts: (1) a report rating the patient's condition in each group of success factors, (2) a report to support furthermore detailed self-assessment, (3) a report categorizing 'Need for Action' and interpreting the results. The Individualized Action Plan is developed with the active engagement and involvement of the patient. The HCP conveys to the patient information that is suitable for individual support and accompanying therapies for diabetes care of the patient based on the reports, which bring about patient-driven behavior change affecting the patient's survival.

A specific feature of the Tenth Aspect can include the step wherein the diabetes care including the Individualized Action Plan", an "Individualized Support Program", and an "Individualized Treatment Scheme" addresses biomedical development of the patient pertaining to at least one of the following: healthy and controlled eating, weight, physical activity, support groups, blood glucose ($HbA_{1c}$), lipids, cholesterol, control, of hyperglycemia and hypoglycemia, smoking, positive energy/burnout prevention, coping with diabetes, and general health state.

Other Aspects

The following are directed to other aspects of this disclosure.

The systems, methods, and computer programs described in the claims are protected by an individualized Personal Access Code (PAC) which has the quality of a cryptomized access by using the data of a 'Socio-psychological Fingerprint':

using all the personal data of the existing health care system for the feasibility and good practical use within the respective medical system (varying from country to country);

using the data of the 'Individual Personal Profile' including the communication and interaction style and intimate personal data;

using the geographic situation and the GPS system as well as other electronic systems for protection of the intimate personal sphere;

thus cryptomizing the access in the highest possible degree of protection, offering strategic partnership with this example embodiment to the existing social networks which are altogether lacking this feature of intimacy on part of their clients and users.

All of the information to the users of the system, methods, and computer programs described in the claims will be unique and person-centered by means of the InterPersonal Style (IPS)© system which in the United States of America is developed specifically for diabetes management as 'I-D-E-A' (Introspective-Driver-Expressive-Amiable) system:

first analyzing the IPS style (for ILM application) or 'I-D-E-A' style (for diabetes management and chronic disease management) of the individual (patient);

then addressing all respective informations (reports for the diabetes patient in the respective style, i.e., short, concise, and fact-oriented for the 'Driver', i.e., differentiated, precise, and well elaborated with many facts and figures for the 'Introspective' with his analytic style) to be applied to all users (i.e., health care clients=patients and Health Care Professionals).

The system, methods, and computer programs described in the claims are describing the present situation and are using presently existing data and information.

In an additional example embodiment, the system, methods, and computer programs described in the claims are applied to a large sample of individuals, using anonymized data (e.g., 20 million insurance clients with their anonymized health care reports and medical history), protected for each one of the individuals by the cryptomized Personal Access Code (PAC), the 'Socio-personal Fingerprint';

thus elaborating with a representative sample of a very large group of individuals (e.g., 20 million of health care clients being insured in a country) from 10 years in the past (e.g., 2002-2012) the paradigms of health development, disease development, success or failure of prevention programs, medical support programs, treatment schemes, and medical therapies;

thereby evaluating the opportunities and risks of self-care, support programs, and treatment schemes calculating the economic consequences in terms of direct and indirect costs;

in order to elaborate predictive models with the help of the third generation and patent-protected segmental, so called 'activity-based' ILM Neural Network System' of Prof. Dr. Matthias Reuter;

which are applied and integrated into the ILM system, IHM system, and Diabetes Management system in order to predict the chances and risks of the individuals for the future ten years (e.g., diabetes patients as to risks of macrovascular diseases, cardio-attack, stroke, co-morbidity, multi-mordity, and showing the plausibility and chances for success of individualized self-care programs, individualized support program, and individualized treatment schemes with the combined economic effects on the individual and in total on the respective health care insurance or health care company, or the national health care system.

Many additional features, advantages and a fuller understanding of the example embodiment can be derived from the accompanying drawings and the detailed description that follows. It should be understood that the above Brief Description describes the example embodiment in broad terms while the following disclosure including Detailed Descriptions describes the example embodiment more narrowly and presents specific embodiments that should not be construed as necessary limitations of the broad example embodiment as defined in the claims.

BRIEF DESCRIPTION OF THE DRAWINGS

FIG. 6 is a schematic diagram of an example of the six key benefits of the diabetes management system of the present technology.

FIG. 8 is a schematic diagram of an example of the step collaborative care system (Example for IHM System) of the present technology.

FIG. 12 is a schematic diagram of an example of paradigm shift in individualized and collaborative health and diabetes management of the present technology.

FIG. 16 is a sample screen shot of a questionnaire example of self-assessment (GUIDE) of a diabetes Type 2 Patient showing an internet welcome page and information of the present technology.

FIG. 17 is a sample screen shot of a questionnaire example of Doctor's assessment (GUIDE) of the present technology.

FIG. 18 is a sample screen shot of a questionnaire example of assessment for Patient and Doctor with comments utilizing Patent's self-assessment and Reality Check by Doctor for collaborative care.

FIG. 19 is a sample screen shot of an example of a report from self-assessment.

FIG. 20 is a sample screen shot of an example of an additional report from self-assessment.

FIG. 21 is a sample screen shot of an example of an electronic survey Personal Portfolio Page (PPP) of the present technology.

FIG. 23 is a sample screen shot of an example of the portfolio system of the present technology.

FIG. 25 is a sample screen shot of an example for multiple chore choices, with Core 1 selected in the exemplary.

FIG. 26 is a sample screen shot of an example of the creation of the characteristic vector.

FIG. 28 is a sample screen shot of an example of a result of the categorization of success Factor 1.

FIG. 30 is a sample screen shot of an example of a result of a neural categorization according to a model of the present technology.

FIG. 32 is a sample screen shot of an example of a result of a NNS categorization according to a more sensitive model of individual analysis after group categorization showing a 'Need for Action'.

FIG. 34 is a sample screen shot of an example of a result of a NNS categorization with additional differentiation.

FIG. 40 is an exemplary structure of a neural net used for modeling a patient.

FIG. 41 is an exemplary principle structure of the appropriated hierarchical net structure for predicting the BG level of a patient.

DETAILED DESCRIPTION OF EMBODIMENTS OF THE PRESENT TECHNOLOGY

Figure 1:
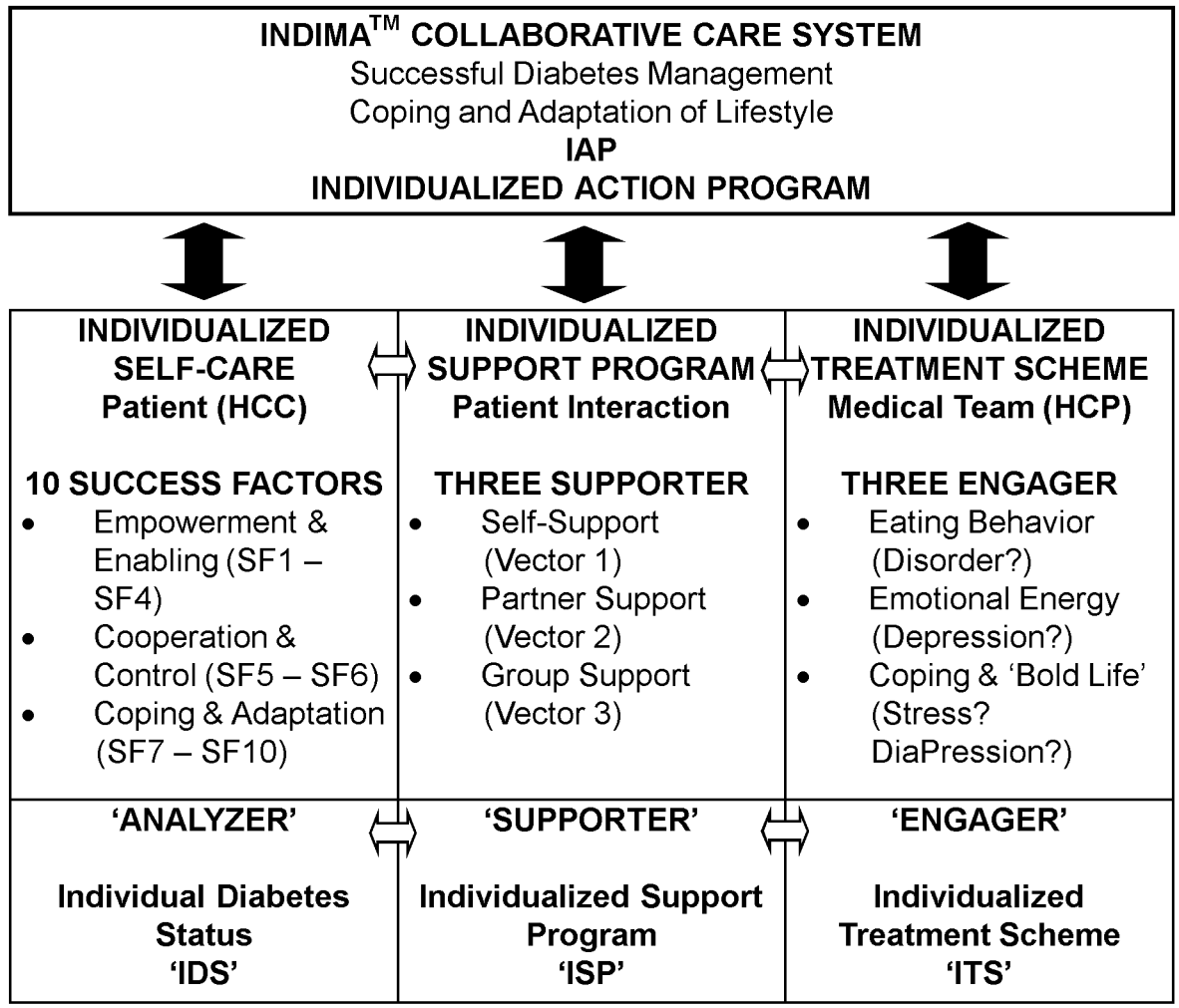
FIG. 1 is a schematic diagram of an example for a collaborative care system in diabetes management of the present technology.

Referring now to the drawings, and particularly to FIGS. 1-51, an embodiment of the present technology is shown and will be described.

FIG. 1 describes the InDiMa™ Apparatus which is used to create the 'Individualized Action Programs' (IAP) with the 'Individualized Self-Care' (ISC), with the 'Individualized Support Program' (ISP), and with the 'Individualized Treatment Scheme' (ITS) for the InDiMa™ Collaborative Care System.

An Example for an Area of Application: Individualized Finance Management

In order to reduce the complexity in the description of the example embodiment, the focus of the presentation is on the area of 'Individualized Health Management'. The three basic modules (S='Socio-marker', $P_E$='Perso-marker' and $P_S$='Psycho-marker') are identical for all 6 areas of the application (see Table 1 below).

Figure 2:
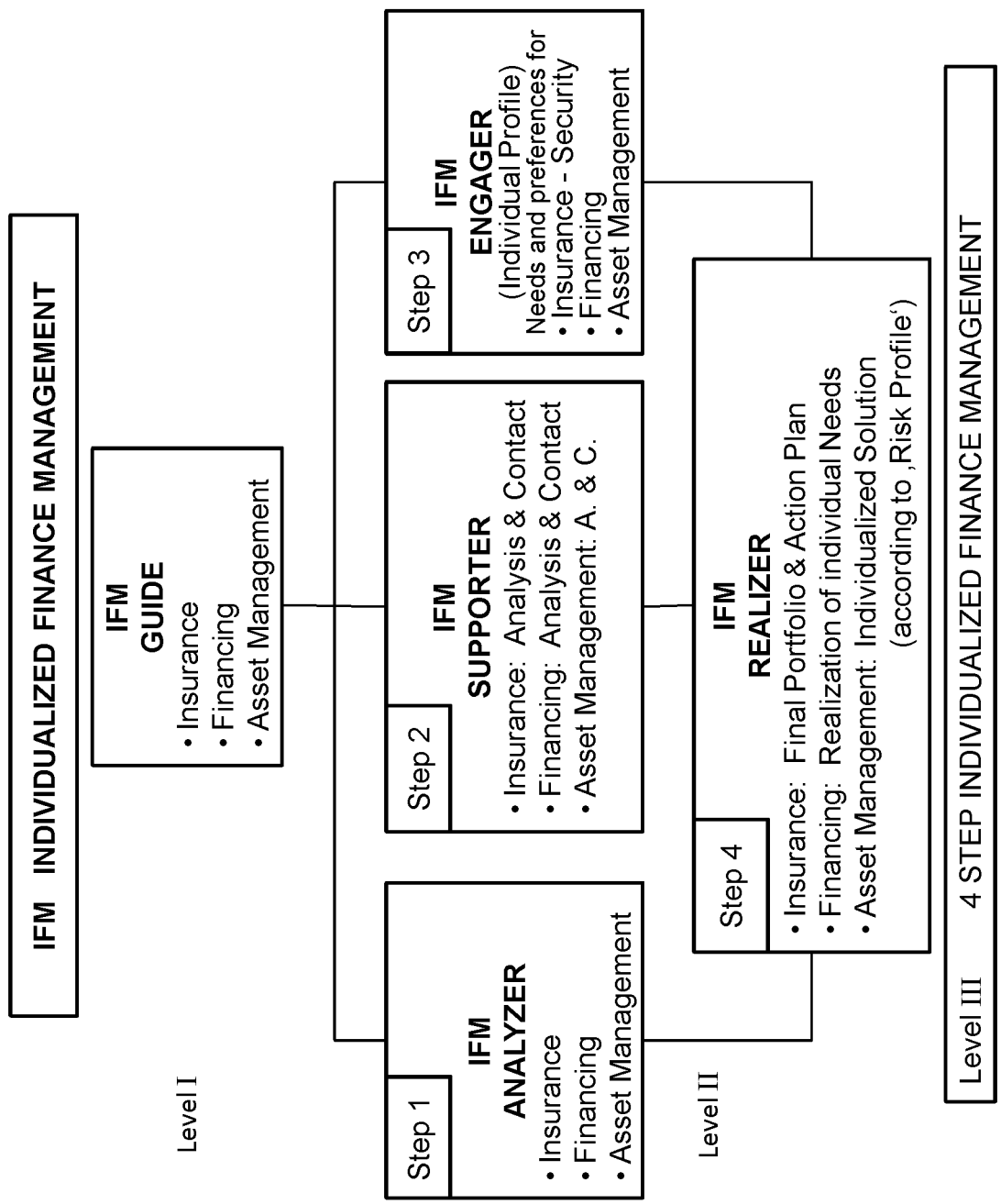
FIG. 2 is a schematic diagram of an example for another area of application of the Individualized Finance Management (IFM) of the present technology.

As an example for another area of application the 'individualized Finance Management' (IFM) is shown in FIG. 2.

Level I: IFM Guide

The client makes a self-assessment for the three aspects describing his financial management status:

Insurance

Financing

Asset Management

Level II: The IFM Subguides

Derived from the results of the IFM GUIDE, the client is then doing the self-assessment for the ANALYZER, consisting of Insurance, Financing and Asset Management SUPPORTER, consisting of Insurance (Analysis & Contact), Financing (Analysis & Contact) and Asset Management (Analysis & Contact)

ENGAGER, consisting of Needs and preferences for Insurance (& Security). Financing and Asset Management This leads to an 'Individualized Finance Management' Action Program (=REALIZER), which is developed by the client—in the role of a partner and not of an 'object' of 'manipulative treatment' by the banker or financial consultant. The client is fully empowered, has access to an 'Individualized Finance Management Information System', to a 'Social Network of Finance Management' and is associated with IFM consulting partners, focusing on 'Empowerment & Enabling' of the client (stage 1), on 'Cooperation & Consensus' (stage 2) and on 'Coping with financial challenges and Individualized Financial Management' (stage 3).

Brief Description of State Parameters, Action Parameters and Success Criteria

Figure 3:
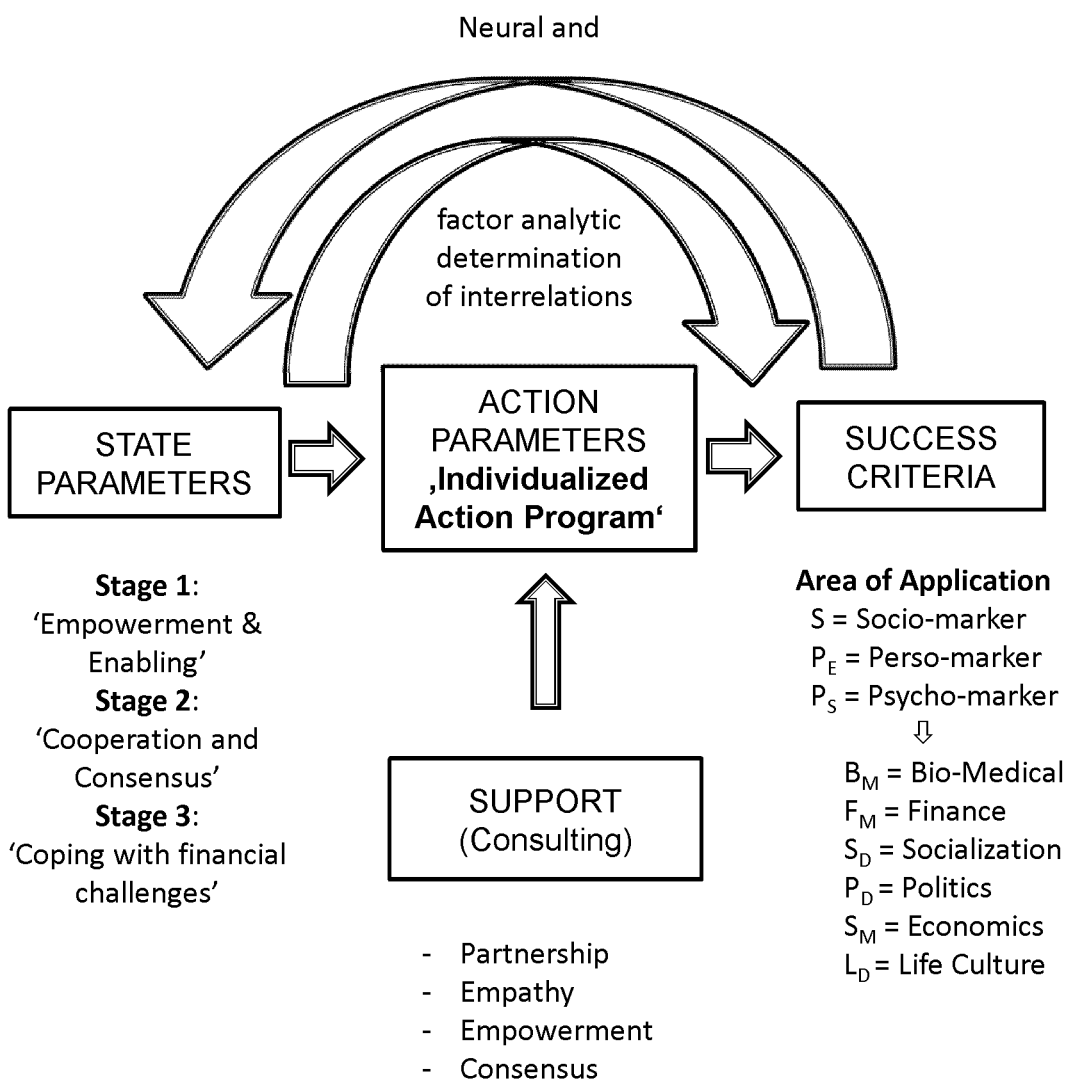
FIG. 3 is a schematic diagram of an example of the State Parameters, Action Parameters and Success Criteria of the present technology.
Figure 4:
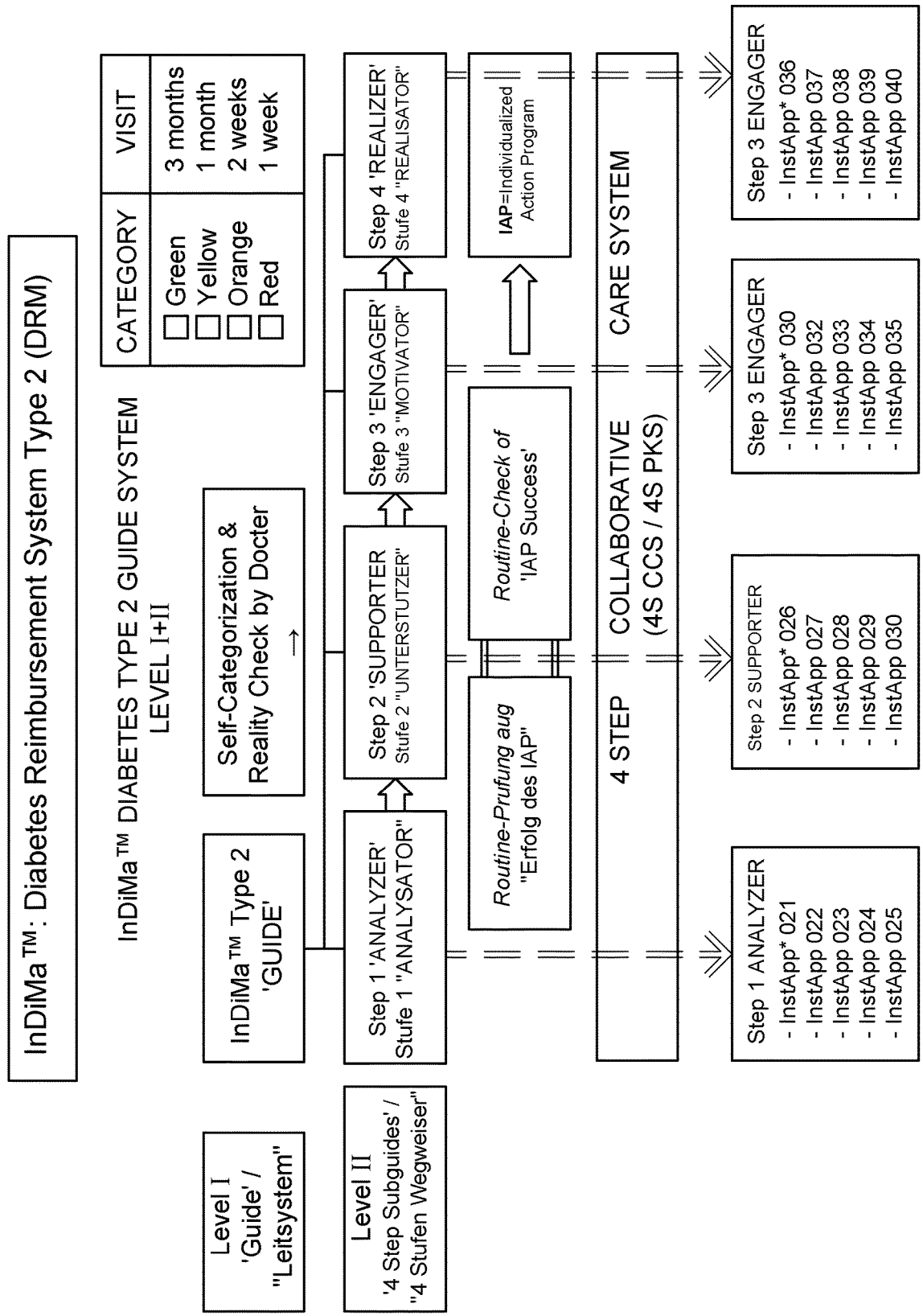
FIG. 4 is a schematic diagram of an example of the diabetes management system for cost-steering reimbursement management showing the 3 levels (I, II and III) of the Diabetes Reimbursement System of the present technology.
Figure 5:
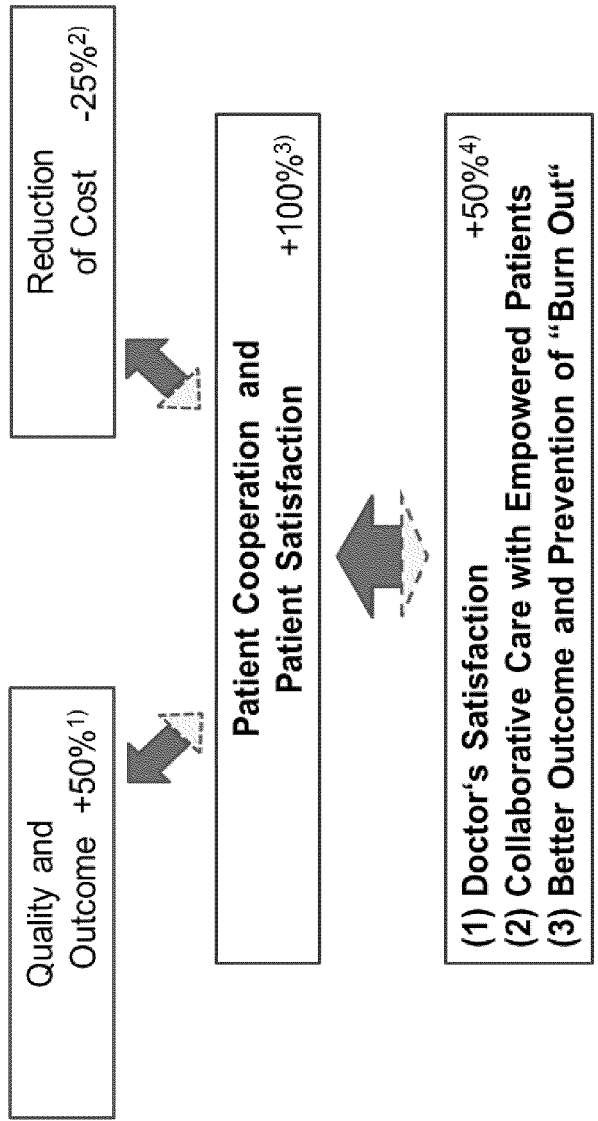
FIG. 5 is a schematic diagram of an example of the summary of benefits the diabetes management system of the present technology.
Figure 7:
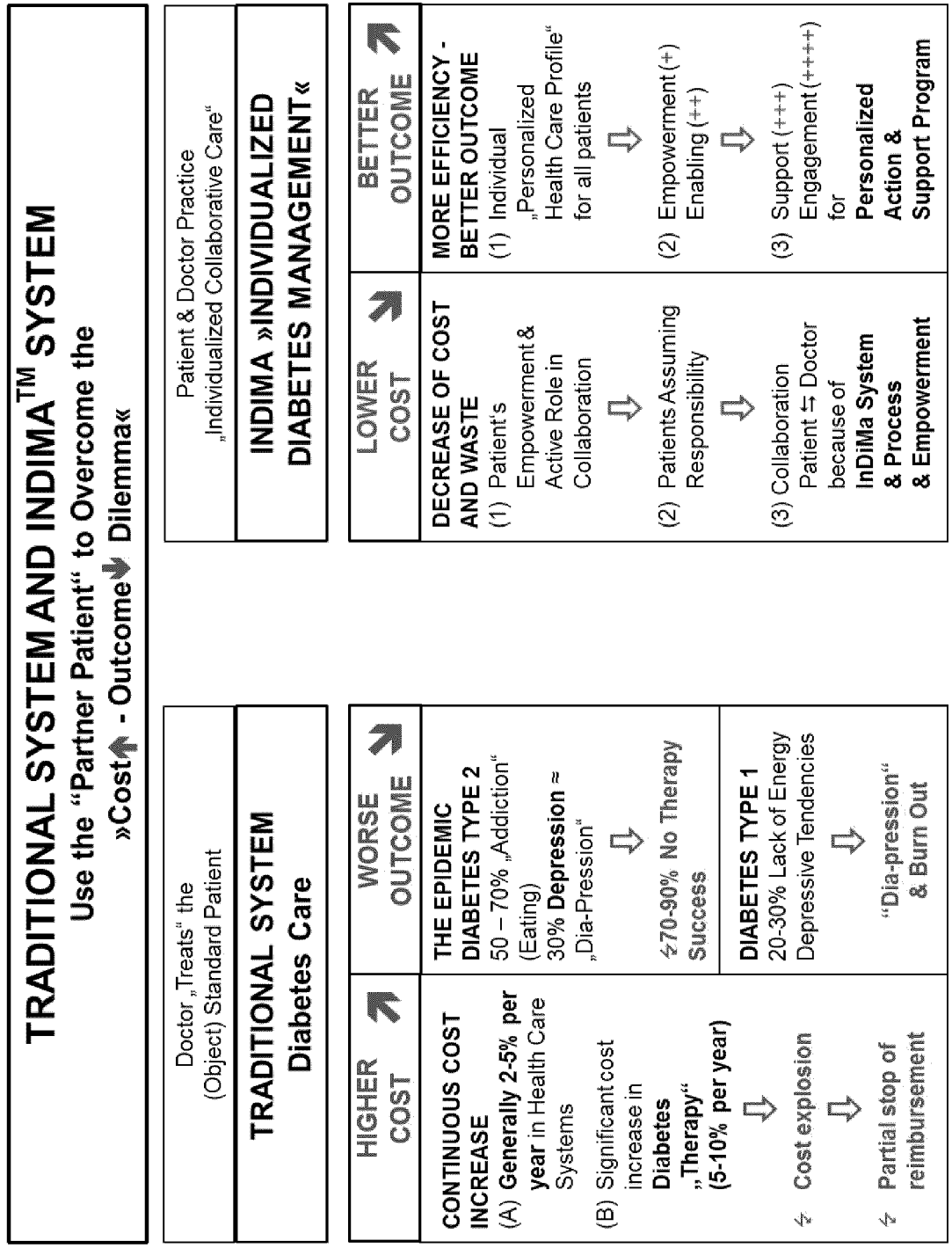
FIG. 7 is a schematic diagram of an example of advantages of the present technology for Individualized Health Management (IHM).
Figure 9:
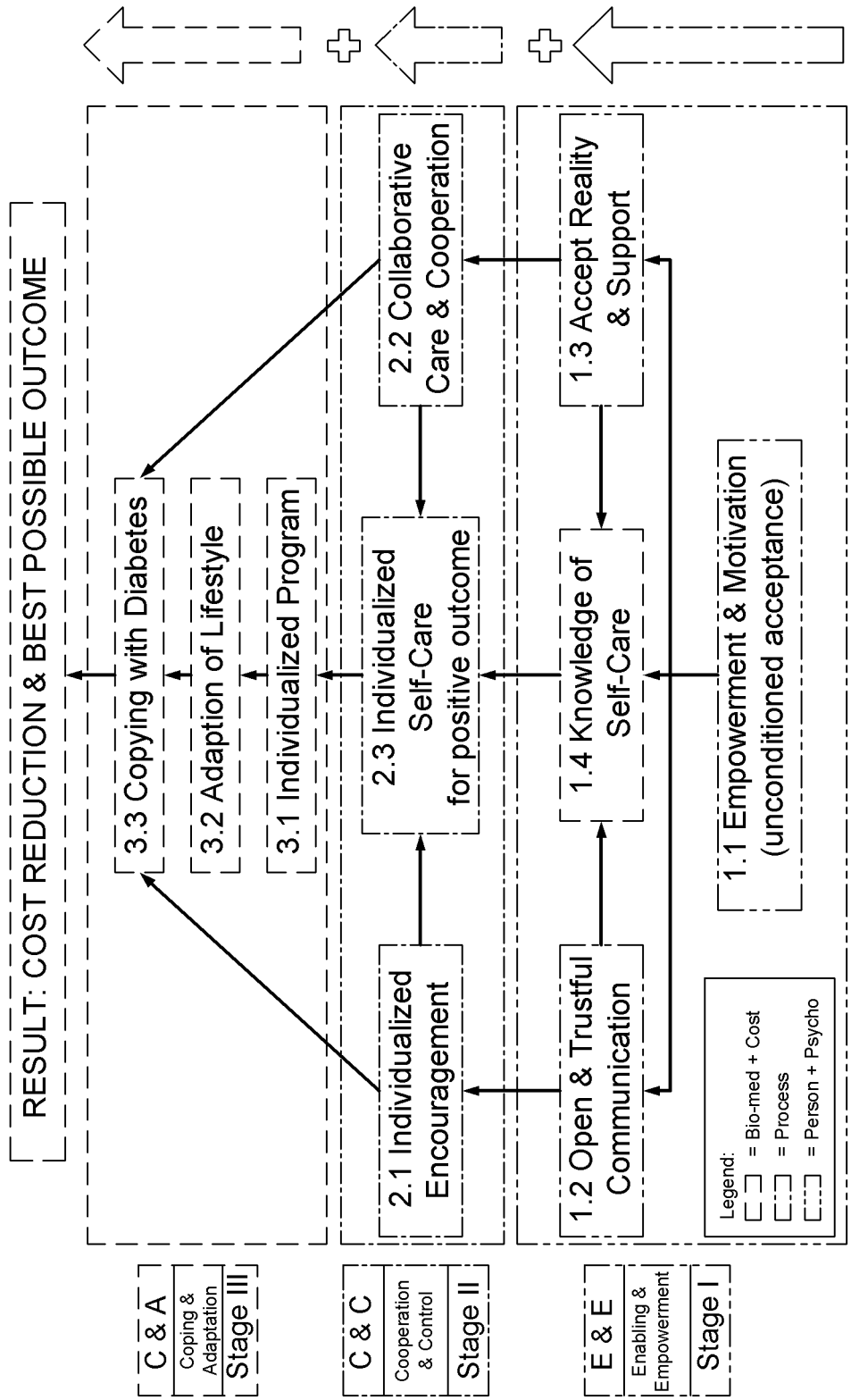
FIG. 9 is a schematic diagram of an example of three stages of the present technology model for individual diabetes management.

Referring to FIG. 3, all 6 areas of the ILM-Model are comprising state parameters, action parameters and are directed toward success criteria of socio-economic nature (S), of personal nature ($P_E$) and of psychological quality ($P_S$) with additional moderating parameters like support, consulting and information systems.

State Parameters

The 'state parameters' are describing the 'status of an individual' with regard to whatever is relevant for module 1 (=area of application):

Module 4 (S)=the 'Social Marker': describes the 'status of an individual' in respect to the social situation, social history, social environment and socio-economic status, social and financial status and challenges of the individual.

Module 3 ($P_E$)=the 'Perso Marker': describes the 'status of an individual' with regard to the personality traits, the characteristics of the person, the personal life history, the communication and interaction style, the preferences, customs and habits which the individual acquired during his lifespan up to the present day.

The communication and interactive style of an individual with others can be characterized by the IPS-System (Inter-Personal Style©) for the ILM areas or the 'I-D-E-A System', identifying the communication style and interaction style of the individual:

I='introspective'
D='Driver'
E='Expressive'
A='Analytic

Module 2 ($P_S$)=the Psycho-Marker': describing the 'status of an individual', the Individual Personal Profile (e.g., InstApp 001 and 021 of the InDiMa™ 4 Step Collaborative Care System) with the 'psychological make up' of the individual, energy level, psychological status, stress management, personal preferences, likes and dislikes.

Module 1: The Areas of Application

Module 1 is applying the ILM (Individualized Life Management) approach to the following six areas:

IHM=Individualized Health Management (Bio-Medical)
IFM=Individualized Finance Management (Finance)
ISD=Individualized Social Development (Socialization)
IPD=Individualized People Development (Politics)
ISM=Individualized Sales & Marketing (Economics)
ILD=Individualized Lifestyle & Design (Life Culture)

Action Parameters

The action parameters are related to the modules of the state parameters:

Module 4 (S)=the 'Social Marker': takes into account the social situation, social history, social environment and socio-economic status, social and financial needs and challenges of the individual for the 'Individualized Action Program' for 'Individualized Diabetes Care' (or the respective ILM area).

Module 3 ($P_E$)=the 'Perso Marker': individualizing the approach in the specific area and taking into account the personality traits, the characteristics of the person, the personal life history, the communication and interaction style, the preferences, customs and habits which the individual acquired during his lifespan up to the present day in order to develop an individualized, resourceful and realistic 'Individualized Action Program'.

Module 2 ($P_S$)=the 'Psycho-Marker': The individualization of the approach should be specific to the situation and to the person as well as to the psychological situation. Whatever the area of application is, the 'psychological profile' in this respect (whether it is an aspect of 'risk management in financial management, an aspect of ethical values of Social Development of the youngsters in the family, an aspect of personal, cultural and design preferences in selecting the furniture for an apartment or making the decision of a design of an outfit)—all this has to be considered and will be integrated into the Action Program in order to 'individualize' it according to Module 2.

Module 1: The Areas of Application

Whatever the existing situation (state parameters) is and whatever the success criteria or goals of the individuals are: The action parameter have to take this into account and have to create a solution which is integrating a realistic assessment of the existing social and economic situation in a specific environment at a given time ('Reality-Check'), taking into consideration the resources of the individual (vector 1) with partner, family and friends (vector 2) and the resources that an individual can make use of in his environment (vector 3) in order to establish realistic and 'Individualized Action Programs' with a high probability of success.

Success Criteria and Success Factors

There should be an integration of reality (what is possible by considering the situation and the given resources).

The 'subjective situation' and the individual resources of the person (patient/client) should be taken into account.

The resource management, using support, consulting, individual resources, resources in the near social environment and the community are also to be considered in order to develop a success-related (goal-directed) and realistic scenario.

'Individualized Actions Programs' Comprising the Sets of
  State parameters
  Action parameters
  Success Criteria or objectives and goals based upon a creative, but also realistic resource management are appropriate in order to reach the optimum for the 'individualized Action Program' in the respective area.

Part I IHM and 'InDiMa™ Apparatus': System, Method, and Computer Program Product for Individualized Collaborative Health Care With reference to FIGS. 4-10, the example embodiment relates to a system, method, and computer program product for individualized and collaborative health care involving a plurality of individuals, using groups of state parameters that define a state of each individual, and using groups of action parameters that define (self-)treatment options and/or behavior support options of the InDiMa™ therapy and support system, targeted at an individual within said plurality of individuals.

1. IHM and 'InDiMa™' for Today's 'Health Care Systems'

In recent years, collaborative health care has become an issue of increasing importance in many regions of the world, particularly in highly developed countries such as Northern America (USA, Canada) and Europe with aging populations and (nutrition and lifestyle related physical activity) effects on individuals' health.

1.0 The System Method and Computer Program for 'Individualized Life Management' and 'Individualized Health Management'

The example embodiment to be described applies to all relevant aspects of Life Management and to the Six Areas of 'Individualized Life Management' (see Table 1)

TABLE 1

| 4 Modules | ILM = Individualized Life Management Area |
|---|---|
| (1) $S \Rightarrow P_E \Rightarrow P_S \Rightarrow B_M$: | IHM = Individualized Health Management (Bio-Medical) |
| (2) $S \Rightarrow P_E \Rightarrow P_S \Rightarrow F_M$: | IFM = individualized Finance Management (Finance) |
| (3) $S \Rightarrow P_E \Rightarrow P_S \Rightarrow S_D$: | ISD = Individualized Social Development (Socialization) |

TABLE 1-continued

| 4 Modules | ILM = Individualized Life Management | Area |
|---|---|---|
| (4) S ⇨ $P_E$ ⇨ $P_S$ ⇨ $P_D$: | IPD = Individualized People Development | (Politics) |
| (5) S ⇨ $P_E$ ⇨ $P_S$ ⇨ $S_M$: | ISM = Individualized Sales & Marketing | (Economics) |
| (6) S ⇨ $P_E$ ⇨ $P_S$ ⇨ $L_D$: | ILD = Individualized Lifestyle & Design | (Life Culture) |

In the following we are focusing on the Individualized Health Management and especially on the 'InDiMa™' Model for 'Individualized Diabetes Management' which applies also for patients with other chronic diseases, acute disease management, and 'Individualized Wellness & Prevention' of the IHM Model for 'Individualized Health Management'.

To show the practical relevance and the benefits of the example embodiment with system, method and computer program of the example embodiment, we are focusing on chronic diseases and especially on 'Individualized Diabetes Management' ('InDiMa™'), the 'Individualized Health Management' System of the 'InDiMa™ Apparatus'.

1.1 Diabetes and Lifestyle

It is well-known that some widely spread and frequently occurring chronic diseases (especially diabetes) are closely-related to Western lifestyle with unhealthy nutrition patterns. Overnutrition, combined with sedentary lifestyle, typically leads to overweight and obesity which is likely to cause acute macrovascular problems and threats (macrovascular diseases like diabetes, cardio-attack, and stroke) to a an individual's health or even life.

1.2 No Adequate ('Individualized' and 'Collaborative') Health Care for Diabetes and Other Chronic Diseases Depression, combined with diabetes, also called "depres-sion", stress and burn-out, often combined with psychosomatic diseases, gastro-intestinal diseases, chronic orthopedic diseases (head, shoulders, back), chronic pain-related diseases and all other chronic diseases need to be understood and treated in a holistic approach. This means to incorporate the body (bio-medical aspects), the soul (psychological aspects), the personality (character and genetic disposition), and the social history, socio-economic status and social environment of the patient(s).

1.3 Increasing Diabetes-Related and Health Care-Related Economic Burden

As a result, these individuals' quality of life—in the case of diabetes type 2—is severely impaired both physically and mentally. In consequence, public health systems of these highly developed countries are exposed to an increasing economic, health-related, and 'productivity' burden.

An example for these lifestyle-related problems: 66% of the US population is "overweight" (December 2010, US Today) and 34% are diagnosed as "obese" (Body Mass Index=BMI over 30).

1.4 Rationally Based Bio-Medical Health Care is not Sufficient

With reference to FIGS. 11-14, at present, the health care systems in many highly developed countries provide a wide range of measures to address these individuals' health problems. Unfortunately, most medical treatments are based merely or primarily on an individual's easily measurable biological and medical (physiological) condition without taking into account that individual's psychological (mental and emotional) condition, the patient's personality (character and genetic factors) and the social factors (socio-economic environment).

2. The B-P-P-S Model for 'InDiMa™' Individualized Diabetes Management

Table 2 shows the Four Factor B-P-P-S Model which also applies to 5 other areas of the 'ILM' (Individualized Life Management) System.

The B-P-P-S Model for 'Individualized Health Management' and for the chronic disease management comprises the following four basic factors:

TABLE 2

| "Bio-Medical" "B" | (1) the treated individual's bio-medical and physiological condition |
|---|---|
| "Psycho" "P" | (2) the individual's psychological condition |
| "Perso" "P" | (3) the individual's personality structure, genetic factors, and behavior patterns and |
| "Socio" "S" | (4) the social history and social (lifestyle) environment of the individual |

The individual's bio-medical and physiological condition (B) is the combined result of the individual's psychological, personal, and genetic as well as social and socio-economic factors: the 'moderating modules' P-P-S(see Table 2)

Module 'Psycho' ($P_S$): The individual's psychological condition ($P_S$) is the dynamic aspect of a personality. Module 'Perso' ($P_E$): The psychological status of a person is intertwined with the individual's personality traits ("character") and genetic factors ($P_E$). Module 'Socio' (S): The socio-economic, genetic, and social environment factors within the patient's life (S) are the basis for the personal development ($P_E$) and influence the psychological status ($P_S$).

2.1 The Interrelations of the Four Factors B-P-P-S of the IHM- and InDiMa™-Model It has been empirically proven that an individual's psychological condition is part of the soul ("psyche")-body ("soma") interrelation in the course of individualized and collaborative health care. The personality structure, the (during the former life acquired) behavior patterns, and the psychological state of an individual have both direct influence (e.g., psychosomatic medicine, placebo effect) and indirect influence (via modified patient behavior, i.e., treatment adherence and compliance) on the individual's physiological and medical ("Bio-Med") condition.

As a result, the existing purely "bio-medically oriented" health care systems are significantly less successful than they potentially could be.

2.2 Improvement Needs in InDiMa™ Diabetes Management (as Example): Need for 'InDiMa™' Apparatus A striking example is the diabetes therapy: There is a significant need for improvement in the quality and efficiency of health care systems in general and diabetes care (especially for type 2) in specific.

2.3 Objectives of the InDiMa™ 'Individualized Health Management (IHM)'

Therefore, it is an objective of the present example embodiment to improve the quality and efficiency of such health care systems, reducing the costs significantly through the active integration of the patient.

3. The Present Example Embodiment 'IHM' and 'InDima™' Apparatus—a System for Individualized and Collaborative Health Care'

The present example embodiment provides a system for individualized and collaborative health care involving a plurality of individuals, using groups of state parameters for defining a state of each individual, and using groups of action parameters for defining (self-)treatment options and/ or behavior support options of the InDiMa™ therapy and support system, targeted at an individual within said plurality of individuals.

3.1 Functioning of the InDiMa™-Apparatus (Example for IHM Apparatus)

The InDiMa™ Apparatus system comprises a data processor means adapted for processing input data, which are based on said groups of state parameters, into output data, which are the basis for said groups of action (adaptation, change, and treatment) parameters, using defined relationships/options for action between groups of state parameters and groups of action (adaptation, treatment, and support) parameters; a data storage means adapted for storing said groups of state parameters, said groups of "action" (adaptation, treatment, and support) parameters and said defined relationships/options for action between groups of state parameters and groups of "action" parameters; characterized in that the system further comprises a data communication system/platform adapted for communicating state parameters selected from said groups of state parameters and/or "action" parameters selected from said groups of "action" parameters among said plurality of individuals.

3.2 Communication Among 'InDima™' Categorized Patients (IHM Apparatus)

Due to the data communication system, the health care system of the present example embodiment (InDiMa™ Apparatus system) enables individuals, i.e. patients whose health is (self-)monitored or who undergo medical treatment and support with lifestyle adaptation, to exchange personal health-related and/or personal treatment-related information. Thus, the InDiMa™ Apparatus system enables not only patients and health care professionals (medical doctors, nurse educators, and nurses) to communicate in a higher quality and more efficiency via the InDiMa™ system, but also patients to communicate with each other.

This possibility for communication and information exchange provides patients with the benefits of a (self-) support group with the extra benefit of having relevant information readily available to be exchanged among the patients.

3.3 Individualized Empowerment and Enabling of Patients (Phase 1 in IHM Model)

Using this relevant information in the form of groups of state parameters defining a state of each patient including this patient's biological/medical (physiological) condition as well as this patient's psychological (mental and emotional) condition, personality and genetic factors as well as social and socio-economic factors and in the form of groups of "action" (treatment and support) parameters defining treatment and behavior support options for each patient within the plurality of patients puts each patient in an empowered, more self-determined, and strengthened psychological (mental and emotional) position. Patients aware of other patients' health conditions and life situations tend to develop significant improvements in treatment adherence and lifestyle change with significantly improved behavior patterns and compliance with behavior changes as offered by the treatment options and behavior support options offered to the patients.

Figure 15:
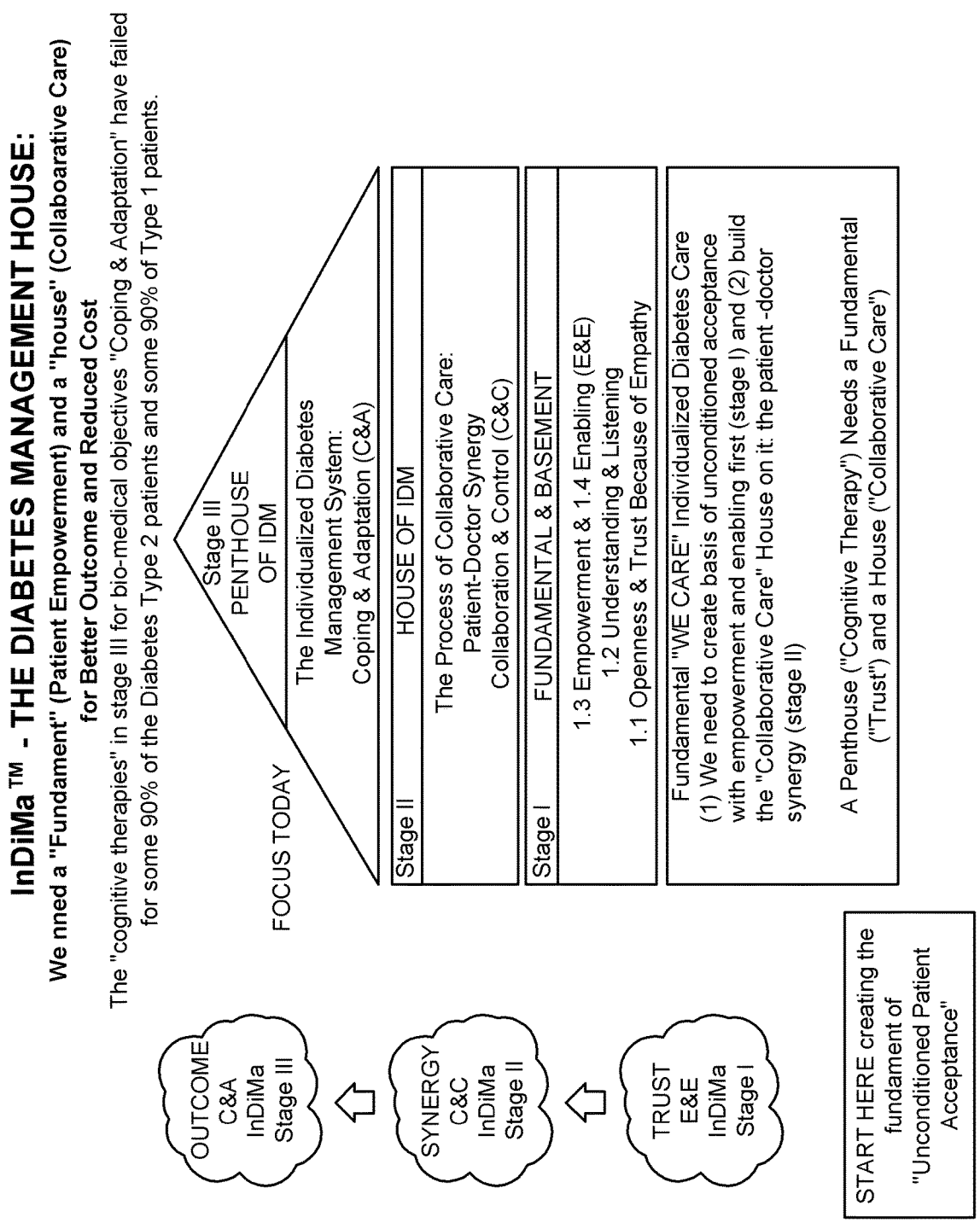
FIG. 15 is a schematic diagram of an example of three phases of development for IHM model.

3.4 the Three Phases of Development (Example for IHM Model See FIG. 15)

4. Application of the InDiMa™-Apparatus

In the InDiMa™ Apparatus health care system of the present example embodiment, the data processor means may comprise an adaptive structure where said defined relationships and options for action (treatment and support) between groups are redefined/updated using empirical pairs of action (treatment and support) parameter groups and state parameter (patient psychometry and patient-doctor communication) groups.

4.1 Self-Organizing Maps ('SOM's) of a 'Learning System'

Due to this adaptive structure or dynamic knowledge base with—for example but not limited to—"Self-Organizing Masks" (SOM's) of the InDiMa™ Apparatus, the InDiMa™ Apparatus health care system of the present example embodiment is a "Learning System" which is constantly updated using the empirical pairs of action parameter groups and state parameter groups of patients who most recently joined the InDiMa™ Apparatus health care system of the present example embodiment.

Preferably, the adaptive structure (lifestyle adaptation for example, but also treatment and support options) is selected from the group consisting of patient self-assessment as basis, from expert systems, fuzzy logic, neuronal networks, genetic and/or evolutionary algorithms and combinations thereof.

4.2 Adaptive Structures and Predictive Models of the InDima™ Apparatus

Adaptive structures of this kind are updated automatically by including empirical pairs of state parameter groups (patient self-assessment) and corresponding action (treatment and support) parameter groups who most recently joined the InDiMa™ Apparatus health care system of the present example embodiment. Knowledge-based software structures with explicit rules such as expert systems, fuzzy logic, and combinations thereof are usable, when the number of individuals having joined the InDiMa™ Apparatus health care system of the present example embodiment is rather limited. Non-knowledge-based software structures such as neuronal networks, genetic and/or evolutionary algorithms and combinations thereof are usable, when the number of individuals having joined the health care system of the present example embodiment is very large: typically more than 1000 individuals and more than 10,000 individuals; finally using data banks with millions of patients for Neuronal Network System (NNS) analyses. When stating these numbers, it should be noted that an individual application of the InDiMa™ Apparatus health care system of the present example embodiment normally deals with only one type of disease and a population of individuals suffering in different "individual patterns and degrees" from this disease.

5. InDiMa™ Apparatus as a Web-Based System

In a specific embodiment, the InDiMa™ Apparatus health care system of the example embodiment is a web-based system.

As a web-based system, the health care system of the present example embodiment may be accessed via a computer network such as the internet or an intranet, i.e. a computer network linking individual hospitals, health care professionals' practices or clinics, offices of support groups and patients' homes and even health care professionals' and patients' mobile communication devices.

5.1 The Groups of State Parameters of the InDiMa™ Apparatus

The groups of state parameters may be selected from the group consisting of biomedical (physiological), psychological, personal, and social (socio-economic) ("BPPS") characteristics/attributes of health care clients. Preferably, all of these characteristics/attributes are selected for constructing the groups of state parameters.

5.2 The Holistic Approach of the Innovative Neural Network SYSTEM (INNS)

This allows each client/patient having joined the health care system of the present example embodiment to be viewed in its entirety (holistic approach). Rather than looking at an individual patient in an isolated manner, i.e. only from the "medical/physiological angle", the health care system of the present example embodiment looks at the individual patient "from all angles", i.e. considering various aspects that are prone to influence that individual patient's reaction when faced with treatment options and/or change-of-behavior options.

5.3 'InDiMa™' Client-Specific State Parameters

Preferably, a health care client-specific state parameter group is based on assessment of a health care client using a Questionnaire.
The 10 'Guide'-Questions (see Table 3)

patients' mobile (wireless) communication devices (templates, including for instance iPhone technology).

FIG. 21 is a Screenshot of the electronic Survey (Personal Portfolio Page)

5.4 'InDima™' Groups of State Parameters

In view of the foregoing, the present example embodiment also provides a method for individualized and cooperative health care involving a plurality of individuals, using groups of state parameters that define a state of each individual, and using groups of action parameters that define treatment options and/or behavior options targeted at an individual within said plurality of individuals, the method comprising: processing input data, which are based on said groups of state parameters, into output data, which are the basis for said groups of action parameters, using defined relationships/assignments between groups of state parameters and groups of action parameters; and storing said groups of state parameters, said groups of action parameters and said defined relationships/assignments between groups of state parameters and groups of action parameters; characterized by communicating state parameters selected from said groups of state parameters and/or action parameters selected from said groups of action parameters among said plurality of individuals.

TABLE 3

| "1" = okay - good, "2" = improve, "3" = must change, "4" = urgent action | |
|---|---|
| 1) My overall physical and psychological health: | "1" "2" "3" "4" "NA" |
| 2) Positive energy and motivation for coping with diabetes (vs. lack of energy, depressive tendencies and burn out): | "1" "2" "3" "4" "NA" |
| 3) My blood pressure and fitness (healthy eating and weight control): | "1" "2" "3" "4" "NA" |
| 4) My cholesterol, lipids and cardiovascular status (physical activity and no smoking): | "1" "2" "3" "4" "NA" |
| 5) My blood glucose control (HbA1c long-term value; avoiding glucose 'hypos' and 'hypers'): | "1" "2" "3" "4" "NA" |

| "1" = okay - good (sufficient), "2" = need more (not enough), "3" = definitely needed (too little), "4" = urgently needed (no support) | |
|---|---|
| 6) The support for a healthy lifestyle with my diabetes in my social environment (healthy eating, physical activity, no smoking): | "1" "2" "3" "4" "NA" |
| 7) My acceptance of guidance and support by my doctor, cooperation with the medical team and readiness to act consequently: | "1" "2" "3" "4" "NA" |

| "1" = under control (normal weight), "2" = mostly controlled (some overweight), "3" = often uncontrolled (definite overweight), "4" = no control (obesity - adiposity) | |
|---|---|
| 8) Eating behavior (weight control, healthy eating and physical activity): | "1" "2" "3" "4" "NA" |

| "1" = okay - good, "2" = improve, "3" = must change, "4" = urgent action | |
|---|---|
| 9) My knowledge about self-care, my therapy adherence and quality of self-care | "1" "2" "3" "4" "NA" |
| 10) My coping with diabetes, adaptation of lifestyle with physical activity and quality of life in total: | "1" "2" "3" "4" "NA" |

Figure 16:
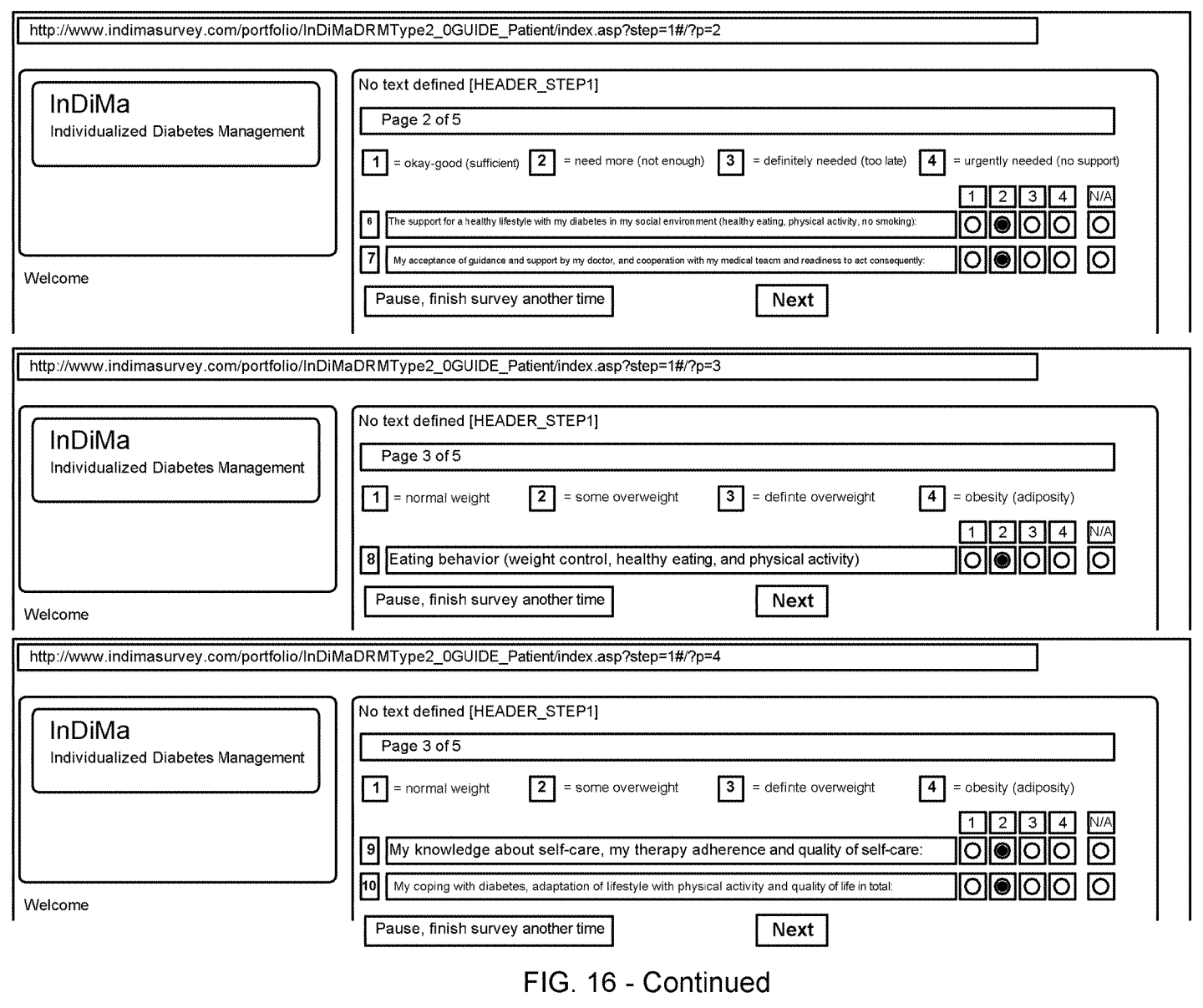

Self-Assessment Barnie Miller (see FIG. 16)

Such assessment by questionnaire provides a standardized collection of information about the health care client. This standardized collection of information can easily be transferred into groups of state parameter values for defining a state of each individual, see FIGS. 19-20.

Preferably, the questionnaire is a web-based questionnaire which may be sent to a health care client via a computer network such as the internet or an intranet, i.e. a computer network linking individual hospitals, health care professionals' practices or clinics, offices of support groups and patients' homes and even health care professionals' and

5.5 InDima™ Information and Concepts for Support Groups

Due to the data communication step, the health care method of the present example embodiment enables individuals to exchange personal health-related and/or personal treatment-related information. The method may include communication of patients with each other. This possibility for communication and information exchange provides patients with the benefits of a (self-)support group with the extra benefit of having relevant information readily available to be exchanged among the patients. Thus, each patient is strengthened psychologically (mentally and emotionally) and is prone to significantly improve his discipline and compliance with respect to the treatment and/or behavior changes defined by the treatment options and/or behavior options specifically targeted at him.

5.6 Action Parameter and State Parameter Groups of Patients

The defined relationships/assignments between groups may be redefined/updated using empirical pairs of action parameter groups and state parameter groups of patients who most recently joined the health care system of the present example embodiment. Each of the new patients whose patient information, i.e. state parameter values or patient profile, is added to the system and whose associated treatment information, i.e. action parameter values or treatment profile, is added to the system will broaden the empirical base of the system. These empirical pairs of state parameter values and their associated action parameter values are preferably evaluated by quantifying the success of the treatment and/or behavior changes for the patient they belong to. Based on this quantified success, an evaluated and weighted empirical pair, composed of state parameters with their values and action parameters with their values, is taken into consideration for modifying/updating the previously existing relationships/assignments between state and action parameter groups.

Preferably, the above groups of state parameters are selected from the group consisting of biomedical (physiological), psychological, personal, and socio-economic ("BPPS") characteristics/attributes of health care clients.

Preferably, a health care client-specific state parameter group is determined by assessing this health care client using a Questionnaire. This questionnaire may be a traditional one in paper format.

5.7 InDima™-Driven 'Collaborative Care' of Health Care Client (HCC) and Health Care Professional (HCP)

In a specific embodiment, the method of the example embodiment comprises assessing a health care client's specific state parameter group, i.e. the value for each state parameter in this group, using two assessment processes that are at least partially independent of each other. Typically, a first assessment process involves the health care client (HCC) only, i.e. the HCC answers the questions of the questionnaire all by himself, and a second assessment process involves the health care professional (HCP) only, i.e. the HCP answers the questions of the questionnaire all by himself. As a first alternative, the second assessment process may involve the HCC and the HCP, i.e. they answer the questions of the questionnaire again together. As a second alternative, a third assessment process may involve the HCC and the HCP. There may be even more alternatives for additional/complementary assessment processes involving persons other than the HCC or the HCP such as the HCC's family members or friends.

Once these different assessment processes of a specific HCC have been carried out, the results of these assessment processes are compared.

5.8 InDima™ Categorization of Health Care Clients—'Need for Action'

The results of these comparisons again provide significant information for the categorization of each HCC, in particular with respect to the psychological, personal and socio-economic characteristics/attributes of this HCC and the consequent 'need for action'.

More preferably, when the health care system of the example embodiment is a web-based system, the Questionnaire is provided in email format to an authorized health care client's email address. The authorized health care client joins the health care system of the present example embodiment by answering multiple-choice questions, selecting statements, using rating scales and qualitative assessments etc. in the questionnaire. Based on this information provided by the client, each parameter in the group of state parameters is assigned a marker/value for this specific client. Based on this client-specific state parameter group and on the defined relationships/assignments between groups of state parameters and groups of action parameters, a client-specific action parameter group is generated where each parameter in the group is assigned a marker/value for this specific client: e.g., categorizing the 'need for action' options for the 'Individualized Action Program' for the individual patient.

5.9 Feedback and Giving Options by the System

The authorized health care client whose individual state is now defined and included in the health care system of the present example embodiment may be given feedback by the system disclosing to him the treatment options and/or behavior options based on the system-determined action parameter markers/values. In addition, this authorized health care client may be given feedback by the system disclosing information about health care professionals for him to choose for his future treatment.

5.10 Repeated Determination of Client-Specific Parameter Groups (E.G., Health Care Visit Documentation)

Preferably, the health care client-specific state parameter group is repeatedly determined throughout this health care client's affiliation to the plurality of individuals of the health care system of the present example embodiment.

5.11 Communication and "Collaborative Care" Between HCC and HCP

Thus, this health care client will benefit from the accumulated information and updated defined relationships/assignments between groups of state parameters and groups of action parameters in the system gathered from additional authorized health care clients that joined the health care system of the present example embodiment after him. In other words, once each individual health care client has joined the health care system of the present example embodiment, he will benefit from his own and all other health care clients' contribution to the knowledge/intelligence of the system.

In a specific example embodiment, communication and information exchange is made available among individuals belonging to a first subset of the plurality of individuals including health care clients (HCC); among individuals belonging to a second subset of the plurality of individuals including health care professionals (HCP); and between individuals belonging to the first subset (HCC) and individuals belonging to the second subset (HCP).

5.12 Patient to Patient Communication

Thus, the system and method of the present example embodiment enable individual health care clients/patients to enter into direct contact and communication with each other. Such communication within a group sharing some common problem(s) has been shown to help alleviate an individual's fears and frustration about his or her health situation by making that situation more acceptable ("I am not the only one having this problem") and increasing the individual's motivation to actively contribute to an improvement of his or her situation. It has been shown that individuals in such a setting are more disciplined which makes them significantly more compliant throughout their medical treatment and encouraged behavior modifications. In other words, the system and method of the present example embodiment integrates support group functionalities with all the known benefits of a support group.

5.13 Communication from HCPS to HCPS

Similarly, the system and method of the present example embodiment enable individual health care professionals/medical doctors to enter into direct contact and communication with each other. Such communication among experts may be necessary for very difficult cases. Thus, the health care professionals affiliated to the system and method of the example embodiment are supported by the case-specific or client-specific action parameter values defining options for treating a that specific client and/or modifying that client's behavior.

5.14 Cross-Communication Between HCC(S) and HCP(S)

Also, the system and method of the present example embodiment enable cross-communication between health care clients on the one hand and health care professionals on the other hand. This provides additional transparency and some competition both for health care clients and for health care professionals. Increased transparency and competition among health care clients means that they tend to compete for treatment success which translates into improved compliance during the treatment received. Increased transparency and competition among health care professionals means that they tend to compete for treatment success which translates into adoption of best (client-specific) practices for the treatment provided. In other words, cooperation between health care clients and health care professionals towards a common goal (treatment success) is improved.

5.15 Sharing Information and Empirical Results of Treatment Options

Preferably, the defined relationships/assignments between action parameter groups and state parameter groups are made available for communication and information exchange among the plurality of individuals including health care clients/patients and among the plurality of individuals including health care professionals/medical doctors.

This allows every health care client to identify where he and is health situation and the associated treatment options are positioned within the overall spectrum of health care clients, health situations and treatment options.

5.16 Identification of Best Possible 'Individualized (Health) Treatment'

Similarly, this allows every health care professional to identify his clients' health situations, the associated treatment options and to compare them with the overall spectrum of health care clients, health situations and treatment options.

Preferably, individuals of the above plurality of individuals are categorized into different categories of individuals based on their respective state parameter groups and corresponding action parameter groups (e.g., the 'need for action' priorities).

5.17 Patient Category-Specific Treatment and Predictive Models

As mentioned above, the number of individuals having joined a health care system of the present example embodiment is very large, typically more than 1,000 individuals, more than 10,000 individuals, and finally millions of patients in a global setting can be reached. It should be noted that an individual health care system of the present example embodiment typically covers only one type of disease and individuals suffering in individual patterns and to different degrees from the respective disease. Given these numbers of individuals and a finite spectrum of overall individual health situations defined by specific state parameter combinations, a representative number of health care client (HCC) categories can be defined with each category including a reasonable number of individual health care clients. This guarantees that all HCC individuals in each HCC category are similar enough to undergo one category-specific treatment on the one hand and that each HCC category includes a large enough number of HCC individuals to be attractive enough for intra-category communication and information exchange among HCC.

Also predictive models for 'individualized treatment options' and related outcome probabilities linked to Cost-benefit predictions can be developed by the INNS InDiMa™-Apparatus.

6. 'Collaborative Care' in the IHM System: Example of the InDima™ System

In summary, the following characteristics are describing the 'Individualized Health Management' System in general and the InDiMa™ System for 'Individualized Diabetes Management' with the 'Collaborative Care' approach in specific:

Four Characteristics of InDima™ Collaborative Care:

1. The health care system and health care method of the present example embodiment primarily empower and enable the health care clients (HCC) affiliated to the system with respect to Health Care Professionals and also other players and stakeholders in the health care industry (step 1); the health care system of the example embodiment improves cooperation and control (step 2); finally the said health care system creates the basis for coping with a disease, in this case of coping with diabetes and adaptation of lifestyle (C+A; phase 3).

2. Being provided the possibility to communicate with each other within the HCC subset of individuals, the HCC can exchange empirical evaluating information about health care professionals (HCP), information about disease management and treatment results including medication/pharmaceuticals and health care support devices, but also about empirical results of treatment options, support groups and medical therapy groups.

3. The effect of this direct personal information exchange combined with the accumulated knowledge/intelligence of the system providing HCC-specific or HCC category-specific action parameter values to HCP and HCC and combined with the competition mechanisms within the HCP subset of individuals and within the HCC subset of individuals, as discussed above, generates a powerful evolutionary mechanism towards best practices which is transparent and traceable along throughout its evolution.

4. This empowerment of health care clients/patients who used to play the part of mostly passive "objects" within existing health care systems will "promote" these health care clients/patients to more active "subjects" and partners in the 'Collaborative Care' System within the health care system of the present example embodiment, creating a synergistic unit of HCC and HCP.

In the detailed description in Part II, elements of an individualized disease management (Indima™) system and method, in particular with respect to diabetes care, are described as a special case of the 'Individualized Health Management' (IHM) System of the present example embodiment.

Part II A Detailed Description of the Individualized and Collaborative Care 'Indima™ Apparatus' Health Care System The Indima™ Apparatus system is a lifelong health management hybrid system consisting of three subsystems; starting from the beginning of life with individualized health management (IHM) through individualized (chronic) disease management (IDM) until (lifelong) individualized support management (ISM).

1. The Actual Situation: Systemic Background Description of Existing Problems as Challenges Preliminary Remarks A systemic analysis of 'Health Care Management of Today' would fill a book which is not possible for giving just a background information.

1.1 'Health Management' Instead of 'Disease Management'

Some 3000 years ago, in China, 'Health Management' was literally 'health-oriented'. It was therefore comprehensive and integrative and therefore necessarily preventive: The ancient Chinese 'Health Care Professionals' (HCP's) were rewarded for the health of their 'clients' (unlike the Latin origin word 'patient', literally translated 'suffering ones') and not for treating diseases.

On the contrary, todays health care systems can be defined as 'health reparation' systems or 'disease management' systems for which it is a common saying in the American Medical Community that there are 'rushed doctors' working 'in a fragmented system'.

1.2 Alienation from Individual Health Management: The Fragmented Health Care System It seems that the citizens of the First World countries in the so-called Trias' (North America with USA, Canada; Europe; Japan plus ASEAN) are 'separated' from their health to use a strong term.

Especially in the United States of America, the pharmaceutical companies and the 'payors', the insurance companies, are more or less in one hand. Thus, the doctor working in an HMO(?) is very much in a situation of an 'economically dependent' person (and economic 'victim') with the patient so to say being the 'victim of the victim'.

The facts are: The United States of America make up 4% of the First World population. They spend 40% (factor 10 !) for 'disease management' with very poor results: 66% of the population are overweight, 34% are 'obese', and the rate of diabetics type 2 (which is a result of the 'individual health management' of the persons concerned) is by far the highest in all First World countries. This situation has been described by Prof. Dr. Paul Ciechanowski, a leading US expert for Diabetes Management, Depression Management, 'Diapression' ('An Integrated Model for Understanding the Experience of Individuals With Co-Occurring Diabetes and Depression', 2011): 'the rushed doctor in a fragmented system', the contents of which are incorporated herein by reference.

Therefore, a comprehensive and integrative person/patient-centered 'health care' model is needed (see the B-P-P-S model):

We take diabetes as an example that the 'behavior-related' and 'self-care-related' diseases like especially diabetes mellitus type 2 reflect not only an individual's biomedical status (the 'peak of the iceberg': module 1/layer 1=Bio Marker), but also the underlying psychological situation of the person concerned (module 2/layer 2=Psycho Marker), the behavior patterns and personality traits (module 3/layer 3=Perso Marker), and the basic socio-economic origin of the person concerned with his/her genetic background (module 4/layer 4=Socio Marker): the B-P-P-S model. Health education is not dealt with in elementary, secondary or high schools—nor in colleges or at universities. Although it is the most valuable good of mankind, it is not treated and protected as such. The average citizen in the so-called Trias' of the First World (USA/Canada-Europe-Japan plus ASEAN/Australia/New Zealand) is actually disowned.

1.3 Role Concepts of Patients and Doctors in the Western World of Today (Examples USA and Germany/Europe)

An analysis of the role concepts of 'patients' and doctors/HCP's. The research in Europe (in Germany) which also reflects results in the USA and Japan (although the frequency in the groups is certainly different in these countries and the social background influences the results so that in each country a specific analysis is needed) is described in the following in order to give some basic insight.

It has been shown that 'biomedical treatment' (level 1=Bio Marker in our BPPS model) should not only include the psychological state of the person (level 2=Psycho Marker in the BPPS model), but also the personality and personality traits (level 3=Perso Marker in the BPPS model), and the social origin as well as the socio-economic situation and the social environment of the patient (level 4=Socio Marker in the BPPS model).

This is shown in the following pattern of patients:
- Group 1 'DETERMINISTIC GROUP': 'Health is determined by fate (good or back luck).'
- Group 2 'MEDICAL BELIEVER GROUP': 'I cannot do anything. My (high quality) doctor is in charge of my health.'
- Group 3 'NATURE GROUP': 'Avoid the doctor and the medical institutions. Live healthy—and everything will be fine.'
- Group 4 'ENLIGHTENED COLLABORATIVE CARE GROUP': 'I am aware of the fact that it is my health and my life: So I am looking for a doctor/HCP as a professional partner and act as a more or less self-conscious and responsible partner of my doctor and/or the health care professionals.'

The doctors have corresponding role concepts:
- Authoritarian doctors like the deterministic group patients. These patients listen to the doctor as if he was 'fate' or even 'God'.
- The paternalistic doctors prefer the medical believer group. They are seen as an authority and the patients cling to their lips.

All groups of doctors are somewhat distant and skeptical about the nature group which avoids contact with the doctors and is more of an 'anti business model'. The 'enlightened collaborative care group' is officially preferred by all doctors. But one thing is what is said in theory ('We all like and strive for 'collaborative care'')—the reality may be far away from it. According to several research results, 80% of the patients in the USA receive about 20% of the health care visit time of the American doctors. The other 20%, the 'system-preferred' receive 80% of the health care visit time.

1.4 Standardized Vs. Individualized Medical Treatment

It is evident and need not be proved that first of all, standardized medical care is necessary for all patients to create a basis ('basic service').

For a developed country of the First World, however, an 'individualized patient treatment model' is to be preferred for optimal results, especially in the case of psychology- and personality-related (chronic) diseases where the socio-economic status and the social environment also play a significant role.

1.5 The Patient as an 'Object' Vs. The Responsible 'Empowered' Self-Conscious Patient Again, there is no need to argue that the patient as an object certainly receives the minimum care and has good chances to survive.

For an optimum life span, for best quality of life, and for a best medical treatment in the case of illness, however, clearly the 'empowered' patient, showing initiative, empowerment and being able to carry out a 'high quality self-care' has the better life.

1.6 Openness, Trust, and a Positive Doctor-Patient Relationship are the Basis for Collaborative Care This again is obvious and need not be proved (although there is a huge amount of research data proving this as an empirical fact).

1.7 Individualized and Person-Centered Health Care for Chronic Diseases (IDM)

Medical care has improved enormously in the last century. The life expectancy of today's generations has been increased significantly.

Where, however, addictive patterns and very change-resisting behavior patterns are prevalent, the classical care situation with a short contact between patient and doctor reaches its limits.

This is true for all chronic diseases. So there is a need for the patients with chronic diseases to receive 'treatment support' or even 'adaptation and behavior modification support'.

1.8 Lifelong Support for Chronical Disease Patients is Necessary ('Individualized Support Management'=Ism)

All the existing research has shown that patients with chronic diseases need support and there are altogether four sources:

(1) the person himself/herself (self-motivation, internet contacts, health care education, training etc.);
(2) the direct social environment (support by partner, family, and friends);
(3) the 'second' social environment and groups (like patient support groups, training groups, and self-care groups);
(4) the medical support by doctors and health care practitioners (as the last—and financially most expensive and also limited—resource).

2. The Corresponding Challenges and Solutions for the Existing Problems 2.1 'Standardized' Treatment Problem:

The 'Health Care Repair Systems' of today (with the 'rushed doctor in a fragmented system') are disease-focused with patients as (more or less) an 'object' of a (more or less) standardized treatment.

Solution

'Integrative Health Care Systems' with patients as a 'subject' (emancipated as 'client').

2.2 'Separation' from the Own Health

Problem:

The modern patients are more or less 'separated' from or 'alienated' by their own health; only very few (less than 10% of the population) are really fully empowered and 'in charge of their individual health management'.

Solution

Offering low-cost access to empowering and enabling devices for self-care, creating systems supporting the synergy between 'client' and doctor (the 'Synergistic Unit' of Health Care) and thereby creating the desired situation of 'Collaborative Care'.

2.3 Need for Help

Problem:

Both, patients and doctors, need help.

Let us take the example of the US American society: More than 50% of the doctors suffer from burnout syndrome and doctors starting show the normal depression rate of the population (4%) which increases after one year up to striking 25%.

Let us take the following examples of diabetes care: Only 7% of the US patients reach the three objectives which are relevant to preserve their lives: reaching the blood pressure goals, reaching the objectives for lipids/cholesterol, and reaching the average level $HbA_{1c}$ for blood sugar, avoiding extreme hypoglycemic and hyperglycemic states.

Solution

Offering a (1) 'Self-Assessment': perception of the patient about his situation, (2) Reality Check (lab results and diagnosis), (3) Collaboration Care Action: three key criteria (blood pressure, cholesterol/lipids, blood glucose).

This system is of significant help for the patient.

2.4 Standardized Vs. Individualized Treatment of Diabetes Type 2 Patients

Problem:

All diabetes type 2 patients are certainly checked in terms of bio-medical status (level 1). This is, however, only the 'Peak of the Iceberg' (see Annex I).

Solution

In order to understand the patient's situation and to change it, to have better results, all four layers of the B-P-P-S model need to be considered:

Layer II: 'Psycho Marker'=psychological status of the patient;

Layer III: 'Perso Marker'—personality traits, personal style of interaction and communication, individualized needs for support and individualized support and guidance;

Layer IV: 'Socio Marker'='Socio-Economic Background', for instance the 'Tipping Points' in a social environment, where the patient for instance does not want to be an outsider and stays with the 'unhealthy lifestyle' of his environment.

This is done by the BPP-S model, including all four layers.

2.5 Treatment of the Patient as an 'Object' in a 'Standardized Procedure'

Problem:

If the patient is treated as an 'object' in a 'standardized treatment procedure', the results are inferior (especially in person- and psychology-related chronic diseases).

Example 1

More than 30% of diabetes patients with strong depression (about 12%) and some 20% with clear depressive tendencies (Paul Ciechanowski, MD, PHD, article on 'Diapression': 'Diapression: An Integrated Model for Understanding the Experience of Individuals With Co-Occurring Diabetes and Depression', 2011 (the contents of which are incorporated herein by reference)) are not reached. It is evident that a person suffering from depression is not open for a high quality self-care diabetes treatment.

Example 2

Some 50-70% of the patients with diabetes mellitus type 2 suffer from an 'eating addiction' (F. Kiefer, M. Grosshans, 'Beitrag der Suchtforschung zum Verstandnis der Adipositas', 2009 (the contents of which are incorporated herein by reference)), and show the same symptoms/activity patterns in their brain when looking at their favorite 'juicy hamburger' or other favorite food as alcoholics do when looking at alcohol.

Example 3

It is also evident that Adipositas Patients' who are 'eating addicts' in diabetes mellitus type 2 need support and a psychiatric treatment (Prof. F. Kiefer, University of Heidelberg, Central Institute for Addictive Diseases, Mannheim)

and that a normal 'rational appeal' will help as little as telling a heroin or alcohol addict: 'It would be better if you did not take heroin or if you did not drink alcohol.'
Solution A categorization of patients is needed which is aimed at low costs and with the patient as a 'collaborative client/subject'—and not against the patient's will as an 'object to be changed'.

Group II: 'Collaboration and Control' [example 'Diabetes Mellitus Management' of three key criteria: (1) blood pressure, (2) cholesterol/lipids, (3) blood glucose]

2.6 The Patient as an 'Object' within a Highly Complex Technological Process
Problem:

The cost-driven medical care and health care systems of today have the effect that the patients have become more and more an 'object' within a highly complex technological process. The very disappointing results with chronic diseases and with all diseases which need 'to take into account the needs of the person' show that there is a definite need for change.
Solution Empower and enable the patient, enable the patient to be 'in charge of his health' and be 'in the driver's seat of his health management'.

BPPS Model: Group I: 'Empower and Enable' the patient (E&E)
BPPS Model Group II: 'Collaboration and Control' (C&C)
BPPS Model Group III: 'Coping with Diabetes and Adaptation of Lifestyle and Coping' (C&A)

2.7 The Threshold Between Patients and Doctors
Problem:

There is a threshold and barrier between many patients and doctors which needs to be overcome. This, however, is very difficult especially for the complex topics and needs of treating chronic diseases and treating diseases with intimate personal aspects which require to understand the psychology and the personal situation of a 'patient' in order to empower him to be a 'client'.
Solution Support the doctor through a self-analysis and self-assessment of the patient which is giving him access to the inner situation of the patient while the patient still is in a situation to initiate and to control what is going on so that 'he owns the process'. Openness and trust are the basis for collaborative care.

2.8 Rational Appeals or 'Logic' are not Helpful
Problem:

Lifestyle adaption and behavior modification for diabetes type 2 patients as well as for patients with depression or the combination of both, patients with diapression as well as support for patients with diabetes type 1 (psychological treatment support) is not achieved by rational appeals or 'logic'.
Solution The patient should feel perceived as a 'person'. The person should feel understood and the three steps of the client-centered and non-directive therapy with worldwide acceptance as the basis for individual treatment including psychological and personality issues, (1) starts with 'unconditioned' acceptance, empathy, and understanding and (2) leads to enabling the patients to feel 'I am okay' and to be treated as a partner and an 'equal'. This is the 'gateway' to 'Collaborative Care' which (3) finally leads to a collaborative care of the 'Synergistic Unit' patient-doctor dealing with reality, facing the problems, discussing openly and coming to 'collaborative care decisions for action'.

2.9 Coping with Crisis Situations
Problem:

All patients with chronic diseases facing (for depressive patients twice in a lifespan) a crisis where they need definite and urgent support. Leaving patients with chronic diseases alone for themselves does not lead to best results.
Solution There should be a (hopefully) low-cost and self-initiated system or device which allows patients to define (step 1) by a 'Self-Assessment'—(step 2) with the help of an expert in 'Collaborative Care', a medical doctor or health care professional, discussing the lab-results and diagnosis what can be best done for this individual patient (step 3: 'Action Plan') in order to cope with his chronic disease and to achieve the best possible results.

The '3-Step-Model of Collaborative Care'
  a) secured and supported/'induced' by a 'web-based' (low cost) system,
  b) patient-driven (patient-initiative=identification='ownership'=better results),
  c) creating the 'Synergistic Unit' of 'Collaborative Care'.

3. the Solution is Reached by the Hybrid System of 'Individualized Health Management' (IHM-IDM-ISM)

In a first preferred embodiment:
  (I) IHM='Individualized Health Management';
  (II) Individualized Disease Management'; and
  (III) ISM='Individualized Support Management'
are provided using an integrative and comprehensive person/patient-centered automated and web-based health care system integrating IHM, IDM and ISM over the full lifespan of an individual.

In a second preferred embodiment:
'Bio Medical', 'Psycho', 'Perso' and 'Socio' markers of the BPPS model are integrated into an individual comprehensive Health & Disease Management Profile:
  'B'=Bio-medical ('Bio Markers') elements and components (as Module 1/Layer 1);
  'P'=Psychological ('Psycho Markers') elements and components (as Module 2/Layer 2)
    dynamic criteria as an element or component of biomedical diagnosis; access to 'Inner State' with intimate personal/patient information through self-report/self-assessment;
    the 'Individual Psycho System';
  'P'=Personal ('Perso-Markers') elements and components
    (as Module 3/Layer 3)
    Partially state of the art as elements of a diagnostic profile;
    novelty: the 'Individual Personal Profile' as system;
  'S'=Social ('Socio Markers') elements and components
    (as Module 4/Layer 4)
    Novelty: the 'Individual Social and Socio-Economic Profile' as system.

In a third preferred embodiment, a unique 5-Stage-Individualized Health Care/Disease Management System is provided with:
  Stage 1: Self-Assessment (Self-Report) with instant scoring for the resulting ('intimate') automated report for the respective person/patient;
  Stage 2: Complemented by biomedical facts and diagnostic results (the so-called 'Reality Check') to a 'feedback loop': Self-assessment vs. bio-medical facts as learning model for the person's/patient's expertise in Health/Disease Management.

Stage 3: 'Hybrid' Categorization of the persons/patients by using as sources
  (1) Self-Assessment/Self-Report,
  (2) Doctor's/HCP's 'Expert Rating',
  (3) linked to 'Bio-Medical' and to growing, newly installed integrative BPPS-databanks, creating a hybrid categorization in three dimensions;
Stage 4: (Derived from Stage 3): Individualized Treatment Scheme;
Stage 5: Derived (from Stage 3): Individualized Support Program;

The following three phases of diabetes management are involved:
Phase I: 'Empowerment & Enabling' (E&E);
Phase II: 'Collaboration & Control' (C&C);
Phase III: 'Coping & Adaptation (C&A)'.

In a fourth preferred embodiment, a web-based treatment support and behavior modification system is provided, integrating three stages to an automated 'Collaborative Care System':
Stage 1: 'Self-Assessment' (individual initiative and openness for feedback and learning); Stage 2: 'Reality Check' (lab results and assessment by the medical team); Stage 3: Resulting patient-doctor interaction as 'Synergistic Unit' in the sense of Collaborative Care:
  (1) patient-driven automated/web-based=easily accessible self-care AND collaborative care system;
  (2) Supporting both patient ('person') and doctor/HCP ('Health Care Coach') to realize a 'synergistic unit' with best use of (outcome-related) resources.

Example

Description of the Use of the Indima™ Apparatus in Diabetes Management

The following description illustrates how a person with diabetes (PwD) and his/her health care provider would use the system of the example embodiment. In the preferred embodiment, the HCP's office (e.g. the medical technician or office manager, depending on the office organization) selects the PwD for participating in using the system:

Step (1)

In a first step, the HCP's office assigns a reference ID to the PwD and sends this ID as well as the PwD's mailing address to the Service Center. It is assumed here that the PwD is notified by the HCP's office that the HCP would like the PwD to participate.

Upon receipt of the PwD's information from the HCP's office, the Service Center personnel enters the information into a database for future reference.

Step (2)

In a second step, the Service Center sends a questionnaire and instructions to the PwD's address with a self-addressed, postage-paid envelope. The instructions contain also a letter from the HCP to the PwD with the renewed request for participation.

Step (3)

In a third step, the PwD answers the multiple choice questions of the questionnaire. The instructional material provides a clear description of this task. In case the PwD needs additional support in filling out the questionnaire, the PwD can access a help desk through calling a toll-free number also provided with the material. The PwD puts the completed questionnaire into the self-addressed postage-paid envelope and returns it to the Service Center.

Step (4)

In a fourth step, the Service Center prepares the completed questionnaire for electronic processing. This usually includes scanning in the questionnaire to translate the answers into electronic form, assigning the information to the PwD's ID, and storing the information in the PwD's database record. The Service Center performs the actual processing. It sends the PwD reports and the HCP report and the self-care domain questionnaire to the PwD. It also sends a note of completion to the HCP's office stating that the PwD's information has been processed and that the reports have been sent to the PwD.

Step (5)

In a fifth step, the PwD reviews the report and indicates if there are any areas where he/she doesn't see himself/herself adequately described by the electronically created report. Any conceivable mismatches will be discussed between PwD and HCP during the next consultation. The PwD fills out a questionnaire to assess the current self-care domain status additionally, the PwD is urged to write down questions to ask the HCP and topics to discuss with the HCP at the next office visit. The PwD then sends the questionnaire back to the Service Center utilizing the self-addressed postage-paid envelope.

Step (6)

In a sixth step, the Service Center processes the answers to the self-care domain status questionnaire. Similar to step four, the preparation consists of scanning and storing the information in the PwD's database record. During the actual processing, the Service Center combines the PwD's information from step four with the self-care domain information and creates the HCP prompt sheet and the PwD prompt sheet. The Service Center sends both sheets to the PwD for use in the upcoming consultation with the HCP. The PwD takes the HCP and the PwD prompt sheets to the next consultation. The PwD should be aware of all information that the system provides to the HCP. If the PwD does not feel comfortable with providing the information to the HCP, the PwD can opt out of doing so. However, this case seems to be very unlikely.

Step (7)

In a seventh step, the actual meeting between PwD and HCP takes place. The PwD hands both prompt sheets to the HCP. The HCP prompt sheet provides a 'snapshot' of the PwD as a person to the HCP including insights into the PwD's preferred interpersonal style psycho-social environment. It also relates in a concise form how the PwD would like to be supported and guided by the physician in case the primary communication concept—derived from the style profile (IDEA) tool—does not prove to be effective with the PwD. The HCP prompt sheet contains the 'dos and don'ts' for interacting with the PwD. Preferably, a PwD example dialogue is provided to help the HCP through an initial phase of unfamiliarity with the approach and as occasional refresher during routine use. The HCP uses this information to adjust his/her way of communication to the interpersonal preferences of the PwD. The assessment results of the self-care domain status questionnaire can be utilized to structure the topics discussed during the consultation since the HCP sees directly how the PwD's health care status looks in the PwD's self-assessment, what the PwD considers to be significant, and where the PwD is willing to change. The PwD prompt sheet also contains the topics that the PwD would like to discuss with the HCP during the consultation. The PwD prompt sheet provides space for the HCP to document pertinent lab or physiological results (e.g. HbA1C, triglycerides, etc.) and biomedical or physical facts (e.g., blood pressure, weight) for the PwD.

Reality deviance predictor values (or success factors or "need for action levels") can be determined by comparing an extent of a deviation between results of the PwD's self-assessment (subjective evaluation) compared to results of the laboratory tests and biomedical facts on the part of the HCP (objective evaluation). For example, in the self-assessment the PwD answers questions on a questionnaire pertaining to one or more of this patient's biological/medical (physiological) condition, psychological (mental and emotional) condition, personality and genetic factors, and social and socio-economic factors (groups of state parameters). This can correspond to the following reality deviance predictor values or success factors/indicators in which the extent of the deviation between the subjective and objective evaluations is one or more of; extreme difference; definite difference, some difference; and little or no difference, respectively.

The HCP can inform the PwD of the reality deviance predictor values (success factors) as to the level of urgency in a need for action or probability of success in treating the disease or the health problem of the PwD based on the PwD's current self-assessment. For example, the PwD and the HCP have a discussion comparing the self-assessment (how the PwD subjectively views their condition) to the physiological test results conducted on the part of the HCP and the biomedical facts about the condition of the PwD obtained by the HCP (how the HCP objectively views the condition of the PwD). This provides the PwD with a learning model in self-health and disease management.

The HCP writes action agreements and the goals that the HCP and the PwD have jointly agreed upon in the space designed for this purpose. That is, the reality deviance predictor values or success factors can be used by the HCP to determine appropriate action parameter groups including an individualized and collaborative health care action plan for the PwD. The PwD is brought into the decision making process as they see that their mindset toward their lifestyle and how they view the disease (such as overeating/no exercise and for diabetes Type 2 patients 'this is a genetic disease and there is nothing I can do about it") is compared to an objective evaluation by the HCP. This decision making process may even consider data from other PwDs as discussed below in connection with adaptive or learning nature of the computerized system, such as likelihood of stroke, cardiovascular disease or death, or projected years of reduced life, in PwDs having the same success factors or reality deviance predictor values. The discussion includes the PwD viewing the success factors obtained with the current self-assessment or mindset of the PwD. The individualized and collaborative health care action plan for the PwD can be tailored to reaching blood pressure goals, reaching objectives for lipids/cholesterol, and reaching an average level $HbA_{1c}$ for blood sugar, avoiding extreme hypoglycemic and hyperglycemic states.

Step (8)

In an eighth step, the PwD follows the recommendations received from the HCP and works on achieving the agreed-upon goals as documented on the PwD prompt sheet.

Step (9)

A set period of time before the next office visit, the Service Center sends a questionnaire for the assessment of the current self-care status and the topics to be discussed during the upcoming health care visit of the PwD which constitutes a ninth step.

Step (10)

In a tenth step, the PwD fills out the questionnaire and writes down questions to ask the HCP and topics to discuss with the HCP at the next office visit. The PwD then sends the questionnaire back to the Service Center utilizing the self-addressed postage-paid envelop.

Step (11)

In an eleventh step, the Service Center processes the answers to the self-care domain status questionnaire. Similar to step four, the preparation consists of scanning and storing the information in the PwD's database record. During the actual processing, the Service Center combines some of the PwD's information from step four, especially the personal support and guidance preferences, with the self-care domain information and the discussion topics and creates the HCP prompt sheet and the PwD prompt sheet. The Service Center sends both sheets to the PwD for use in the upcoming consultation with the HCP.

Iterative Steps 7-11

The flow described above now returns to step seven. Steps seven through eleven are executed iteratively.

Through the initial in-depth assessment of the PwD's interpersonal style, psycho-social environment, and personal support and guidance preferences, the PwD and HCP get a broad but concise picture of the PwD as a person. This is a significant step towards establishing the PwD as an equal partner in a collaborative healthcare relationship that is individualized to optimize the PwD's healthcare outcomes. The iterative, active involvement of the PwD in preparing the consultation by defining the topics to be discussed with the HCP and reflecting on his/her health care status and behavior is another significant step. Also, the focus on collaborative goal setting and follow-up on these goals contributes—with other steps—to achieving sustainable behavior change. This behavior change is not only change on part of the PwD but also on part of the HCP.

The individualized disease management (Indima™) system may be used for predicting patient status with diabetes and for controlling therapeutic success using self-adapting model structures for individual disease/diabetes management (Indima™).

The 'Indima™ Apparatus' comprises a method, system, and computer program related to optimal individualized diabetes management with control of diabetes. The Indima™ Apparatus is directed to predict the long-term exposure to hyperglycemia and hypoglycemia, and the long-term and short term risk of severe or moderate hypoglycemia and hypoglycemia in diabetes, based on physiologic readings, like ingested carbohydrates, monitored blood glucose, administered volume of insulin and collected data by a self-monitoring patient-doctor-system for individualized disease management with 'Bio-Marker' (biomedical data), 'Psycho-Marker' (psychological characteristics), 'Person-Marker' (personality and behavioral traits), and 'Socio-Marker' (social environment and socio-economic characteristics). The Indima™ Apparatus, i.e., method, system, and computer program product, enhances existing home blood glucose and ingested carbohydrate monitoring methods and a new 'Indima™' self-assessment and self-control system for the patient by himself and in interaction with his/her doctor/HCP's. The Indima™ Apparatus uses an intelligent data interpretation component, which is capable to predict both blood glucose levels and periods of hyperglycemia and hypoglycemia, and thus to offer options for the doctor/HCP to optimize the individual diabetes management, making use of all four Indima™ parameters, i.e. the Indima™ Bio-Marker, the Indima™ Psycho-Marker, the Indima™ Perso-Marker and the Indima™ Socio-Marker, and to enhance emerging continuous monitoring devices by the same features. With these predictions, a patient's computer model can be created and the person with diabetes can take steps for an individualized diabetes management. With the offered options for diabetes treatment, this will support patient and doctor/HCP to prevent the adverse consequences associated with hyperglycemia and hypoglycemia.

The Indima™ Apparatus analyzes all existing patient-related data ("BPPS'): biomedical data (B), psychological profile (P), personal and behavioral traits and characteristics (P), and social environment and social portrait (S) of the innovative 'Indima™' Analysis-Engagement and Support (AES) System.

Based upon this novel Indima™ system with all success factors (from empirical research) and the four parameters B-P-P-S, the Indima™ apparatus is a novel support for doctor and diabetes patient by predicting the short-term and long-term blood glucose levels and calculating the insulin concentrations to be administered for an almost constant blood glucose level.

A Process System for Predicting Patient Status with Diabetes and for Controlling Therapeutic Success We will now describe a process and system for predicting patient status with diabetes and for controlling therapeutic success using self-adapting model structures for diabetes management (for example Neuronal Network Systems).

The present system relates generally to glycemic control of individuals with diabetes, and more particularly to a computer-based system and method for evaluation of predicting glycosylated hemoglobin ($HbA_{1c}$ and $HbA_1$)/blood glucose and risk of incurring hyperglycemia and hypoglycemia by the help of an individual patient's model.

Extensive studies, including the Diabetes Control and Complications Trial (DCCT) (see DCCT Research Group: The Effect of Intensive Treatment of Diabetes on the Development and Progression of Long-Term Complications of Insulin-Depend Diabetes Mellitus. New England Journal of Medicine, 329: 987-986, 1993), the Stockholm Diabetes Example embodiment Study (See Reichard P, Phil M: Mortality and Treatment Side Effects During Long-Term Intensified Conventional Insulin Treatment in the Stockholm Diabetes Intervention Study. Diabetes, 43: 313-317, 1994), and the United Kingdom Prospective Diabetes Study (See UK Prospective Diabetes Study Group: Effect of Intensive Blood Glucose Control with Metaform in on Complications in Patients with Type 2 Diabetes (UKPDS 34), Lancet, 352: 837-853, 1998), have reportedly demonstrated that the most effective way to prevent the long term complications of diabetes is by strictly maintaining blood glucose (BG) levels within a normal range using intensive insulin therapy. The contents of the aforementioned studies are incorporated herein by reference.

However, the same studies have also documented some adverse effects of intensive insulin therapy, the most acute of which is the increase risk of frequent severe hypoglycemia (SH), a condition defined as an episode of neuroglycopenia which precludes self-treatment and requires external help for recovery (see DCCT Research Group: Epidemiology of Severe Hypoglycemia in the Diabetes Control and Complications Trail. American Journal of Medicine, 90: 450-459, 1991, and DCCT Research Group: Hypoglycemia in the Diabetes Control and Complications Trial. Diabetes, 46: 271-286, 1997 (the contents of both of which are incorporated herein by reference)). Since SH can result in accidents, coma, and even death, patients and health care providers are discouraged from pursuing intensive therapy. Consequently, hypoglycemia has been identified as a major barrier to improve glycemic control (Cryer P E: Hypoglycemia is the limiting factor in the management of diabetes, Diabetes Metab Res Rev, 15: 42-46, 1999 (the contents of which are incorporated herein by reference)).

Thus, patients with diabetes face a life-long optimization problem of maintaining strict glycemic control without increasing their risk of hypoglycemia. A major challenge related to this problem is the creation of simple and reliable methods that are capable of evaluation both patient's glycemic control and their risk of hypoglycemia and hyperglycemia, and that can be applied in their everyday environments.

It has been well known for more than twenty-five years that glycosylated hemoglobin is a marker for the glycemic control of individuals with diabetes mellitus (type 1 or type 2). Numerous researchers have investigated this relationship and have found that glycosylated hemoglobin generally reflects how the average BG levels fluctuate considerably over time, and it was suggested that the real connection between integrated glucose control and BC would be observed only in patients known to be in stable glucose control over long periods of time.

Early studies of such patients produced an almost deterministic relationship between average BG level in the preceding 5 weeks and $HbA_{1c}$ and this curvilinear associated yield a correlation coefficient of 0.98 (See Aaby Svendsen P—Lauritzen T, Soegard U, Nerup J (1982), Glycosylated Hemoglobin and Steady-State Mean Blood Glucose Concentration in Type I (Insulin-Dependent) Diabetes, Diabetologia, 23, 403-405 (the contents of which are incorporated herein by reference)). In 1993 the DCCT conclude that $HbA_{1c}$ was the 'logical nominee' for a gold-standard glycosylated hemoglobin assay, and the DCCT established a linear relationship between the preceding mean BG and $HbA_{1c}$ (see Santiago J V (1993), Lessons from the Diabetes Control and Complications Trail, Diabetes, 42, 1549-1554 (the contents of which are incorporated herein by reference)).

Guidelines were developed indicating that an HbA of 7% corresponds to a mean BG of 8.3 mM (150 mg/dl), an $HbA_{1c}$ of 9% corresponds to a mean BG pf 11.7 mM (210 mg/dl), and a 1% increase in HbA corresponds to an increase in mean BG of 1.7 mM (30 mg/dl). The DCCT also suggested that because measuring the mean BG directly is not practical, one could assess a patient's glycemic control with a single, simple test, namely $HbA_{1c}$. However, studies clearly demonstrate that $HbA_{1c}$ is not sensitive to hypoglycemia.

Indeed, there is no reliable predictor of a patient's immediate risk of SH from any actual data. The DCCT concluded that only about 8% of future SH could be predicted from known variables such as the history of SH, low BC, and hypoglycemia unawareness. One recent review details the current clinical status of this problem, and provides options for preventing SH, that are available to patients and their health care providers (See Bolii: How to Ameliorate the Problem of Hypoglycemia in Intensive as well as Nonintensive Treatment of Type 1 Diabetes, Diabetes Care, 22, Supplement 2: B43-B52, 1999 (the contents of which are incorporated herein by reference)).

Contemporary home BG monitors provide the means for frequent measurements through self-monitoring of BG (SMBG). The calculation between the data collected by the BG monitors and hypoglycemia/hyperglycemia can be done by a special algorithm in which a kind of general patient's model is included. Otherwise this general model does not permit an individual patient's therapy as specific personal parameters like sex, medical records, nicotine and/or alcohol abuses, weight, personal compliance, etc. can be handled in a personal model only.

Therefore, an individualized patient's model is provided by including individual data in the model, which will be methodically collected and verified over considerable time by the system. By the hand of this model, the BG in the early and far future can be predicted, the short-term and long-term risk of hypoglycemia, resp. the long-term risk of hyperglycemia can be estimated, and advice for an optimal therapy resp. a more congenial lifestyle can be given.

Responding to the need of statistical analyses that take into account the specific form of a patient's personal diabetes model, the inventors developed a method which can be described as followed: Based on physiological data of a patient like his blood glucose, his ingested carbohydrate—divided in the three classes fast, medium and slow carbohydrate—and psychological parameters of his self-control via the DISC/IDEA test (four main personality types: DISC=Driver-Introspective-Supportive-Cooperative or: IDEA=Introspective-Driver-Expressive-Amiable), a (neuronal) net structure—following the principle of the self-organizing-maps—is trained to create a neuro-mental ('neuronal') representation of his diverse diabetes states.

Next, these different states are combined to a time trajectory describing varying diabetes behaviors, resp. his diabetes histories, over selectable time windows.

Based on these trajectories, a prediction about the patient's status in the early or more distant future is calculated and a value for an insulin concentration to be administered is calculated via a second neuronal network structure to guarantee a strict maintaining of blood glucose (BG) levels within a normal range to prevent hyperglycemia and hypoglycemia.

In parallel, the neuro-mental model and the appointed therapy following from the prediction of the system is evaluated by the statistical method of the cross-correlation in the context of an evident medical care. Also, the DISC/IDEA-model to fix the psychological parameters of the patient's compliance is evaluated successively. In that way, it will be possible to optimize the therapy and the model of the diabetes patient step by step; also by changing the scheme of the therapy accordingly.

(1) First, according to a special aspect of the example embodiment, there is provided a data analysis method and a computer-based system for the simultaneous evaluation of diabetes patients' behavior and the predictive control of their glycemic states from the routinely collected physiological data blood glucose, ingested carbohydrate—divided in the three classes fast, medium and slow carbohydrate—and psychological parameters of a self-control test done by two neural net structures to prevent hyperglycemia and hypoglycemia.

(2) Second, according to a further special aspect of the example embodiment, there is provided a method, system, and computer program product to provide a predictive, i.e., forward-looking, assessment of a patient's medical, physiological, and psychological state based on data obtained on the patient and based on a rule-based categorization formula of the patient per the innovative psychological model, 'DISC' or 'IDEA', and, based on this assessment, to derive a therapeutic action agreement, such as—for the short term—administering a certain quantity of insulin and managing the patient in an appropriate, individualized manner. This evaluation is done by a combination of two neuronal net structures. The first of them stores momentary patient system vectors, describing a momentary patient status and combining them to time history sheets, which code a medical record over a selectable time window. Out of these records, a prediction regarding the patient's condition in the near or far future can be deduced. The second neural net structure calculates in parallel an insulin concentration which has to be administered to guarantee strictly maintaining blood glucose (BG) levels within a normal range to prevent hyperglycemia and hypoglycemia in the early or far future.

(3) Third, according to a still further special aspect of the example embodiment, there is provided a method, system, and computer program product to optimize the therapy of the diabetes patient step by step by using the statistical method of the cross-calculation to analyze the diverse physiological and psychological data of the patient versus the result of the therapeutic schemes which have been used.

These three aspects, as well as other aspects discussed throughout this document, can be integrated together to provide continuous information about the glycemic control of an individual with diabetes, and enhanced monitoring of the risk of hyperglycemia and hypoglycemia.

Part III Detailed Description of the Data Processing and Categorization of Patients by the InDiMa™ Processing Example Embodiment (Using the Example of an Application for Individualized Diabetes Management The 10 Success Factors of 'Diabetes Management' have been identified in 6 years of intensive empirical studies. The first study was done in the USA (April 2010) with a sample of n=1000 patients (900 Diabetes Type 2 and 100 Diabetes Type 1). The resulting '10 Success Factors' concept was confirmed in the German study, based on a sample of n=2356 patients. (see www.indimasurvey.com: Studies IS1, IS2, IS3)

The Indima™ Basic Processing System (IBP) consists of four program blocks that are integrated into the Indima™ Communication System.

1 The InDiMa™ Construction Tool

Figure 22:
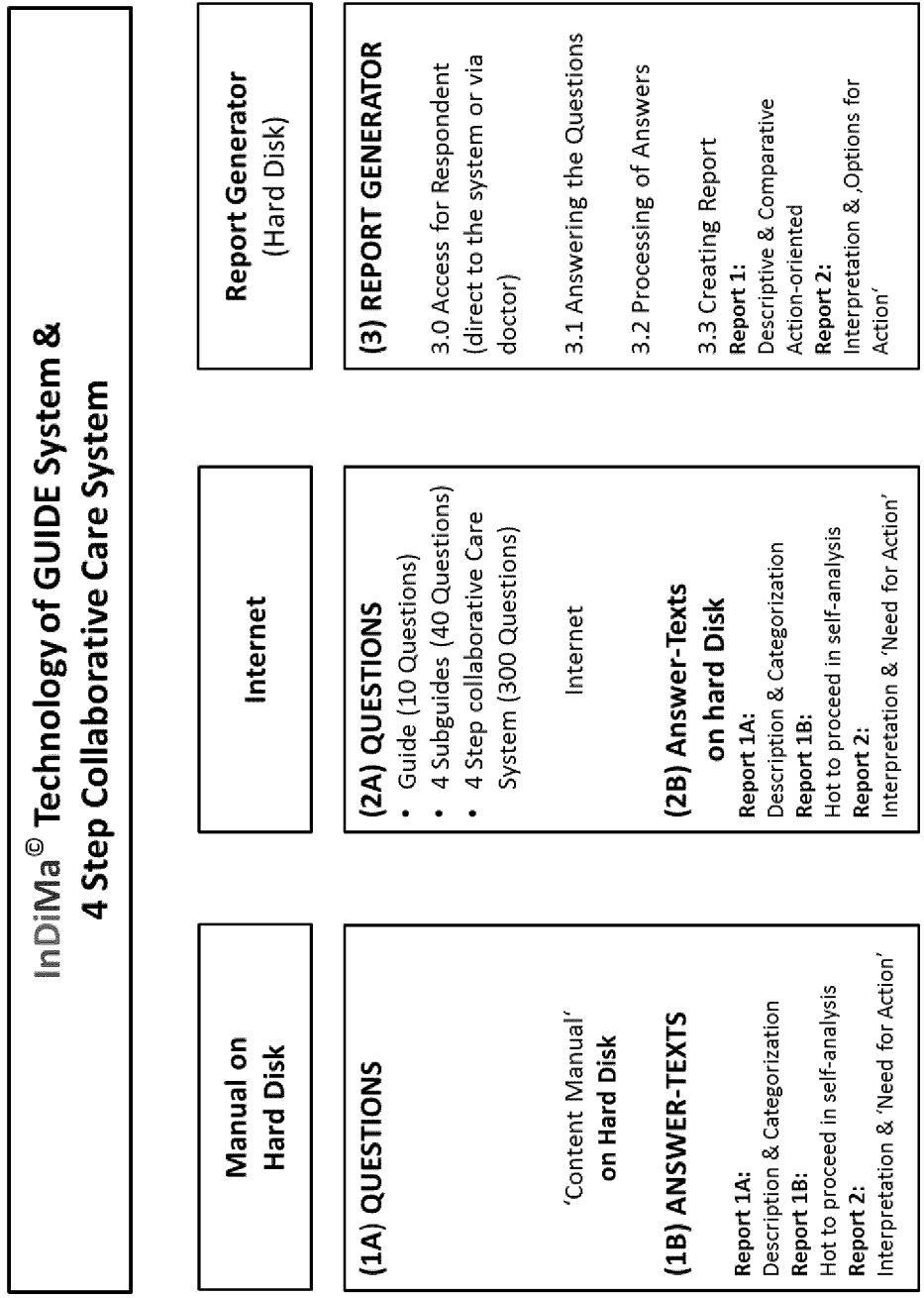
FIG. 22 is a schematic diagram of an example of four step collaborative care system of the present technology.
Figure 24:
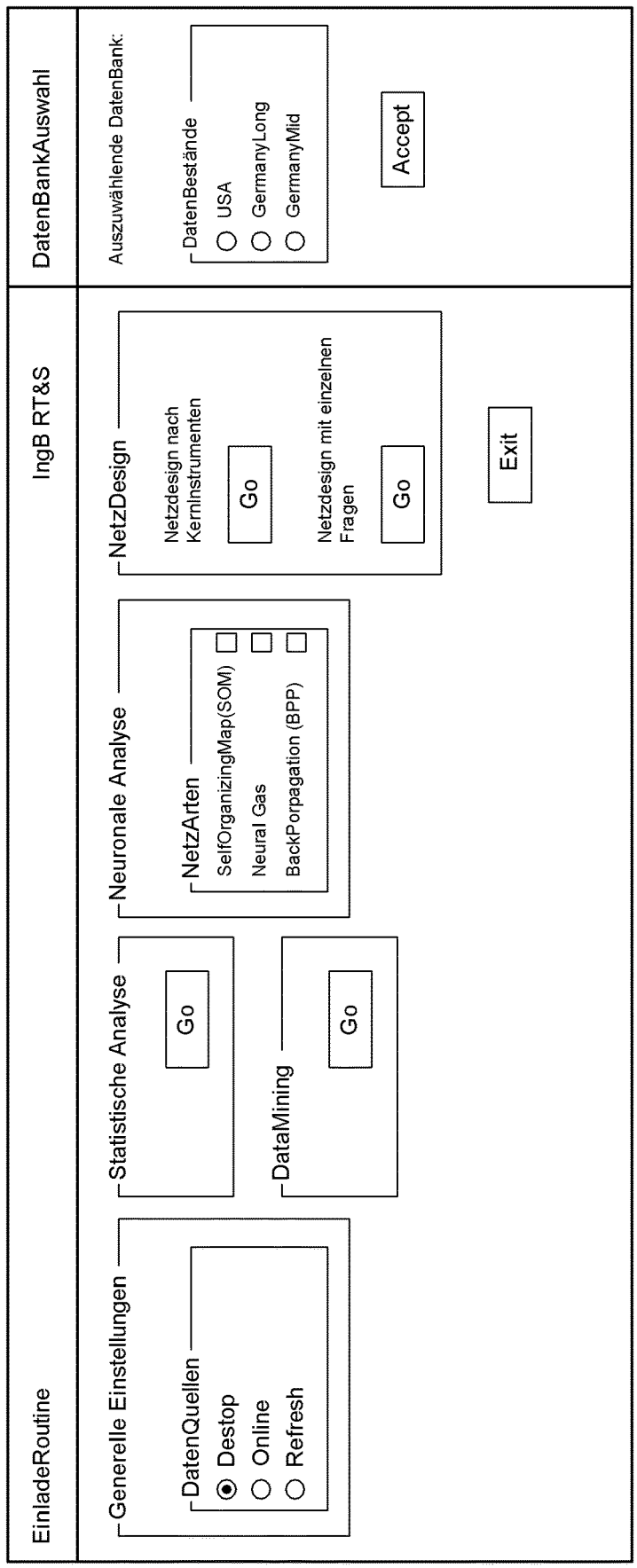
FIG. 24 is a sample screen shot of an example for a choice of data source.

We are describing here as an example the Indima™ Communication System, with reference to FIG. 22.

The Processing System of the 'Individual Health Management' and 'Individual Support Management' are identical.

The Indima™ survey-construction module (to generate questionnaires) is capable to handle
- a language module (multi-language approach for questionnaires);
- a questionnaire construction option to create questionnaires with:
  (1) variable scale approaches,
  (2) multiple choice possibilities,
  (3) 'open questions', and
  (4) reversed questions;
- an Indima™ questionnaire library, based on items of the Indima™ Communication System, i.e., the 10 core instruments and other parts which can be added to the Indima™ Communication System.

The Indima™ survey-construction module is built in such a way that it can export the questionnaires to the web (internes) for data entry and is approachable for the browsers: Internet Explorer (6 and 7 and higher), Firefox (2 and 3) and Safari (3, 0). This counts for 98% of the browser market.

Also based on the fact that the exploratory studies where on paper and pencil, the Questionnaire export functions are also capable to print the questionnaires into Word documents, HTML-files, ASP files and XML files.

The Indima™ survey-construction module is constructed in such a way that healthcare providers (HCP's)/doctors can set-up (after instruction) their specific questionnaires for each patient.

These specific questionnaires for each patient can pinpoint the therapy focus for a specific patient.

The patient-oriented approach of the Indima™ Communication System will generate a specific questionnaire for each patient or groups of patients out of the ICS question library.

2 The InDiMa™ Generator Tool

The 'Indima™ Report Generator Tool' is an application that works in cooperation with the 'Indima™ Portfolio System' (see chapter 1.3) and the 'Indima™ Survey Construction' module.

The report generator is built to create reports for survey trajectories. It is specialized for the creation of personalized reports for surveys.

Figure 47:
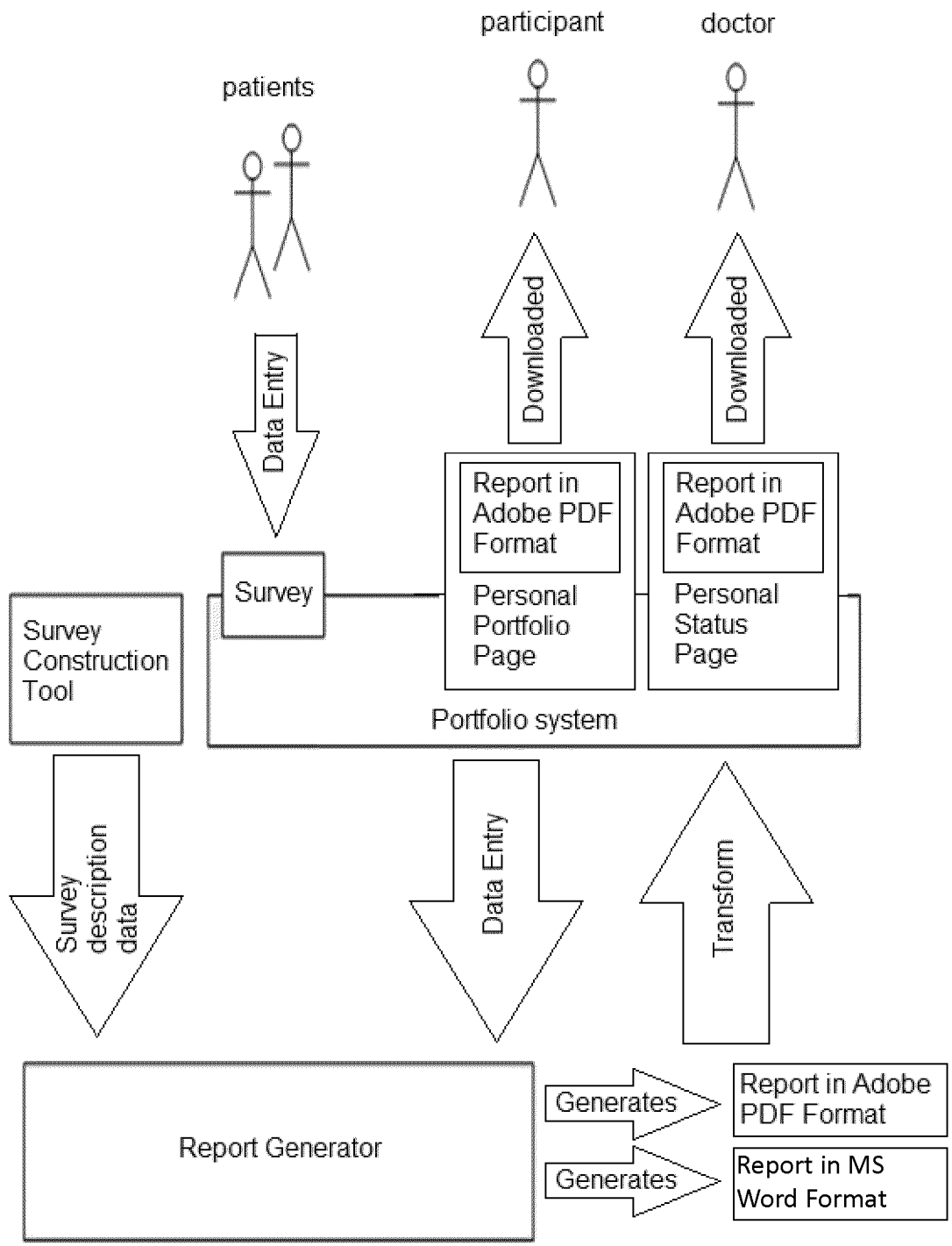
FIG. 47 is a schematic diagram showing how communication in the system is constituted.

The following FIG. 47 shows how the system communication between the modules is constituted.

There are four steps to online availability:

Step 1: Data are downloaded to the report generator.

Step 2: Reports are generated.

Step 3: The generated reports are uploaded back to the portfolio system.

Step 4: The reports are available online.

Although some aggregate functions are available, with the Indima™ Report Generator Tool, a report is always created for a specific patient. The reports thus generated, using the Indima™ Report Generator Tool, can automatically be uploaded back to the Indima™ Portfolio System so that it is available to both participants (via the Personal Portfolio Page) and doctors/HCP's (through the Portfolio Status Page).

2.1 Structural Variations of Reports

Usually, every survey can be different from the next.

Hence, the resulting reports are likely to vary in structure as well.

That is why the Indima™ Report Generator Tool works with templates.

Partially complete documents can be re-used and adapted.

Hence, they provide the demanded flexibility.

The basis of every report is a report template.

A report template is a Microsoft Word XML document and hence can be edited using the widely used and supported Microsoft Word XML.

2.2 Report Template Variables

A report template contains report template variables.

A report template variable is a part of the report that is replaced by actual survey data, once a report is generated.

There are different types of report template variables.

One of them is a reference to a graph template.

A graph template shows information (averages, totals) about a specific survey question or a group of survey questions.

A graph template is also a Microsoft Word document, but can contain embedded Excel Chart or Microsoft Chart objects.

A graph template contains graph template variables.

A graph template variable is replaced by a (numerical) value upon report generation.

2.3 Individual and Group Reports

With the Indima™ Report Generator Tool the 'SMO/InDiMa™ Service Center' can create two types of reports:

(1) individual patient reports, (2) general reports.

Individual reports are reports that are created for specific patients and HCP's/doctors such as BIP Profiles (Basic Individual Profiles) and Promptsheets.

In the reports, data are used that is linked to a specific patient: The patients and HCP's/doctors are entered in the portfolio system under a 'Client Management' section.

General or Group Reports are reports that use all survey data, for instance for a group of patients for one doctor. Those kinds of reports are used to report on the higher 'organizational' level and not for specific patients but for patient groups or segments of groups.

2.4 Insertion of Texts and Graphs

Based on various settings that can be modified with the help of the user interface, the report generator will insert one or more texts or graphs in a report.

All texts reside in separate Word XML documents that have a particular, pre-set file name.

These documents all reside in a folder which has a certain, pre-defined structure.

Which texts are inserted and where, depends on the place of the variables and the syntaxes used in the report template.

As mentioned before, the 'Indima™ Report Generator Tool' works in cooperation with the 'Indima™ a Survey-Construction Module'.

Hence, it is possible to display information from the 'Indima™ Survey-Construction Module'.

Depending on the settings in the user interface and of course the patient's survey data, a text is inserted in the report.

All individual texts are stored in separate Word-XML and Word-docx documents that reside in a pre-defined folder structure.

3 The Indima™ Portfolio System 3.1 Data Entry Via Internet

It also can be used for data entry out of paper and pencil questionnaires.

3.2 Grouping of Patients

In the Indima™ Portfolio system, everything revolves around patients. To assure maintainability and to keep large amounts of patients synoptic, the patients are put in a hierarchical group structure belonging to a doctor or a HCP's group or to a Health Care Organization.

3.3 Patient Description

Patients are put into the system with a first name, last name, and e-mail address.

The patients are grouped and placed into a hierarchical group structure.

This structure consists of three levels:

Level 1: Health Care Organization

Level 2: Doctor

Level 3: Patient

Patients normally belong to one doctor in this system.

The combination, however, of diabetologist (level 2) and general practitioner (level 2) might be defined as 'level 1-tandem' (equivalent to a Health Care Organization).

3.4 Survey's and Data Entry

Basically, managing surveys and data entry in the Portfolio system is a matter of two things:

setting up and configuring surveys, giving participants access to survey by creating ID's.

Figure 23:
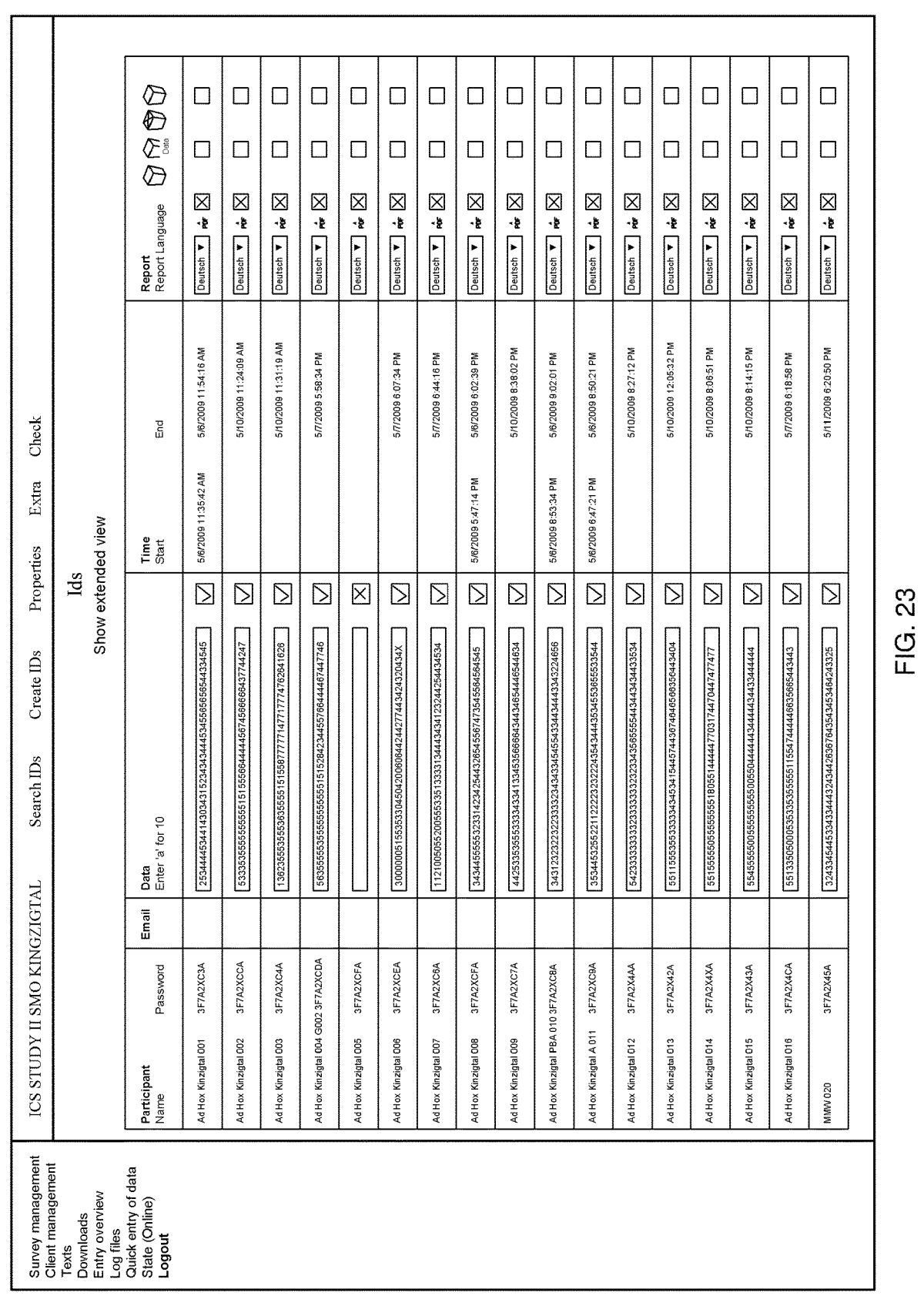

In the following FIG. 23 you will find a screen-print of the InDiMa™ Portfolio System.

Participant: In this section the patient's data are displayed. Also the password to access the survey is shown.

Mail: In this column normally the mail addresses of the patients are shown. The icon next to the e-mail address indicates that an instruction mail has been sent to that participant Data: In the input boxes the data entry of the survey is displayed. Please, note that only the data from input fields which names starting with 'question' is shown in this box.

Time: Here, time information about the data entry is displayed. Once a survey is accessed using a password, the start time is set. Once the survey is successfully submitted, the end time is set.

Report: Here the patient report can be downloaded or uploaded.

Trash bins: The checkboxes below the trash bins can be used to delete:
- instruction mails for patients. Sometimes the e-mail address entered by the patient is not correct, for example because of spelling errors;
- the data entry;
- the patient's PDF report;
- the complete ID.

4 Indima™ Patient/Doctor Signaling Tool 4.1 Personal Portfolio Page

Patients have a Personal Portfolio Page (PPP) to which they have access by using a password.

On the PPP a patient can see if there are any questionnaires to be filled out and can look at the results (reports) of earlier survey processing results.

4.2 Portfolio Status Page for the Doctor/HCP

The doctor can monitor the patient and the group of patients in their own underlying groups.

The doctor can 'login' to the Portfolio Status Page using an e-mail address and a password.

On this page, an overview is given of the patients that are in the system under the doctor's supervision.

All patients are shown and reports, linked to the patients, are available on this page.

4.3 E-Mail Contact by the Indima™ Signaling Tool

To maintain contact by e-mail the Indima™ Patient/Doctor Signaling Tool is installed.

This means that through this module
(1) instruction mails will be sent to the patients, with links to questionnaire;
(2) reminders can be sent;
(3) signaling of reports can be sent (also to doctors in the system).

These signals are built as normal templates like a normal e-mail message and are used as the basis for the instruction e-mail.

The template contains variables that are replaced by the Indima™ Patient/Doctor Signaling Tool to personalize the e-mail message.

Part IV Application of an Innovative Neural Network System Approach for (1) Classification (2) Individualized Treatment and (3) Individualized Support 1 Description of the Neural Network System ('Indima™. Apparatus'): Application for Patient Classification Establishing the Indima™ Model Through the Indima™. Apparatus The Indima™-Apparatus and its software tool serve the purpose of
(A) building models and processing of extensive sets data
- for the (Indima™-) model-based adjustments of neural networks,
- for the (Indima™-) model-evaluation of new models,
- for the neural-based processing of extensive sets data,
- for the analysis and determination of linear independence for the analysis and categorization of patients for all 10 Success Factors or within the three groups ('E & E', 'C & C', 'C & A') from 'green' ('okay, well developed') to 'red' ('very critical, urgent need for action'), respectively. The Application of the Indima™ Apparatus with the Integrative 'BPPS' Model
(B) The Indima™ Apparatus is used to
- select specific Success Factors or specific questions, respectively, to be able to check data with regard to Biomedical-, Psycho-, Perso- and Socio-Markers (BPPS-Modell);
- categorize, i.e. to determine the 10 Success Factors of the InDiMa™-Modell per patient (10 Success Factors in Diabetes and Health Management);
- categorize specific patients,
- categorize, i.e. to determine groups of patients:
  'E & E'=Empowerment & Enabling
  'C & C'=Cooperation & Control
  'C & A'=Coping & Adaptation [of Lifestyle]

The Broad Applicability of the InDiMa™ Apparatus

In addition, the Indima™ Apparatus has such a wide range of applicability, that it can analyze date from
- Access-based databases and
- Excel-based databases By means of the tools, i.e. the Indima™ Apparatus, the available sets of data were used to display the Indima™-Model, empirically elicited by Dr. Martin Muller-Wolf and Dr. med. Wolf-Dietrich Muller-Wolf (see Annex $IS_2$: Results from a study in the USA from Apr. 19, 2010).

2 Evaluation of the Indima™ Apparatus 2.0 Three Patient Categories in Diabetes Management (Identified in Study $IS_2$: n=1,000 in USA and Replicated in Study $IS_3$: n=2,356 in Germany)

2.0.1 Category I 'E & E'='Empowerment & Enabling'

In category I the four basic factors are summarized with a rather high accuracy, i.e. although these factors are independent, the structures that resulted from the four basic factors were similar to a large extent, so that each factor has to be scrutinized on its own, but that it is feasible and appropriate to gather them in a cluster (no classical arithmetic mean) which does seem to make sense from a medical perspective.

2.0.2 Category II 'C & C'='Cooperation & Control'

The same applies to category II: Good cooperation and control of the three medical core criteria (in spite of their independence from each other) correlates in practice, too and both aspects form a common frame.

2.0.3 Category III 'C & A'='Coping & Adaptation (of Lifestyle)'

Classical factor analysis showed that it is significant to point out that all four basic factors were happening at a 'high level of patient development in coping with diabetes but that it is also significant to capture very differentiated aspects, namely the following:

Success Factor 7: knowledge about self-care and the respective improvement focus;

Success Factor 8: Individualized support (not standard-procedures—'they are all the same') by the doctor who is treating the patient as an individual and offers individualized support in congruence with the patient's 'Individualized Support Program' (ISP);

Success Factor 9: Individualized treatment, considering the quality of self-care of the patient and his overall health status as well as Success Factor 10: Coping, adaptation of lifestyle and quality of life, especially for people with diabetes type 1 (genetically-caused diabetes), and the question how the patients cope with diabetes not only physically, but also psychologically (in the sense of quality of life). This applies especially to the age-related diabetes; to cope with the stress of diabetes management, the adaptation to the diabetes reality and its limitations is a challenge for all persons with diabetes.

Note: We put this description of the '10 Success Factors' before the methodological discussion in order to create a basic understanding of the Indima™ System so that the methods of the system and the meaning of the results can be understood more easily.

2.1 Results of the Evaluation (1) All 10 Success Factors are confirmed by the 'neural network' Indima™ NNS analysis.

(2) All three phases of development (group I, II and III) that have been identified in the empirical Indima™ studies (n=1000 in the USA and n=2356 in Germany) as so called 'secondary factors' have been confirmed by the NNS analysis:

Group I ('E&E'='Empowerment & Enabling') with the Success Factors 1-4
Group II ('C&C'='Cooperation & Control') with the Success Factors 5 and 6 as well as
Group III ('C&A'='Coping & Adaptation (of Lifestyle)') with the Success Factors 7-10 as categories or (initial) patient-categorization for the practical needs of the doctor.

2.2 Validated Patient Categorization Corresponding to the Factor Analysis 2.2.1 Complete Content-Related Correlation of NNS Classification and Factor Analysis Classification (see Part IV)

This categorization can also—just like with classical statistic methods—be conducted with a neural 'Classificator'.

The respective categorization leads to a complete concordance of contents and offers additionally a higher grade of differentiation in details while the specific advantage of neural network-systems is that this is done by the 'self-organizing system' without further programming of the software.

It was also tested whether this categorization is possible for single patient-questionnaires. The result is a definite confirmation.

2.2.2 Individual Need for Action for Each Patient

This categorization (Individual Need for Action for each Patient) is shown in the data sets for the 10 Success Factors of Diabetes Management through the four categories of 'Need for Action', as self-assessment of patients and as assessment of the medical team:

☐ red='very critical, urgent need for action',

☐ orange='critical, definite need for action',

☐ yellow='relatively well developed, some need for action',

☐ green='okay, well developed'.

The results of the NNS-analysis show that the InDiMa™-Apparatus is able to differentiate. The application of the Success Factor categorization ('red', 'orange', 'yellow' and 'green') is validated for the categorization of patients concerning Need for Action.

2.2.3 Validation of the Three Patient Categories ('E & E', 'C & C', 'C & A')

The NNS-based categorizations showed that
the distribution of the patients per Success Factor and
the distribution of the patients per group ('E & E', 'C & C', 'C & A') are independent from each other.

The result is that the distribution for each Success Factor and for each phase of development ('E & E', 'C & C', 'C & A') are validated as categorization, i.e. the NNS-based categorizations lead to the same categorization results as the classical factor analytic method.

2.2.4 More Differentiated Patient Description

As added value of the NNS method it was proven that it leads to a differentiated distribution of persons by describing the individual patterns of patient behavior in a more differentiated manner, using the seven categories of the rainbow spectrum (see www.indimasurvey.com).

The InDiMa™ Apparatus NNS analysis therefore is creating an even more differentiated individual analysis. It allows the prediction of probabilities concerning risks and chances of disease management and the combined cost for health care, based upon the NNS-based categorization.

3 Neural Network System (InDiMa™ Nns) Classificators

The NNS Classificators of the InDiMa™ Apparatus consist of 10.times.10 neurons (this is an empirically developed pattern), that have been organized as a closed cluster.

The dimensions of the input vectors for classificators are task-specific, i.e. they depend upon a the questions contained in a vector for characteristics (Success Factors) and the range of their scales (1-5 or 1-10), respectively.

4 Conditioning of the InDiMa™ Nns-System According to the 'Computing with Activities' Principle The NNS Classificators were, trained in 3,000 learning steps (the 3,000 repetitions are also empirically based steps of conditioning which were identified as adequate in NNS research, see presentation of InDiMa™ Apparatus in www.indimasurvey.com).

The Gauss-function was used as so called 'Neighboring Function' for the InDiMa™ NNS Model.

The categorization concepts laid down in the NNS Apparatus were evaluated using the principle of 'Computing with Activities'.

To build categories a 'self-learning rule' was used. For the assignment of the colors of the categories 'need for action' a 'controlled learning rule' was used (illustration of expert knowledge).

5 Structure and Development of the InDiMa™ Apparatus Program

The constructed tool, the InDiMa™ Apparatus, was developed in C++. No additional software was used.

5.1 Design of the Surface

The tool, the InDiMa™-Apparatus, consists of several surfaces which allow an individual interpretation of patient categories.

5.1.1 Step 1

The first surface layer (see FIG. 24) offers a choice for the general modus operandi; in this example, the desktop was chosen, i.e. the data is read from files.

Additionally, this modus operandi allows to choose a database (see right window in FIG. 24) from which the data is to be read.

5.1.2 Step 2

After choosing the database—in this case the database containing the 'American 10 Success Factor Study' with n=1000 patients, April 2010, was chosen. The selection of Core Instruments of the InDiMa™ Apparatus is marked by '√' (see FIG. 25: Core Instruments):

5.1.3 Step 3

After the 'Core-choice' (choice of instruments) appears working page 3 (see FIG. 26).

The user (patient=HCC or doctor and diabetes team=HCP) can activate the respective Success Factors and all the questions they contain. In the example it is done for Success Factor 1. In addition, a 'characteristics vector' for 500 persons was activated.

Furthermore, these vectors (questionnaires) have been 'trained' and 'conditioned'. They have 'learned' and have been categorized by means of so called SOM's (Self-Organizing Maps).

This categorization can also be performed as a single persons analysis. For the categorization of the individual patient, a number of persons is inserted into the field in the middle on the right side of the mask shown in FIG. 26.

By pushing the button 'Analysis' the person will be categorized with regard to his/her behavior pattern or 'position', e.g. 'Need for Action' (red, orange, yellow, green) by the InDiMa™ NNS Apparatus.

5.1.4 Step 4

Figure 27:
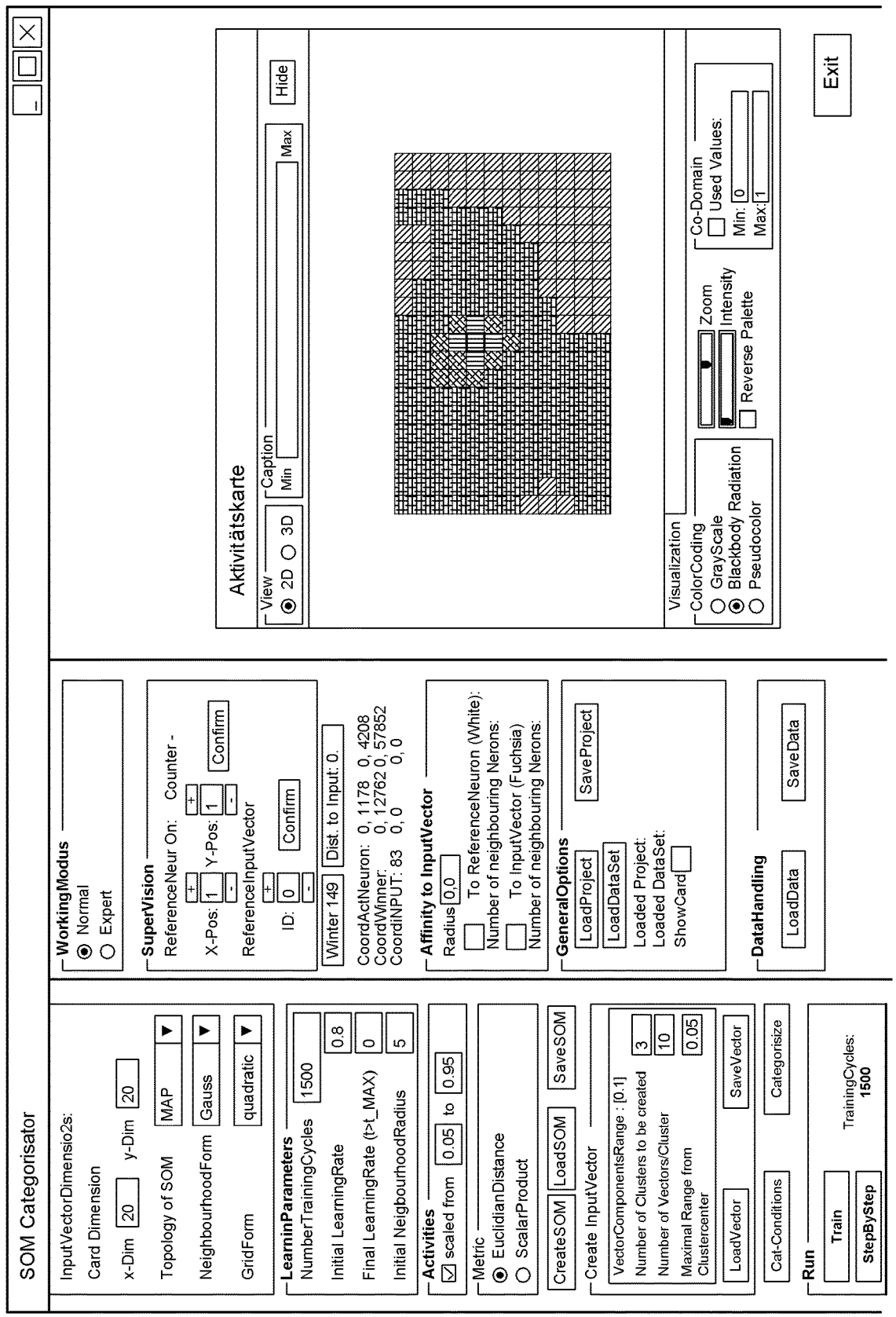
FIG. 27 is a sample screen shot of an example of a Neuronal Network System (NNS) after conditioning, showing an example success Factor 1.

In FIG. 27 the surface of a neuronal classificators (this is the patent-protected adjustment of the model parameter) is shown after its conditioning via Success Factor 1.

On the left hand side, one can see the design surface of the neuronalen network. This surface is only visible and usable when the administrator is operating on the Apparatus during the conditioning.

5.1.5 Step 5

Then the neural net of the InDiMa™ Apparatus does the categorization and shows it. See FIG. 28 for the categorization concerning Success Factor 1.

The table in the upper part and the chart below represent the result of a data set of 200 patients. The categories are engaged differently.

In the next step they are assigned to the color scheme of the InDiMa™-Model, describing the 'Need for Action' (red, orange, yellow, green).

From this categorization the HCP can see immediately how many patients are in the different categories or clusters.

Figure 28:
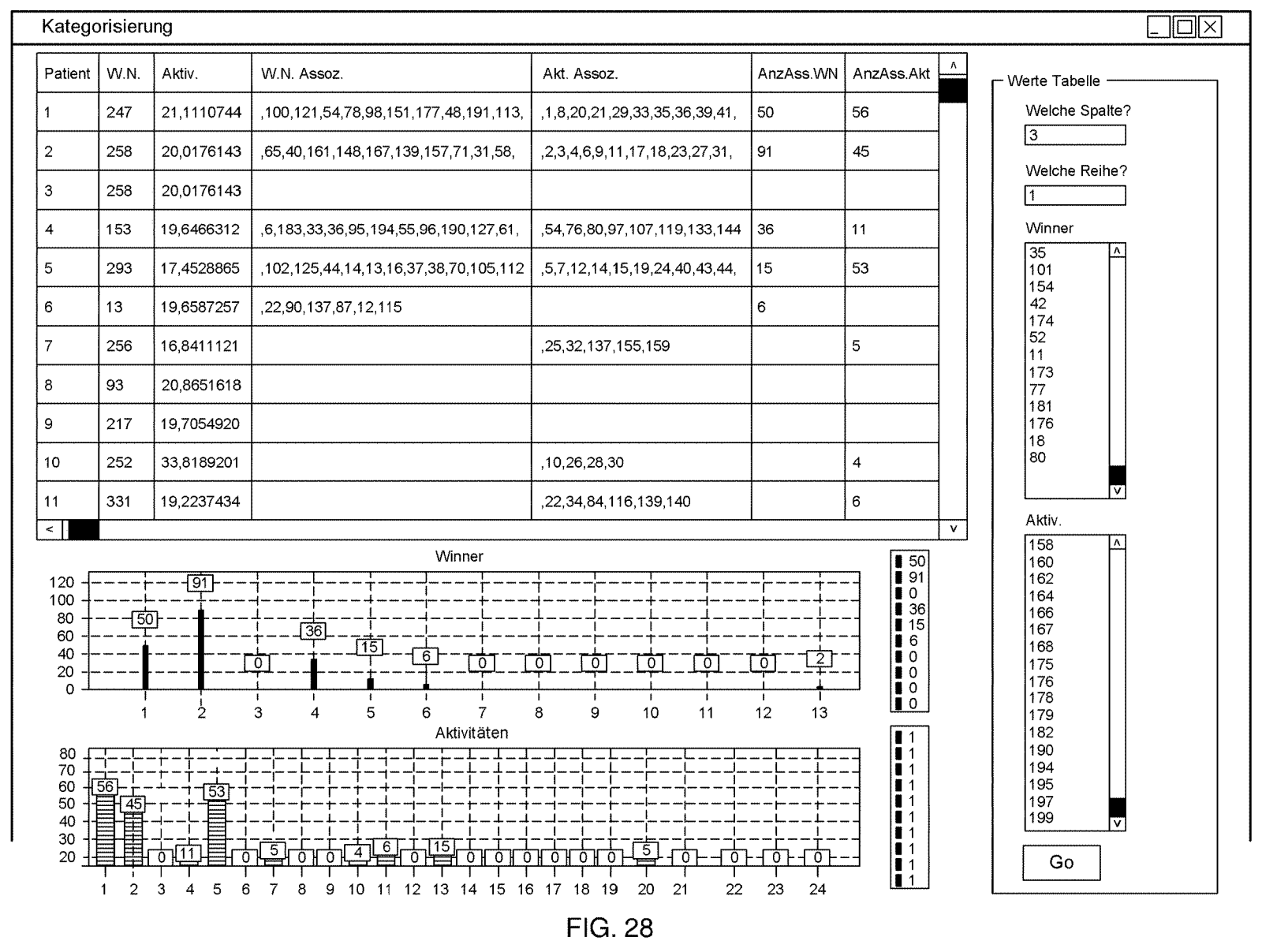

FIG. 28 shows 4 main categories or clusters with the number of assorted persons with diabetes: 50, 91, 36, 15.

If the HCP is selecting one patient from the categorization, the program will assign the person directly to one of the categories shown and communicates the result to the user (HCP), categorizing the individual patient.

6 Results of the Studies on Categorization of Diabetes Patients

6.0 Basic Research: Development of the InDiMa™ Model According the 10 Success Factors This chapter deals with creating models and the analyses of the different Success Factor and the three groups according to the empirically detected InDiMa™-Model.

After the training in the operandi 'categorization' the patient data is analyzed by the neuronal categorizer with regard to

- the number of independent categories of persons that have been found;
- the number of categories of persons kategorien that have been identified by the empirically elicited InDiMa™-Model;
- the evaluation of a model optimization.

The third aspect has to be considered for the 'learning system' in the InDiMa™-Apparatus as a continuous task.

6.1 Step 1: Cat-Conditions as Categorization Criteria of NNS (see FIGS. 29-34)

The key aspect of the work described above is the development of the so-called 'Cat-Conditions' (this describes the 'categorization radius of the neuro-mental analysis' of which the model-hypotheses and the expert knowledge of the data form a part).

Figure 29:
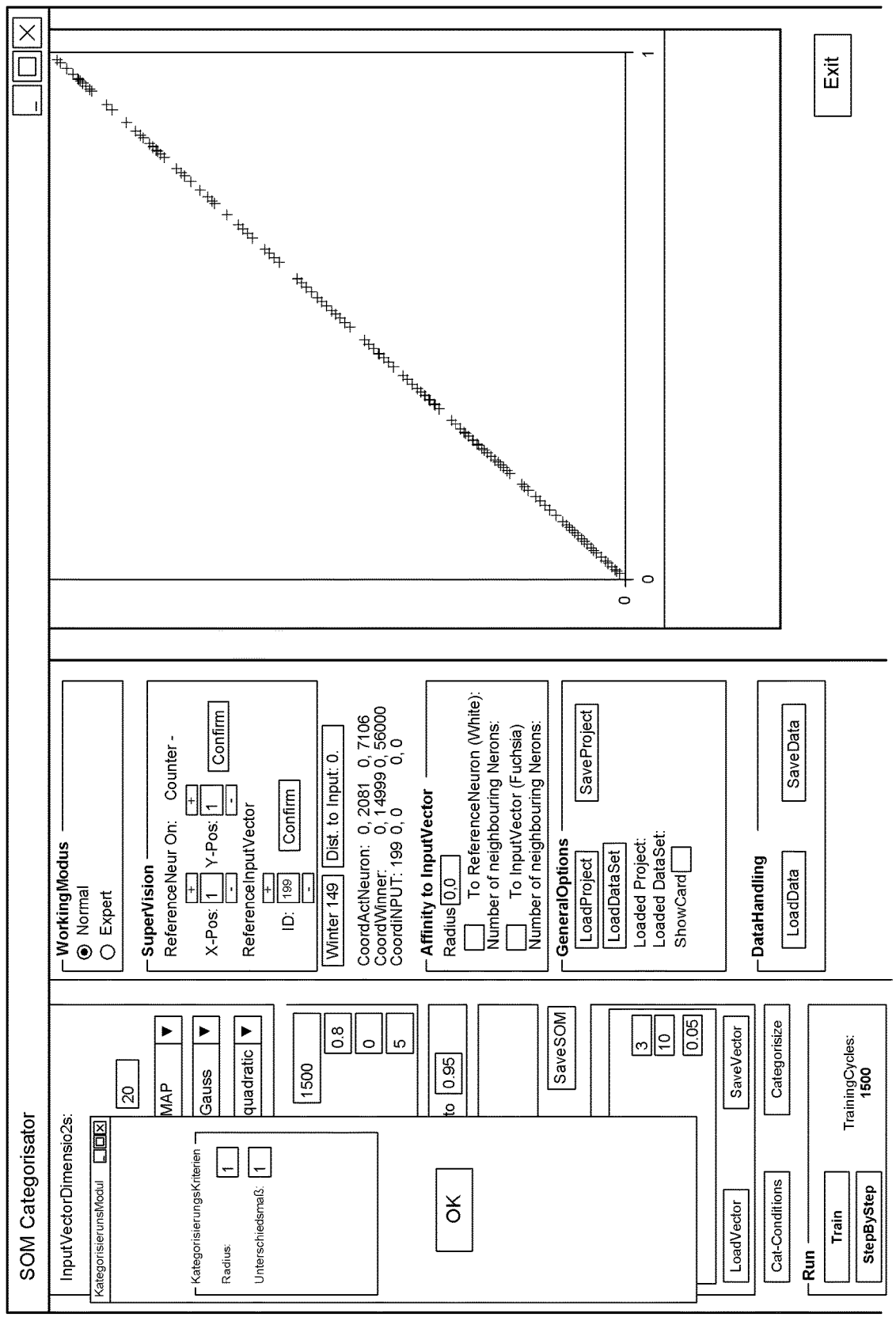
FIG. 29 is a sample screen shot of an example of a model specific adjustment of the categorization parameter, with an adjustment of the categorization radius shown for a neuron radius of 7 neurons around each winner neuron and a Cartesian distance of 1.

The 'basis model of NNS-conditioning' was used as a starting point. The adjustment of the categorization radius is shown in FIG. 29. Accordingly, a neuron radius of 7 neurons around each winner neuron and a Cartesian distance of 1 in the activity analysis of the parameter form the best reproduction of the 10 Success Factors identified in the US Studies (April 2010) and confirm the InDiMa™ model-hypotheses.

6.2 Step 2: Confirmation of the Three Patient Groups ('E & E', 'C & C', 'C & A') According to the Phases of Development (See FIG. 9)

In the next step the available patient data is analyzed by neural InDiMa™-categorizer, i.e. the patient data is scrutinized with regard to being suitable to be assigned to the higher categories.

The evaluation study showed that four categories of, need for action '(red=very high, urgent need for action, orange='high, definite need for action, yellow=need for optimization, green='okay, no need for action) developed, from which the three patient groups ('E & E', 'C & C' and 'C & A') originated.

The four main categories can be differentiated into 7-12 sub-categories.

The four patient groups according to 'need for action' (red-orange-yellow-green) could easily through adaptation of the color schemes of the InDiMa™-Model be assigned to the model-based four main categories with the 10 Success Factors.

The result of the NNS analysis per se is illustrated in FIG. 30.

In this step each person is compared with all other persons of the sample to create the categorization.

Figure 31:
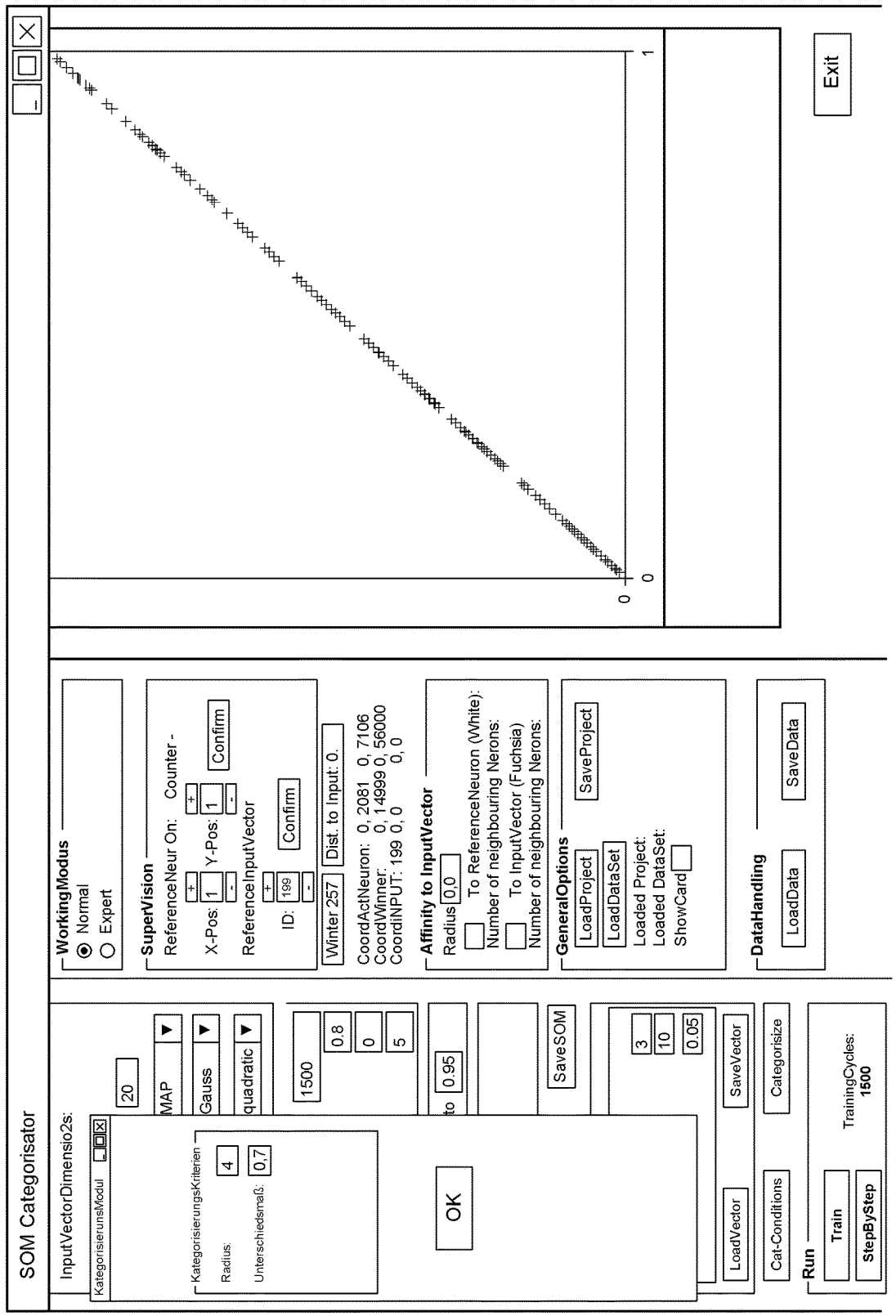
FIG. 31 is a sample screen shot of an example of a model-specific adjustment of the categorization parameter for the evolution of a more sensitive model for specific analyses of single groups.

Smaller parameters as shown in FIG. 30 lead to a more sensitive categorization. This is shown in FIG. 30:

After assigning a person to a group in the first step specific aspects can be investigated in more detail as shown in FIGS. 31-32.

Figure 33:
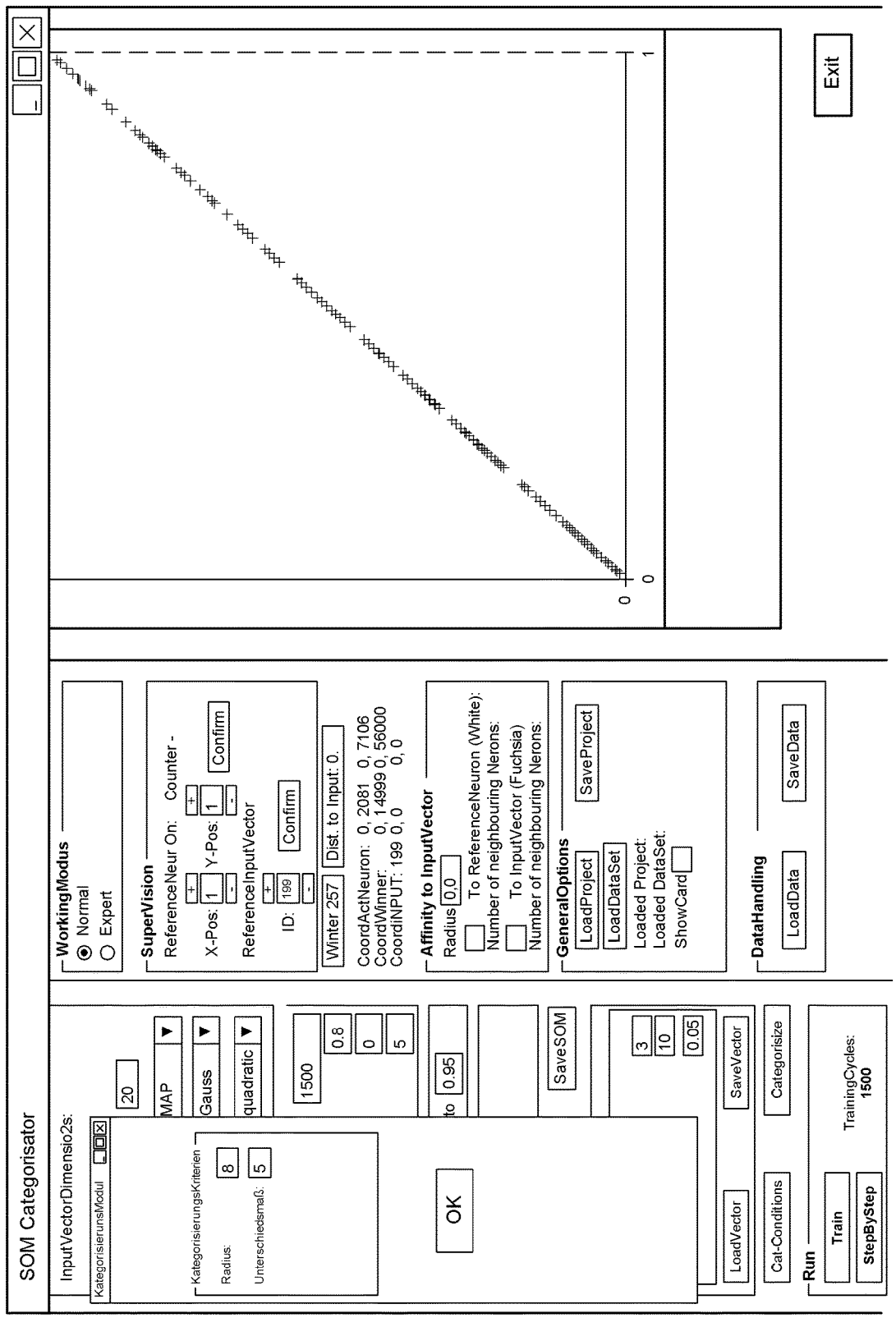
FIG. 33 is a sample screen shot of an example of a model-specific adjustment of the categorization parameter for the evaluation.
Figure 35:
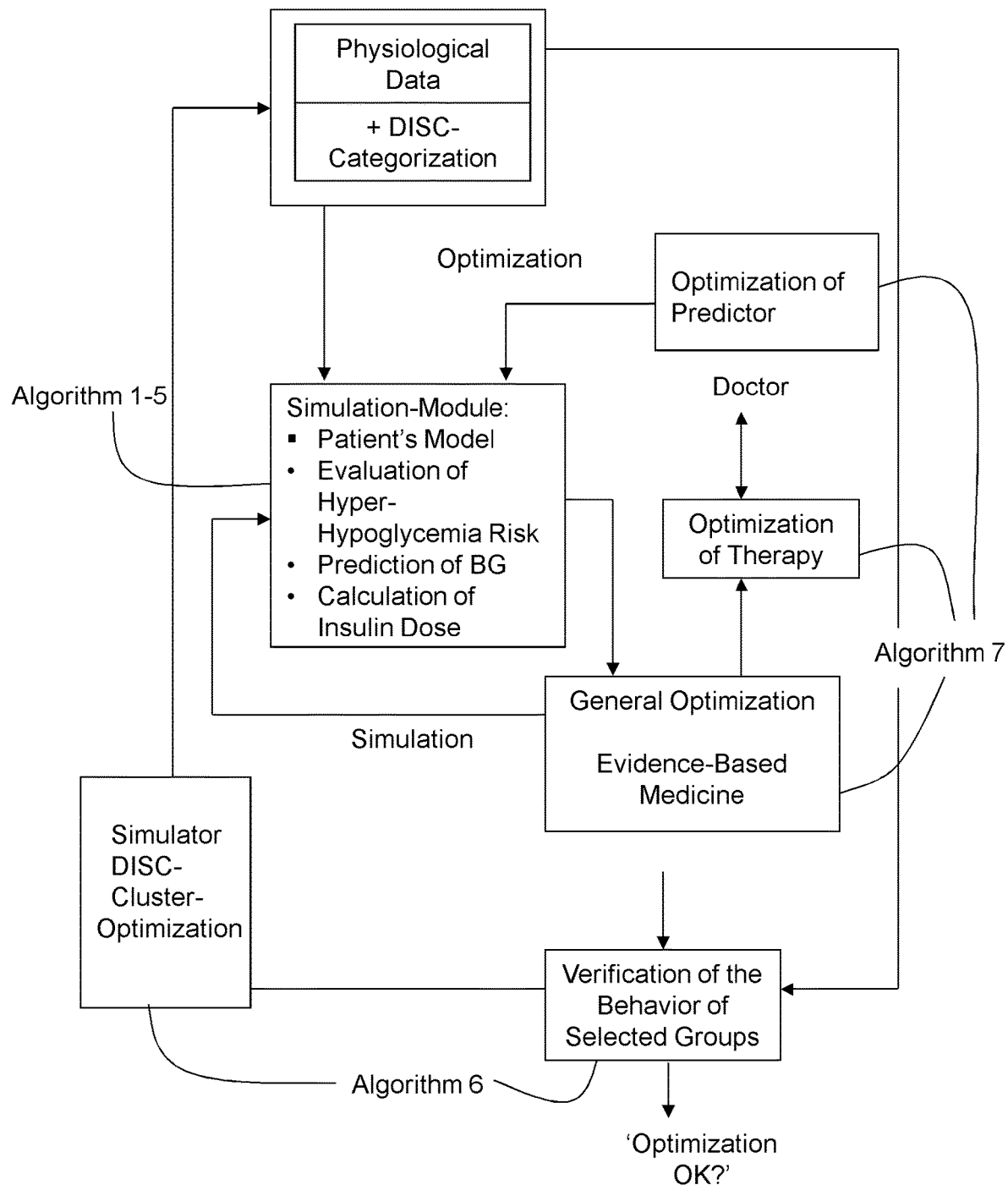
FIG. 35 is a functional block diagram for a computer system implementation of the present example embodiment showing the data flow and the calculation steps/results in a flow diagram.

Bigger parameters as shown in FIG. 33 lead to a rougher categorization as shown in FIG. 34.

3 Differentiated In-Depth Analysis Per Patient in Three Steps

In practice, the Individual Analysis will be significant: We have an individualized system focusing on the single patient.

The group analysis respectively the categorization of patients show its practical value in the field of 'efficiency for doctors': First of all, a 'rough pre-selection' is made for the doctor in which the overall situation of the patient is shown.

The in-depth analysis is realized in three steps:

7.1 Step 1: The Overall Situation of the Patient

Display of the overall situation of the patient including all 10 Success Factors in a 'neuronally defined paint dot'.

The colors 'green'='okay' to 'red'='very critical situation, urgent need for action' as well as the colors in between 'orange'='critical' and 'yellow'='to be optimized' offer a graphic overview on the overall situation of the patient.

7.2 Step 2: Categorization According to the Three Main Medical Stages

The three main medical categories are according the three stages of diabetes management:

Stage 'E & E' ('Empowerment & Enabling'): Regularly patients with eating addiction and weight control problems, often with adiposity, who lack motivation ('Empowerment') and knowledge about self-therapy ('Enabling') and especially where the interrelation of both of them (motivated to actively change their situation and to adapt to the challenges of diabetes management) is problematic.

This can be done in a third step for each Success Factor by means of an individual analysis.

Before that, in step 2, a categorization is performed:

Stage 'C & C' ('Cooperation & Control') of Success Factors 5 and 6 in connection with 'Empowerment' and 'Enabling' by the doctor:

On one hand trust and openness about diabetes management problems and control of the three medical core criteria (blood pressure, cholesterol/lipids, and blood glucose control), on the other hand an understanding and not judging doctor who is taking into account the specific needs of the patient who can motivate (='Empowerment') and actively supports the patient in coping with diabetes (='Enabling').

Stage 'C & A' ('Coping with Diabetes & Adaptation [of Lifestyle]'): Patients who are able to control to a large extent the medical and psychological problems of diabetes and to adapt their lifestyle according their diabetes.

7.3 Step 3: Individual Analysis

There are four different factors that can be analyzed for each Success Factor in step 3:

Success Factor 7: Does the patient know about the focus for improvement needs in his self-care?

Success Factor 8: Does the doctor (from the patient's point of view) offer an individualized specific medical help and support?

Success Factor 9: How good is the quality of self-care and the overall status of health of the patient? Where is potential for optimization in detail and how can it be achieved?

Success Factor 10: How is the quality of life, the overall status of health as well as the psychological condition for coping with the diabetes reality in the long run (avoidance of depression and burnout)?—This is significant for the genetically determined diabetes type 1 since the necessarily bio-physical and bio-medical adaptation to diabetes is given (otherwise they will die).

8 Comprehensive Nns Analysis and Cross-Check

If one analyzes every single Success Factor, one can see that the Success Factors have a different distribution.

A rough analysis according to the model herein shows the following results, as shown in Table 4:

9 Summarizing Analysis of Categorizations (1) Confirmation of the Four 'Need for Action' Criteria ('Red', 'Orange', 'Yellow', 'Green') by the 10 Success Factors The analysis of each individual Success Factor shows as result that all Success Factors have the same 'distribution pattern' (with the categories 'red', 'orange', 'yellow' and 'green').

(2) Individual Analysis of the 10 Success Factors

Combining a plurality of Success Factors the NNS-analysis shows that the factors do not lead to the same creation of categories beyond the 10 Success Factors.

This means that the individual Success Factors—as was already proven by the factor analysis—is statistically more or less independent from each other.

The categorization ('red', 'orange', 'yellow' and 'green') has to be performed for each of the 10 Success Factors: It cannot be performed by the same categorizer in one step for all 10 Success Factors.

(3) Linear Independence of the 10 Success Factors

There are groups of persons which are displayed differently on the 10 Success Factors (e.g., Success Factor 1 'green'='high social support', but for Success Factor 10 showing 'red'=, 'not coping with diabetes at all').

Therefore, by the analysis of the InDiMa™ neural network system, it is proven that the 10 Success Factors are in the state of linear independence.

This confirms the 'Need for Action' categorization of the InDiMa™ model which was determined by classical factor analysis (see: www-indimasurvey.com: studies IS2 and IS3).

(4) Significant and Medically Relevant Results for 'Individualized Diabetes Management'

In Table 1 the different Success Factors and their significantly relevant categorizations are displayed:

The size of the significances is related to the size of the sample: Highly relevant significances are identified as 'statistically relevant' even if the sample is relatively small.

TABLE 4

| Success factor | red w | red a | orange w | orange a | yellow w | yellow a | green w | green a |
|---|---|---|---|---|---|---|---|---|
| 1 USA | — | — | 114 | 154 | 41 | 32 | 42 | 4 |
| 1 Germany | 57 | 91 | 42 | 61 | 92 | 27 | — | — |
| 2 USA | — | — | 62 | 17 | 43 (130)* | | 7 | 3 (130)* |
| 2 Germany | — | — | 47 | — | 56 | 81 | 93 | 100 |
| 3 Germany | — | — | 7 | — | 49 | 62 | 131 | 112 |
| 4 USA | 72 | 69 | 72 | 69 | — | 13 | 53 | 40 |
| 4 Germany | 8 | _ | 5 | 17 | 9 | 3 | 174 | 158 |

*Mixed class

Table 5 serves as a cross-check:

TABLE 5

| Color | % winner-related | % activity-related |
|---|---|---|
| Red | 0.097 | 0.114 |
| Orange | 0.25 | 0.23 |
| Yellow | 0.25 | 0.36 |
| Green | 0.36 | 0.35 |
| Sum | 0.96 | 1.05 |

This is the case for all categorizations of 'Need for Action' which are significant for all patient groups and for all three stages of diabetes management:

'E & E'='Empowerment and Enabling',

'C & C'='Cooperation and Control',

'C & A'='Coping with Diabetes and Adaptation (of Lifestyle)'.

An enlargement of the sample led to all categories being proven 'significant'.

10 Summary of the Experimental Results 10.1 Confirmation of the Four 'Need for Action' Criteria of the Indima™ Model Both, the winner-related analysis (first generation of NNS-analysis) and the activity-related analysis (third generation of NNS-analysis), confirm the validity of the 'Need for Action' mode.

Four 'Need for Action' categories of the InDiMa™ Diabetes Management system were validated for each one of the 10 Success Factors.

One more category is added which shows that the questionnaires have not been filled in completely by the patients. This is also a relevant information, since not filling out the questionnaire is in many cases an indication for a 'Need for Action' category and for a 'Personal Interview' of the patient by the doctor or the medical team.

10.2 'Need for Action Sensitivity' and 'Completion Sensitivity' of the Indima™ Apparatus From this finding and the prior analyses, the two advantages of the chosen neural approach become apparent:

(1) The neural classificator is model-based variable.

This means that the InDiMa™ NNS categorization radius can be compared for different models with the same categorizer. This makes an evaluation of the models possible.

This means the NNS-classificator is 'model-sensitive' and can at any given time applicate rougher ('need for action' vs. 'no need for action') or more sensitive models (e.g., seven instead of four categories of 'Need for Action') and test them in comparison.

Classical categorizers can only do this to a certain degree, e.g., new calculations, restructuring or manual improvements.

(2) The neural classificator is 'completion-sensitive'. Classical categorizers can only do this to a certain degree, e.g., by manual improvements.

Concerning the categorization results of the three groups 'C & C', 'E & E'. and 'C & A' it is remarkable that especially within Group III 'C & A' the four individual Success Factors (SF 7, SF 8, SF 9, SF 10) have to be analyzed individually.

This can be explained by the fact that through the non-linearity, i.e., independence of the Success Factors whose amalgation in main categories (secondary factors) brings a model-conform result, but—as in well known classical statistical analysis—a differentiated analysis of the four Success Factors (SF 7-10) per patient brings a differentiated impression with relevant additional information.

10.3 Innovative 3-Step-Approach of the Indima™ Apparatus

The InDiMa™ Apparatus is ready for practical use of the doctor, the medical team, the administrator in the health care ministry, the manager of a hospital or for the use by the interested patient for his self-analysis and the preparation of an 'Individualized Action Program':

Step 1: Comprehensive overall picture: Categorization of the patients in Group I ('E & E'), Group II ('C & C') or Group III ('C & A')

Step 2: Analysis of the specific selection out of the '10 InDiMa™ Success Factors' (per patient or per group)

Step 3: Differential Analysis per Success Factor on item basis for the 'Individualized Action Program' of the patient or the specific patient group 2 Detailed Description of the "InDiMa™ Apparatus" Example Embodiment Example 2: Application for Precise Glycemic Control in Individualized Diabetes Management The example embodiment makes it possible, without being limited thereto, to create precise methods for the evaluation of predictive diabetic's glycemic control, and includes firmware and software code to be used in computing the key components of the method. The inventive methods for evaluating BG, the long-term probability of SH, and the short term risk of hyperglycemia and hypoglycemia, are also validated based on extensive data collected, as will be discussed later in this document. Finally, the aspects of these methods can be combined in structured display or matrix form.

2.1 Creating a Computer Based Memory of Individual Patient's Medical Records

Specifically for the example embodiment, a microcomputer system is controlled by a program stored in a permanent memory on the hard disc drive (secondary memory) of a computer in such a manner that the following method steps may be carried out: Controlled by an internal or external clock, binary-encoded sensor and categorization data on a patient are supplied to a microcomputer system, which converts these data to a vector form in a defined sequence. The vector is called the patient status data vector (PSV). The PSV represents the patient to be assessed and treated by his blood glucose, the ingested carbohydrate divided in the three classes fast, medium and slow carbohydrate and the parameters of his self-control test described below.

To create an individual experience-based model of the patient, a sufficiently large number of physiological or psychological states/data for example from the InDiMa™ questionnaire have to be integrated in the model using the patient status data vector (PSV), with components resulting from the data mentioned here. Furthermore, it may be assumed that a causal relationship exists between a personal system state at time t and a personal system state t+Δt, when Δt is sufficiently small. This means, however, that the denser a stored time history—defined via Δt—is of all patient system states, the more complete the experience-based model of the patient is, and, as a consequence of the causality of the personal system behavior, the more complete the ability of the patient model is to predict future states of the patient and, therefore, to intervene in his physiological state in order to bring it under control. For this to be accomplished, however, all possible patient states and future states based thereon have to be stored in a symmetrical manner done by recording the patient's state vectors over long time and diverse life situations. Also, known patient's situations as hyperglycemia and hypoglycemia states have to be stored in this symmetrical manner which can be done by simulated PSV also.

In an inventive refinement of the current technology, an expanded, computer-aided memory model for these large amounts of stored PSV's is used, which serves to combine a combination of computer-aided estimators (neurons) into a neuronal network. These estimators are coded in a way that they are placed on a topologically closed, two-dimensional surface such as the torus-like surface shown in FIG. 42 on a regular or irregular grid formed of the estimators. In a first advantageous embodiment, it is thereby made possible to assign the same number of adjacent estimators to every estimator. This means it is possible to assign the same number of similar system states in a topologically adjacent manner to every personal system state that is categorized by the values of the estimators. Fringe effects and cut-off effects, which are known from the literature, may therefore be avoided, i.e., all of the estimators as a whole may categorize system states in a continual manner (See Reuter: Computing with Activities, Computational Intelligence, LNCS 2206: 174-184, 2001 (the contents of which are incorporated herein by reference)).

Figure 43:
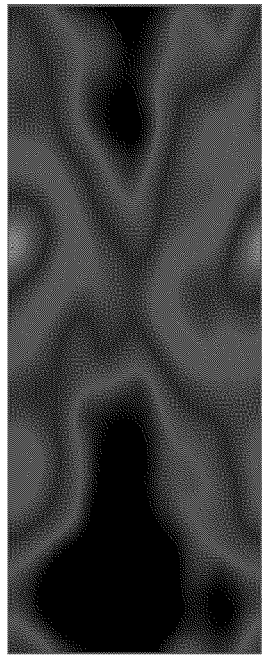
FIG. 43 is an exemplary activity pattern of a closed neural net structure representing a patient's behavior in the context of diabetes.
Figure 44:
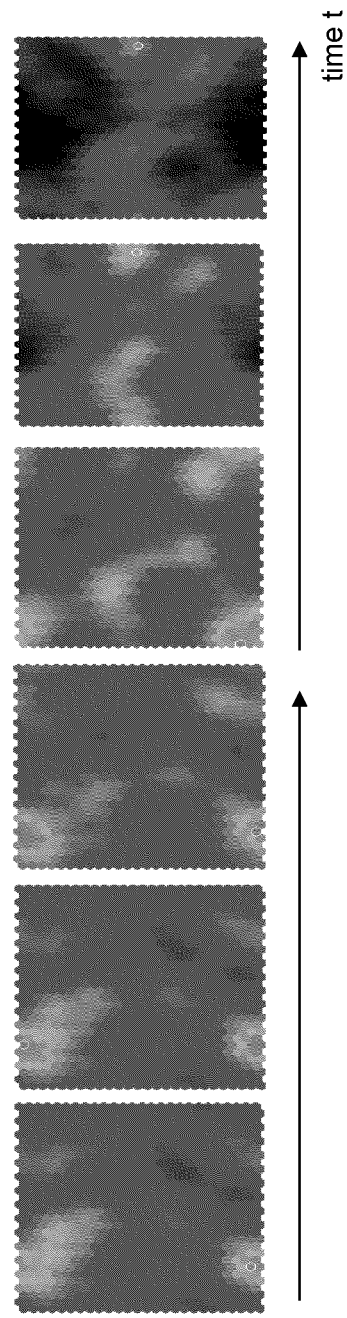
FIG. 44 is an example for a smooth and continuous change of the activity pattern of a closed neural net structure if the patient's state changes with time t.
Figure 42:
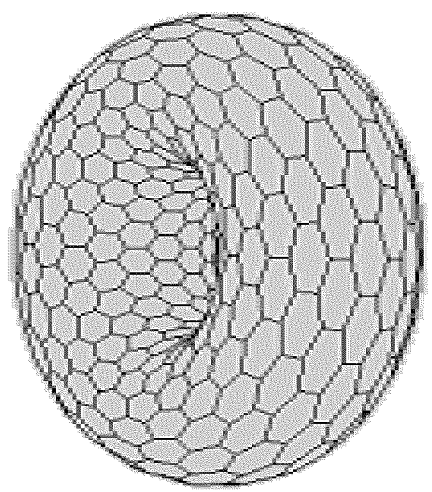
FIG. 42 is an exemplary topological form of a closed neural net structure.

In a further embodiment of the present example embodiment, the actual categorization of system states is not carried out using only one selected estimator, e.g., the estimator with the highest output value, but the activity of all estimates, as shown in FIG. 43. So the activity pattern of the whole torus represents the categorization of a PSV, i.e., the matrix of all estimates represents a system state. Using this kind of categorization, it is possible to encode a larger number of distinguishable categorizations as known before, e.g., using 10 times 10 estimators and a band width of their estimates of 16 bit, $10^{24}$ PSV's.

To create the experience-based model of a patient itself, diverse PSV's are presented to the neural net described above in its selectable "conditioning" operating state. These PSV's may represent real patient states recorded over the time or PSV's which have been created in a reasonable, synthetic manner, i.e., simulated or designed on the basic of medical knowledge. During this conditioning phase of the neural net—which is controlled via the mathematical conditioning formula of the "Self-Organizing Maps" (SOM's)—the structure of the estimators is modified such that the neural net/network formed by them store the presented patient's states in its structure in a way that they may be called up in a defined kind. In detail and common to the theory of the neural nets, this may take place by changing the connection weights between the estimators of a first estimator layer—which represents the patient status data vector components (PSV components)—and the elements of a second estimator layer, which perform the actual categorization. This procedure is known as the self-organizing-principle of simulated neural maps with N estimators, briefly named "Self-Organizing Maps (SOM's). (See book of Kohonen T.: Self-Organizing Maps, 1995 (the contents of which are incorporated herein by reference)) and can be formulated briefly by the formulas, Equation 1

$$\Delta_x(x_j^t, w_s^t) = \min\{\Delta_x(x_j^t, w_s^t) | i=1, \ldots, N\} \quad \text{Equation 1}$$

whereby $\Delta_x(x_j^t, w_s^t)$ denotes the difference between the presented PSV $x_j^t$ at an given time t out of an ensemble with the serial number j and $w_s^t$ the weight vector from all estimators of the first layer to the estimator s with the largest activity. Next, the weights of all estimators are adapted regarding the estimator of largest activity by the formula Equation 2

$$w_i^{t+1} = w_i^t + \varepsilon^t \cdot h_{si}^t \cdot \Delta_x(x_j^t, w_i^t) \quad \text{Equation 2}$$

with the time-dependent learning rate ε, Equation 3

$$\varepsilon^t = \varepsilon_{start} \cdot \left(\frac{\varepsilon_{end}}{\varepsilon_{start}}\right)^{\frac{t}{t_{max}}} \quad \text{Equation 3}$$

the neighborhood function $h_{si}^t$, Equation 4

$$h_{si}^t = e^{\frac{-\Delta^A(k_s, k_i)^2}{2(\delta^t)^2}} \quad \text{Equation 4}$$

and the adoption function $\delta^t$, Equation 5

$$\delta^t = \delta_{start} \cdot \left(\frac{\delta_{end}}{\delta_{start}}\right)^{\frac{t}{t_{max}}} \quad \text{Equation 5}$$

is used.

The variable "start" denotes the values of the time-dependent parameters at the beginning of the conditioning operation state, "end" the values of the time-dependent parameters at the end of the condition operation state and $t_{max}$ the maximum number of conditioning operation state steps to be calculated.

In this way, all PSV's are coded in the weight structure of the neural net if the conditioning operating state is finished, whereby similar PSV's correspond to similar activity patterns of the net.

Due to the structure of the second estimator layer described, it is possible to store all presented sensor and categorization vectors and therefore, patient states, in constant form in the estimator-based and therefore in an experience-based model and, therefore, due to the adjacency of causally successive patient states, to define a causal chain of events via the second estimator layer using its related modification of its estimators. Due to the mathematical conditioning formula and the large memory capacity, the categorizing neural network may be continually modified without losing its previously-stored structure. As such, it is possible to expand a system model continually, in an adaptable, experience-based manner (See Reuter: Ruling Robots by the Activity Patterns of Hierarchical SOMs, ISC'2003 (Eurosis03), 2003 (the contents of which are incorporated herein by reference)).

Due to the structure of the neural nets in a selectable "classification" operating state, PSV's can be categorized if the neural net is conditioned by some basic vectors or by a complete set of the patient status data vectors, whereby the quality of the result of the categorization depends on the density of the different statuses already coded in the neural net during the condition state. This recall takes place in that way, that an activity pattern of the neural net neurons $\Phi_{(t)}$ for a given time t corresponds to one and only one PSV at the same time t and that similar activity patterns $\Phi'_{(t)}$ of the neural net correspond to similar PSV values. In detail in the classification modus of the net, a PSV is presented by the network by presenting the components of the PSV to the first layer of the neural network. Based on its special—learned—structure, the second—classification—layer of the network will be induced to an activity PSVs2 which is similar or equal to the activity PSVs1 which has been stored before in the conditioning state whereby the difference between PSVs2 and PSVs1 is coded in the different activity patterns $\Phi_{(t)}$ of the neural net when PSVs2 or PSVs1 is presented to the neural net. This difference will be as larger as larger the difference between PSVs2 and PSVs1, whereby the mathematical dependence of this difference depends on the chosen neighborhood function $h_{si}^t$. In that way, even PSVs that have not yet been presented, but are assigned to patient states stored in the model to an extent defined in the conditioning formula, will be categorized so that a continuous chance of activity patterns over the time denotes a continuous change of a patient's state over the time t.

In a further advantageous embodiment of the present example embodiment, the activity patterns $\Phi_{(t)}$ categorizing the patient's or the patients' states can be decoded by a second kind of neural nets following the backpropagation scheme and displayed on a monitor or announced by a loudhailer. Thereby the backpropagation net is trained in that way, that an activity patterns $\Phi_{(t)}$ is assigned to a patient status PS(t). The appropriated backpropagation net consist of three layer of estimators, whereby the first layer—the input layer—gets the activity patterns $\Phi_{(t)}$ from the first net in a one to one way, the second layer—the hidden layer—transform the activity pattern in a new neuro-mental representation and the third—the output-layer—represents the probability of the patient's statuses via several estimators, whereby every estimator represents one patient status.

Due to the structure, all calculated and measured values will be stored on a hard disc drive or a removable storage drive for later use.

Due to the structure described in the previous paragraphs, it is possible to categorize every PSV, and a medical report reps. a trend analysis of the patients diabetes status can be calculated by combining several $\Phi_{(t)}$, resp. PS(t) in chronological order. The resulting time trajectory of the PS(t) then describes varying diabetes statuses, resp. the diabetes value history over selectable time windows which can be visualized or explained in an acoustic way. In that way, the patient can control himself resp. his course of disease/therapy.

2.2 Creating a Computer Based Predictor for BG Estimation

Alternatively, the example embodiment provides a method, system and computer program product for predicting one or several patient's physical or psychological parameters via a predictive control module. This predictive control module is constituted by a neural chain of estimators, whose principle hierarchical structure is the same as described above, whereby this chain now is used to calculate the patient states and/or the BG and/or both to be expected in the near or far future, with the help of his individual personal model.

For this propose, the components of the PSV's of a selectable time window T—represented by an independent measured PSV's—are combined in any order to a new (enlarged) personal status vector EPSV. Representing the history of the patient's status in the time-window T, this EPSV forms one of the diverse EPSVs which are used to create an experience-based model of the patients time behavior in the same line as described above. Also in the same line as described above, this model will be decoded by the second net structure, whereby the output of this structure now will be a predicted value/parameter or directive, for example the BG-value to be expected in the next hours.

Next, on the basis of these predicted values/parameters or directive or machine command, a patient directive or a simple record will be created, whereby due to the structure of the method, system and computer program product, a special interface for an external expert system guarantees that the predicted values/parameter or directive can be adequately transferred to medically sensitive machine commands, patient directives or records.

Due to the structure, the "conditioning" operating state may be activated during on-going operation or during any periods of time for all neural nets and in this, the ascertained nets may be validated by a rule-based optimization algorithm whether they still satisfy a given categorization standard or whether they have to be sensitized, to optimize the categorization system.

2.3 As Example of the Indima™ Apparatus Application for Diabetes Management: Evaluation of Patient's Type by Self-Assessments or External Assessments In a further advantageous embodiment of the present example embodiment, the patient's medical and physiological status is linked with data that are measurable via electronic means and which were obtained via self-assessment or external assessment (by the patient, physician, or diabetes experts) in the "Patient DISC/IDEA Test" (or in other psychological and psychological tests like InDiMa™). This enables a standardized prognosis of the course of the specific patient's condition, an individualized prognosis that takes into account the patient's pattern of behavior, which was ascertained electronically (psychologically and empirically on a patient typology determined via random sampling).

In a further advantageous embodiment of the present example embodiment, the consultation and patient-care style of the treating physician and the consultation and patient-care style of the patient's other diabetes care providers are linked with the standardized prognosis determined from the medical-physiological data, psychological data and the individualized prognosis per patient based on his behavior style (empirical-electronic categorization based on the DISC model or other models). As a result, the individualized, patient-specific prognosis of the course of his condition becomes an individualized, therapeutic recommendation model for controlling the individual patient (with his empirically ascertained and predicted patterns of behavior). This individualized control, which requires minimal effort (since it is ascertained electronically and in an individualized manner, and is linked with a predictive rule), results in a precise, individualized prediction of the patient's behavior, and of the opportunities and risks he will face in his diabetes self-management (compliance).

In addition, information about an individual's self-control (per the "DISC"/"IDEA" Style) and a) a general training package ("Personal Interaction Training"="PIT") for the diabetes care provider, and b) a patient-specific recommendation for behavior are generated electronically for the treating physician and/or other diabetes care providers (nutritionists, psychologists, other medical personnel who are providing medical care that may affect organs in a diabetes-related manner, etc.). The resultant, significant improvement in a patient's behavior in diabetes therapy (compliance), and the resultant patient-specific, individualized support by this patient's diabetes care providers ("Individualized Diabetes Therapy") serve to significantly improve the success of diabetes therapy, to protect life (improving the quality of life and life expectancy), and, ultimately, to help reduce the costs of health care, which benefits society as a whole.

In a further advantageous embodiment of the present example embodiment—as another example, but not limited hereto—the patient's behavior style (determined based on the DISC/IDEA categorization system) is related to his "social balance" style, his accuracy in following therapeutic instructions (treatment and adherence), and the success of his therapy (course of glucose values over time: glucose training). The "Patient Style Prediction" (PSP) indicator is generated. In all, the three parameters of the physician's behavior style of patient management, the physician's "social balance", and the physician's compliance management are used to predict the success of therapy based on the "Therapy Style Prediction" (TSP) indicator based upon the self-assessment data of physician and patient as ONE example of the InDiMa™ System Application. The physician-patient interaction that may be derived from these indicators is analyzed based on the IPS data and using the electronic prognosis that was obtained. It is then incorporated in a DISC/IDEA optimization catalog—which was processed electronically—with four main types (DISC=Driver-Introspective-Supportive-Cooperative/ IDEA=Introspective-Driver-Expressive-Amiable) and 4×4=16 subtypes (DISC/IDEA test, evaluation scheme) for the patient and for the physician.

Personal Interaction Training (PIT) for the physician (depending on the type) and for his patient (depending on the type) in the form of computer-aided instruction is thereby made possible.

The three data records named above, i.e., D1=scale of proactive dynamics/dominance (PDD), D2=scale of emotional and communicative openness (EKO), D3=compliance scale (TZ), and the additional scales D4=social balance and flexibility scale (SBE) (D1, D2, D3 and D4 as the prediction group), including a "lying scale" (D5) for realistically correcting the patient's claims about his eating habits (D6=bolus optimization) are continually refined (D7=prognostic values) and reconciled with the actual data (D8) (validation values: D9).

In a further advantageous embodiment of the present example embodiment, the neural estimators are divided in several modules estimating the several linear independent psychological items resulting from the InDiMa™ questionnaire. By this way, a more complex estimation of crossing items between several psychological basis items can be ensured and the personal vector carries/conveys more structured information.

In a further advantageous embodiment of the present example embodiment, the results of the different neural estimators are estimated by a hierarchically higher neuronal neural based "integrator" to an overall estimator of the patient's status.

In a further very advantageous embodiment of the present example embodiment ("ADVICE"), the sum of all individual patient diagnoses based on a physician or a team of physicians is designed as a "learning system" or an electronically connected "Diabetes Management Network", which—connected via computers, PC's, the internet, and eventually, cellular phones—provides the physician with a computer-aided and wirelessly-supported, therapeutic learning curve that is optimized continually, thereby guaranteeing an asymptotic approximation of optimal diabetes therapy.

Also, a related optimization of the patient's behavior ("SMART") with accuracy of the data, (personal compliance) may be realized in one of the above advantageous embodiments of the present example embodiment.

2.4 Exemplary Systems

Figure 36:
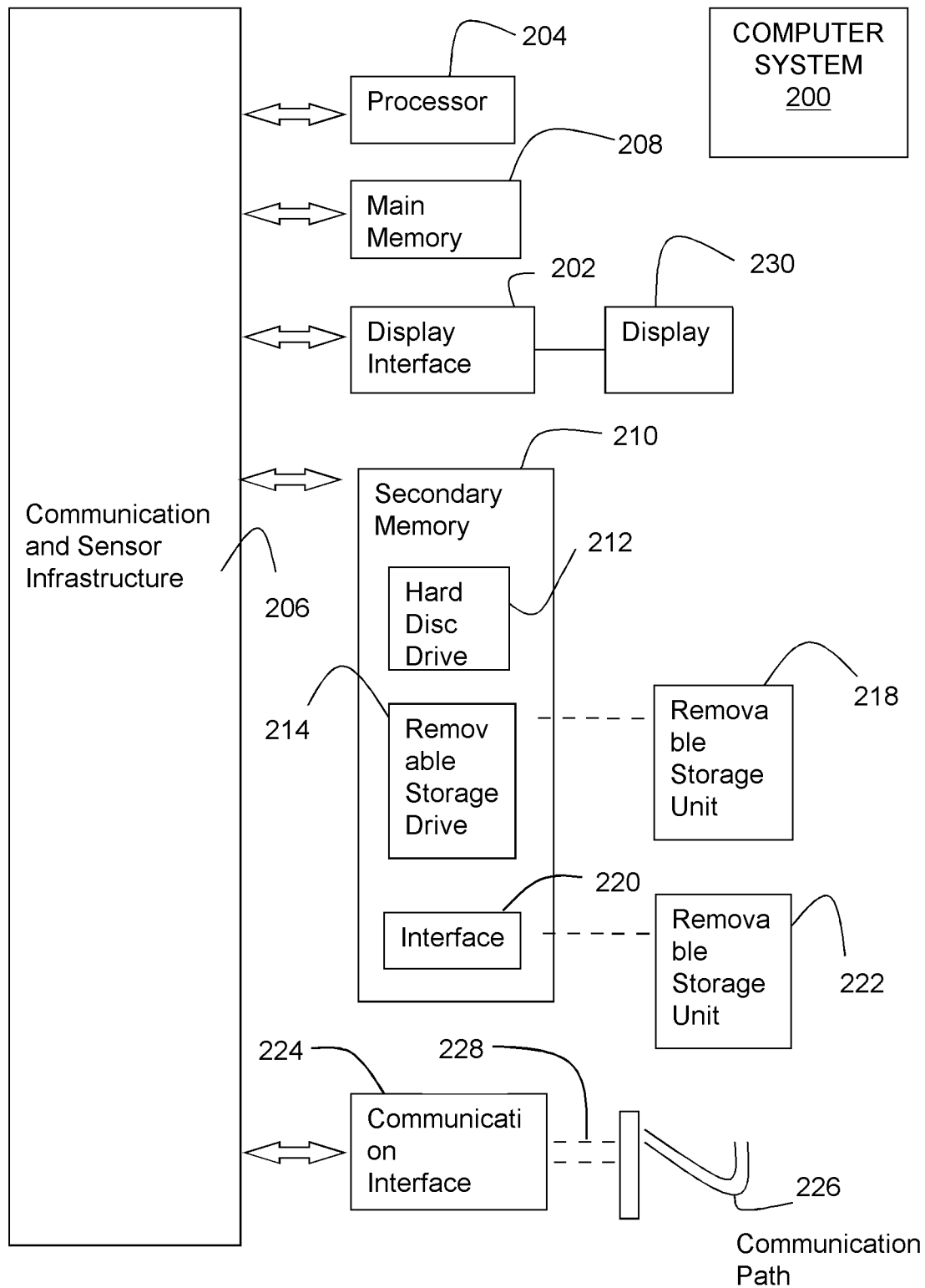
FIG. 36 is a functional block diagram for a computer system implementation of the present example embodiment.

The method of the example embodiment may be implemented using hardware, software or a combination thereof and may be implemented in one or more computer systems or other processing systems, such as personal digital assistants (PDA's), in blood glucose self-monitoring devices (SMBG memory meters), or systems which administer insulin to a patient; if adequate, memory and processing capabilities are available. In an example embodiment, the example embodiment was implemented in software running on a general purpose computer 200 as illustrated in FIG. 36.

Computer system 200 includes one or more processors, such as processor 204. Processor 204 is connected to communication infrastructure 206 (e.g., a communications bus, cross-over bar, or network). Computer system 200 may include a display interface 202 that forwards graphics, text, and other data from the communication infrastructure 206 (or from a frame buffer not shown) for display on the display unit 230.

Computer system 200 also includes a main memory 208, preferable random access memory (RAM), and may also include a secondary memory 210. The secondary memory 210 may include, for example, a hard disk drive 212 and/or a removable storage drive 214, representing an optical disc drive, a floppy drive, a magnetic tape drive, a flash memory, etc. The removable storage drive 214 reads from and/or writes to a removable storage unit 218, representing an optical disc drive, a floppy drive, a magnetic tape drive, a flash memory, etc. which is read by and written by removable storage drive 214. As will be appreciated, the removable storage unit 218 includes a computer usable storage medium having stored therein computer software and/or data.

In alternative embodiments, secondary memory 210 may include other means for allowing computer programs or other instructions to be located into computer system 200. Such means include, for example, a removable storage unit 222 and an interface 220. Examples of such removable storage units/interfaces include a program cartridge interface (such as that found in video game devices), a removable memory chip (such as a ROM, PROM, EPROM or EEPROM) and associated socket, and other removable storage units 222 and interfaces 220 which allow software and data to be transferred from the removable storage unit 222 to computer system 200.

Computer system 200 may also include a communications interface 224. Communication interface 224 allows software and data to be transferred between computer system 200 and external devices. Examples of communications interface 224 may include a modem, a network interface (such as an Ethernet card), a PCMCIA slot and card, etc. Software and data transferred via communications interface 224 are in the form of signals 228 which may be electronic, electromagnetic such as optical, or other signals capable of being received by communications interface 224. Signals 228 are provided to communications interface 224 via a communications path (i.e., channel) 226. Channel 226 carries signals 228 and may be implemented using wire or cable, fiber optics, a phone line, a cellular phone link, an RF link, an infrared link, and other communications channels.

In this document, the terms "Computer Program Medium" and "Computer Usable Medium" are used to generally refer to media such as removable storage drive 214, a hard disk installed in a hard disk drive 221, and signals 228. These computer program products are means for providing software to a computer system 200. The example embodiment includes such computer program products.

Computer programs (also called computer control logic), structures of neural nets and DISC/IDEA evaluation schemes are stored in main memory 208 and/or secondary memory 210. Computer programs and structures of neural nets may also be received via communications interface 224. Such computer programs, when executed, or such neural net structures or DISC/IDEA evaluation schemes, when used, enable computer system 200 to perform the features of the present example embodiment, as discussed herein. In particular, the computer programs, when executed, enable processor 204 to perform the functions of the present example embodiment. Accordingly, such computer programs represent controllers of computer system 200.

In an embodiment where the example embodiment is implemented using software, the software may be stored in a computer program product and loaded into computer system 200 using removable storage drive 214, hard drive 212 or communications interface 224. The control logic (software), when executed by the processor 204, causes the processor 204 to perform functions to the example embodiment as described herein.

In another embodiment, the example embodiment is implemented primarily in hardware using for example, hardware components such as Application Specific Integrated Circuits (ASICs). Implementation of the hardware state machine to perform the functions described herein will be apparent to persons skilled in the relevant art(s).

In yet another embodiment, the example embodiment is implemented using a combination of both hardware and software.

In an example software embodiment of the example embodiment, the methods described above were implemented in SPSS control language, but could be implemented in other programs such as, but not limited to, C++ programming language or other programs available to those skilled in the art.

Figure 37:
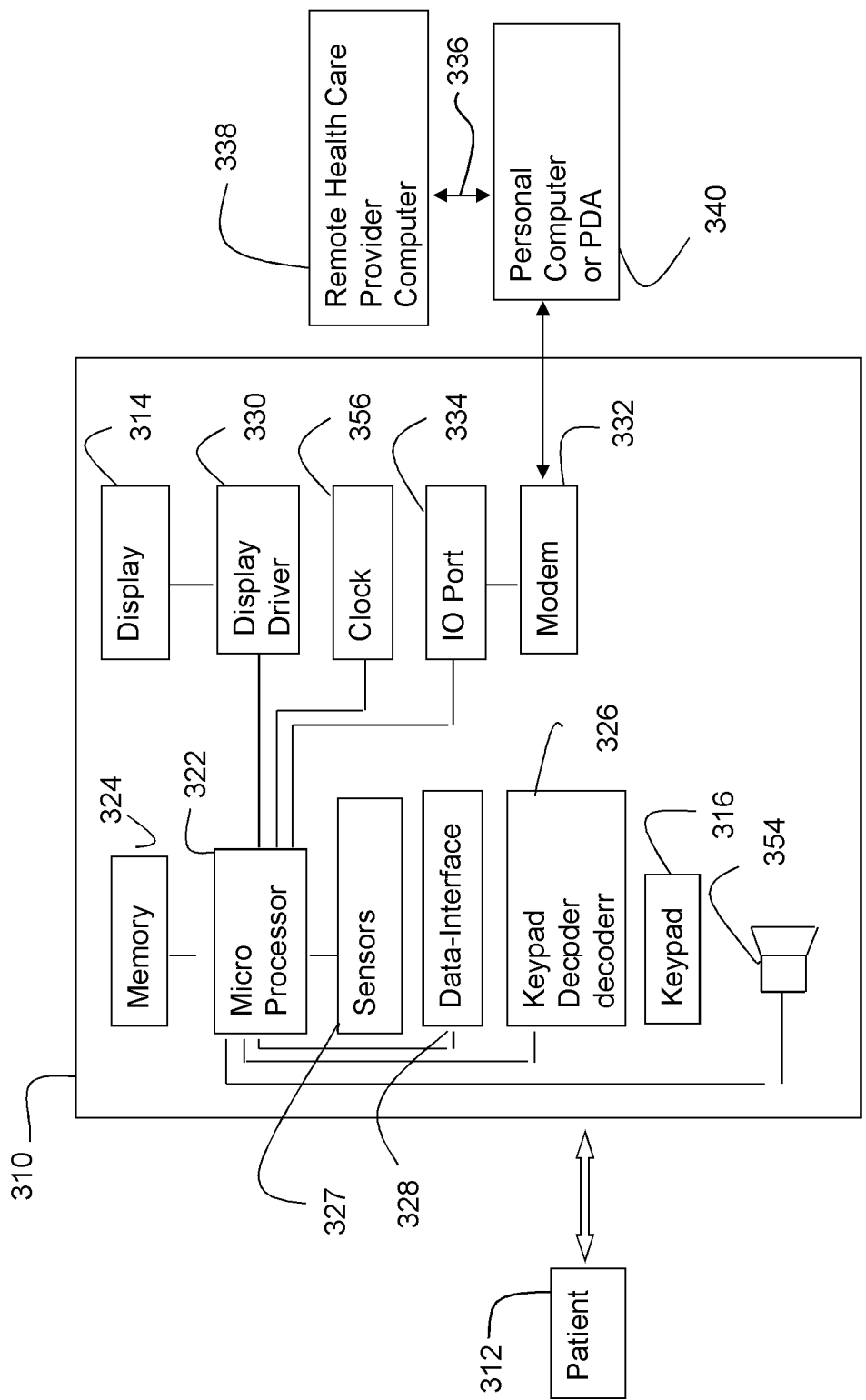
FIG. 37 is a functional block diagram for an alternative computer system implementation of the present example embodiment.
Figure 38:
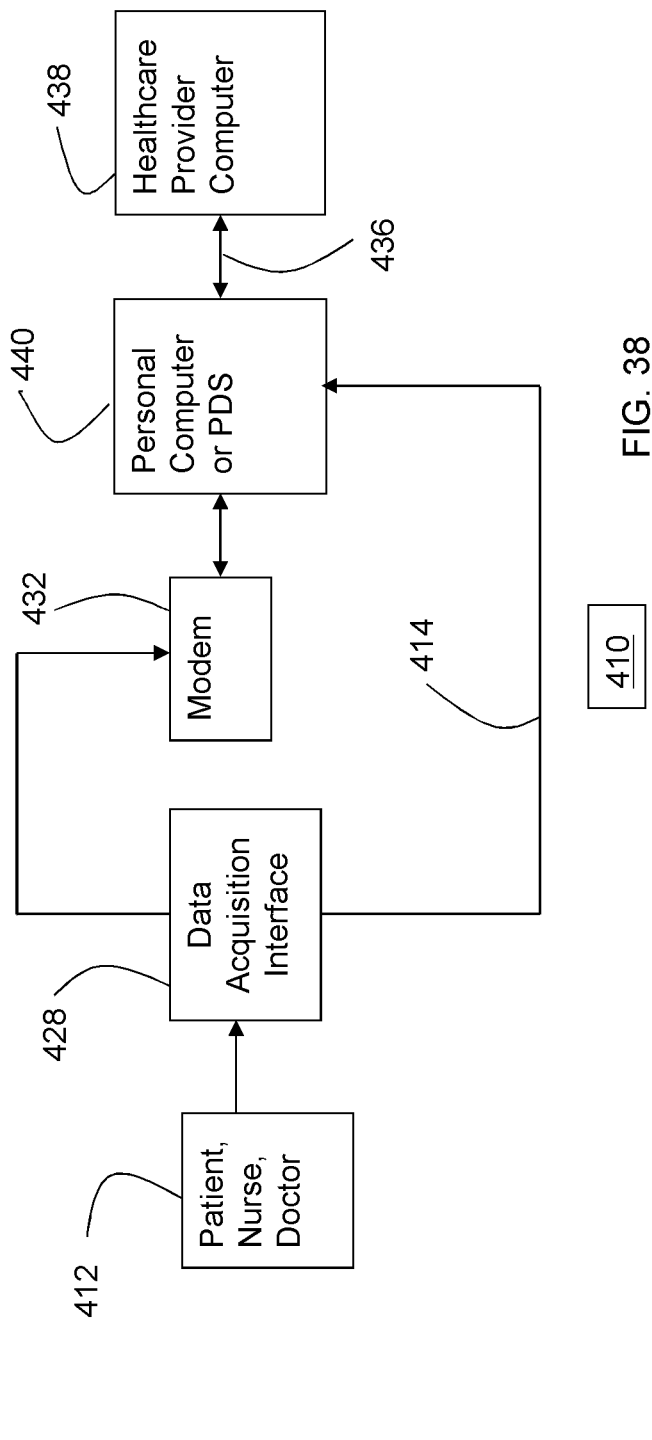
FIG. 38 is a schematic block diagram of an alternative variation of the present example embodiment related processors, communication links, and systems.
Figure 39:
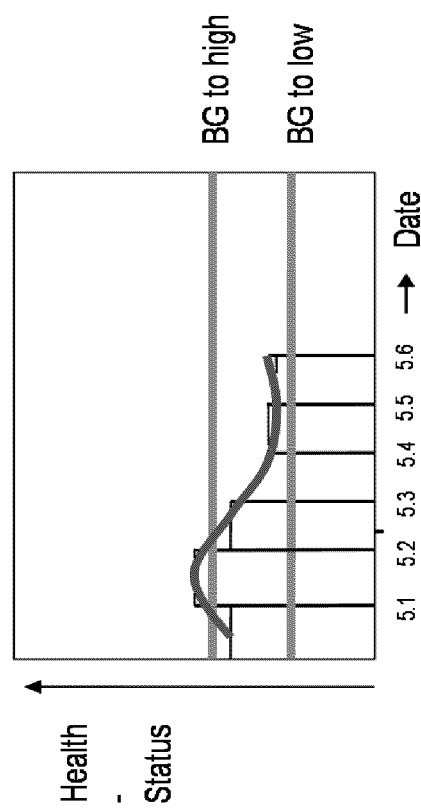
FIG. 39 is an exemplary man machine interface for a patient's record and the BG prediction over 5 days.

FIGS. 37-38 show block diagrammatic representations of alternative embodiments of the example embodiment. Referring to FIG. 38, there is shown a block diagrammatic representation of the system 410 which essentially comprises the data acquisition device 428 used by a patient or a nurse or a doctor 412 for recording, inter alia, insulin dosage readings and/or measured blood glucose ("BG"), and/or ingested carbohydrate—divided in the three classes fast, medium and slow carbohydrate—and/or psychological parameters of a self-control test. Data obtained by the data acquisition device 428 are preferably transferred through appropriate communication links 414 or data modem 432 to a processing station or chip, such as a personal computer 440, PDA, or cellular telephone, or via an appropriated internet portal. For instance, data stored may be stored within the data acquisition device 428 and may be directly downloaded into the personal computer 440 through an appropriate interface cable and then transmitted via the internet to a processing location. An example is the "ONE TOUCH" monitoring system or meter by LifeScan, Inc. which includes an interface cable to download the data to a personal computer.

Further yet, the data acquisition device 428 or and involved acquisition mechanism may include indwelling catheters and subcutaneous tissue fluid sampling or other devices to intervene in patient's physiology or measure physiological parameters.

The computer PDA 440 includes the software and hardware necessary to process, analyze and interpret the self-recorded diabetes patient data in accordance with predefined flow sequences (as describe above in detail) and generate an appropriate data interpretation output. Preferably, the results of the data by the computer 440 are displayed in the form of a paper report generated through a printer associated with the personal computer 440. Alternatively, the results of the data interpretation procedure may be directly displayed on a video display unit associated with computer 440.

FIG. 37 shows a block diagrammatic representation of an alternative embodiment having a diabetes management system that is a patient-operated apparatus 310 having a housing preferably sufficiently compact to enable apparatus 310 to be hand-held and carried by a patient. A strip guide for receiving a blood glucose test strip (not shown) is located on a surface of housing 316. The test strip is for receiving a blood sample from patient 312. Alternatively, a data-interface 328 or a sensor-interface 327 can be used, depending on which equipment of the data acquisition is in use. The apparatus includes a microprocessor 322 and a memory 324 connected to microprocessor 322. Microprocessor 322 is designed to execute a computer program stored in memory 324 to perform the various calculations and control functions as discussed in great details above. A keypad 316 is connected to microprocessor 322 through a standard keypad decoder 326. Display 314 is connected to microprocessor 322 through a display driver 330. Microprocessor 322 communicates with display driver 330 via an interface, and display driver 330 updates and refreshes display 314 and the control of microprocessor 322. Speaker 354 operates under the control of microprocessor 322 to emit audible tones alerting the patient to possible future hypoglycemia or hyperglycemia or gives word of advice what to do next to prevent hypoglycemia or hyperglycemia. Clock 356 supplies the current date and time to microprocessor 322.

Memory 324 also stores the locked data of the patient 312, the insulin dose values, the insulin types, and the parameter values used by microprocessor 822 and the neural net structures to calculate future blood glucose values, supplemental insulin doses, and carbohydrate supplements. Each blood glucose value and insulin dose value is stored in memory 324 with a corresponding date and time. Also, the neural net structures and the potential adapted neural net structures, the old and potential modified data of the self-test and the optimization parameters are stored in memory 324 with a corresponding date and time. Memory 324 is preferably a non-volatile memory, such as an electrically erasable read only memory (EEPROM). This kind of memory is preferably also in use for the alternative embodiments discussed before.

Apparatus 310 further includes an input/output port 334, preferable a serial port, which is connected to microprocessor 322. Port 334 is connected to a modem 332 by an interface, preferably a standard R232 interface. Modem 332 is for establishing a communication link between apparatus 310 and a personal computer 340 or a healthcare provider computer 338 through a communication network 336. Specific techniques for connecting electronic devices through connection cords are well known in the art. Another alternative example is "Bluetooth" technology communication.

Accordingly, the embodiments described herein are capable of being implemented over data communication networks such as the internet, making evaluations, estimations, and information accessible to any processor or computer at any remote location, as depicted in FIGS. 36-38 and/or U.S. Pat. No. 5,851,186 to Wood, which is hereby incorporated by reference herein. Alternatively, patients located at remote locations, may have their data transmitted to a central healthcare provider or residence, or a different remote location.

In particular, the present example embodiment provides a method for the predictive control of a biological organism using self-adaptive model structures, wherein the state quantities that describe an organism, i.e., the physiological and medical data that are ultimately measured and four psychological behavior style components—which are categorized based on a specified matrix structure of the organism according to the criteria (D-I-S-C/I-D-E-A) and are summarized in 16 subcategories—are ascertained and supplied to a suitable device that categorizes them so that, based on this categorization, handling instructions for the physician and patient are derived, which results in an improved "prediction of the bolus values and insulin requirements of patients with diabetes".

In particular, the present example embodiment provides a method for the predictive control of a biological organism using self-adaptive model structures, wherein, based on the results of the handling instructions described in the previous paragraph, requirements for improved therapy provided by diabetes physicians to patients with diabetes may be derived using a suitable device by incorporating the psychological data and typology definition (DISC/IDEA) and, as a further measure, incorporating the patient's compliance over time by determining a patient's requirements for future therapy based on therapy already completed and the state quantities that were measured and that describe the organism using an adaptable expert system or an additional, model-based system of categorization.

In particular, the present example embodiment provides a method for the predictive control of a biological organism using self-adaptive model structures, wherein the following method steps are carried out using a sensor device that repeatedly ascertains the DISC/IDEA data and supplies them to an electronic device, which combines them to form a vector using a program-controlled, digital device:

(1) Supply the sensor data vector to a computer-aided, statistical estimator structure, i.e., a neural network, the program of which is designed such that (1.1) its elements (neurons) are ordered such that they form a topologically closed, two-dimensional surface (a torus) on a regular or irregular grid, (1.2) all elements of the estimator estimate the structure of the one sensor data vector (SV) with a value between zero and one, these estimates being carried out—while retaining similarities between various sensor data vectors—such that, using a mathematical formula stored in the processor, these similarities are reflected in similar estimates and such that they are topologically adjacent, while retaining topological interrelationships, (1.3) in a selectable operating state, "conditioning", the behavior of all estimators and/or the parameters that characterize them are adjusted automatically via the input of unknown (not yet presented) sensor data vectors—provided they differ to a certain extent, to be defined a priori, from all sensor data vectors presented up to that point—, the adjustment representing a refinement of the ability of the estimator to categorize and, therefore, representing a refinement of the model structure of the system to be controlled, without increasing the number of estimators, (1.4) in a selectable operating state, "classification", any sensor data vectors of the sensor data vectors presented previously and stored in the structure of the estimator are assigned to the measure described above, based on similarity, so that model structures of the system to be controlled are represented by the totality of all estimator values.

(2) The totality of all values of the estimator are supplied to a second computer-aided, statistical estimator structure, which is designed such that it calculates adequate regulating parameters for the system to be regulated from the totality of all values of the first estimator, in which case:

(2.1) its elements (neurons) are ordered such that they correspond to a neural feed-forward structure, (2.2) in a selectable operating state, "conditioning", the structure of the second estimator may be designed such that a defined totality of all values of the first estimator corresponds to a certain control instruction for the system to be controlled, (2.3) in a selectable operating state, "classification", any totalities of all values of the first estimator are assigned to certain control instructions.

In particular, the present example embodiment provides a system using a prediction system of physiological data for establishing a target function for an optimization algorithm which is implemented in a computer system. With this optimization algorithm, optimal decisions for individual use or medical advice can be computed.

Preferably, in the above method or system, a target function, Equation 6

$$t = \sqrt{\frac{\int (G - G_t)^2}{T}}$$ Equation 6 is used, where G is the ideal glucose value, Gt is the glucose value at time t and T is the measurement period.

Preferably, in the above method or system, cross validation methods are used for reducing necessary patient records.

Preferably, in the above method or system, the prediction correctness (failure measure) of the predictor is appraised with a function as, Equation 7:

$$t = \sqrt{\frac{\int (G - G_t)^2}{T}}$$ Equation 7 where G is the ideal glucose value, Gt is the glucose value at time t and T is the measurement period.

Preferably, in the above method or system, missing values for patient records in a cross validation or learning process are substituted by values delivered by a predictor as described (failure measure with predictor values).

Preferably, in the above method or system, a patient's record is classified into risk classes which are comprised of parameters describing the glucose value and the controllability of the patient's behavior.

Preferably, in the above method or system, the prediction correctness for the glucose value for a patient as a parameter describing the risk classes is used.

Most preferably, in the above method or system, a patient is given a feedback with described risk classes.

Preferably, in the above method or system, input data are delivered by a continuous sensor system, i.e. a connection with sensor data is provided.

Preferably, in the above method or system, cross validation and scoring methods for selecting of optimal parameters are used.

Preferably, in the above method or system, cross validation for categorizing patient cohorts by a physiological description is used, i.e. cross validation for assessing DISC/IDEA clusters is used.

Preferably, in the above method or system, based on a detected surplus of insulin at any given time, a prediction is made which indicates that a certain amount of additional carbohydrates may be ingested.

Preferably, in the above method or system, a patient DISC/IDEA class is used as an input value for the prediction system, i.e. DISC/IDEA categories serve as an input for the prediction.

Preferably, in the above method or system, patient records for a learning procedure are separated in DISC/IDEA categories, i.e. a stratification with DISC/IDEA categories is carried out.

In summary, the example embodiment proposes a data analysis computerized (or non-computerized) method and system and a patient specific estimations structure method and system for the simultaneous evaluation of significant components of glycemic control in individuals with diabetes: BG and the risk of hyperglycemia and hypoglycemia combined with a predictor for the early and further future BG-courses, the personal medical records and advice for an optimal therapy. The method provides, among other things, four sets of output.

The potential implementations of the method, system, and computer program product of the example embodiment are that it provides the following advantages, but are not limited thereto. First, the example embodiment enhances existing home BG monitoring devices by producing and displaying: 1) estimated categories for BG, 2) estimated probability for SH in the subsequent six month, 3) estimated short-term risk of hyperglycemia and hypoglycemia (i.e. for the next 24 hours), 4) estimated doses of insulin requirements to fix the BG in a favored interval. The latter may include warnings, such as an alarm, that indicates imminent hyperglycemia and hypoglycemia episodes. These four components can also be integrated to provide continuous information about the glycemic control of individuals with diabetes, and to enhance the monitoring of their risk of hyperglycemia and hypoglycemia.

As an additional advantage, the intention enhances existing software or hardware that retrieves measured BG data.

Moreover, another advantage, the example embodiment evaluates the effectiveness of various treatments for diabetes and changes of the medical report caused by the lifestyle of the patient.

Further still, as patients with diabetes face a life-long optimization problem of maintaining strict glycemic control without increasing their risk of hyperglycemia and hypoglycemia, the present example embodiment alleviates this related problem by use of its individual patient model, which "learns" over time the special psychological and physiological behavior of the patient and adapts 1) the succession of the necessary insulin doses to fix an optimal BC, 2) the advice what to do next to prevent hyperglycemia and hypoglycemia, 3) the standards for optimizing the therapy of the patient.

Another advantage, the example embodiment evaluates the effectiveness of new insulin or insulin delivery devices. Any manufacturer or researcher of insulin or insulin delivery devices can utilize the embodiments of the example embodiment to test the relative success of proposed or tested insulin types or device delivery designs.

Finally, another advantage, the example embodiment evaluates the effectiveness of drugs that are adjunct to insulin therapy.

Example

This example consists of seven algorithms for simultaneous evaluation, from routine collected physiological data blood glucose, ingested carbohydrate—divided in the three classes fast, medium and slow carbohydrate—and psychological parameters of the self-control test DISC/IDEA to prevent hyperglycemia and hypoglycemia, to calculate the BG value in the early next future (24 hours), to give indications about how to optimized the daily behavior of the patient in the context of an evidence-based medicine, to optimize the therapy, and to verify the daily behavior of selected groups to optimize the DISC/IDEA categorization. This method pertains directly to enhancement of existing BG monitoring devices, an existing DISC/IDEA categorization, the mathematical procedure of cross-correlation, a standard to divide the three classes: fast, medium and slow carbohydrates and the knowledge about periods of an increasing risk for hyperglycemia and hypoglycemia. The basis of this method is an individual computer-based model of a diabetes patient. The data analysis method has seven components (algorithms) all advecting in the patient's computer model.

Algorithms (see FIG. 35)
Algorithm 1: Creation of an individual patient's model
Algorithm 2: Calculation/prediction of the BG in given time interval
Algorithm 3: Evaluation of long-term risk for severe hyperglycemia and Hypoglycemia
Algorithm 4: Evaluation of short-term (within 24-48 hours) risk of hyperglycemia and hypoglycemia
Algorithm 5: Calculation of necessary insulin doses to fix the patient's BG in a favorite interval
Algorithm 6: Verification of behavior of the selected groups to optimize the DISC/IDEA categorization
Algorithm 7: Verification of therapy and predictor to optimize both Algorithms 1, 2, 3 and 5 provide uninterrupted monitoring and information about the overall glycemic control of an individual—with type 1 or type 2 diabetes mellitus (T1 DM, T2DM), covering both the high and low ends of the BG scale.

Algorithm 4 is supposed to be activated when Algorithm 3 indicates an increasing long-term risk for hyperglycemia or hypoglycemia. Upon activation, Algorithm 4 requires more frequent monitoring (4 times a day) and provides a 24 to 48-hour forecast of the risk for moderate/severe hyperglycemia and hypoglycemia.

Data Sets

In order to ensure that the results of our optimization can be generalized to population level, Algorithms 1, 2, 3 and 4 were first optimized using training data sets and tested for accuracy using unrelated test data sets.

For Algorithm 5, standard values for the administration of insulin doses were used that were verified by Algorithms 2, 3 and 4.

For Algorithm 6, three special studies (Annex $IS_1$, $IS_2$, $IS_3$) have been carried out:

(1) $IS_1$: The "Proof of Concept Study" with n=131 diabetes patients of type 2 and type 1 in February-March-April 2009 verified that 100% of the patients accepted the resulting "Individual Personal Profile" with the personal style (English version "I-D-E-A", German version "A-D-E-L"=Analytic (Analytiker)-"Driver"-Expressive(r)-Amiable/ "Liebenswerter") as "correct and realistic description" of their personal style (Annex $IS_1$).

(2) $IS_2$: In a second study with n=1,000 patients, a multiple regression analysis and a factor analytic study led to the categorization of the patients and was verified by an analysis of the "Secondary Factors" which indicate the "3 Categories" of patients ("E & E"=Enabling and Empowerment, "C & C"=Communication and Control, "A & C"=Adaptation (of Lifestyle) and Coping). The "9 Success Factors of Diabetes Management" have been identified (which was later on a "10 Factor Scheme", since the two component factor 3 of the $IS_2$-Study "Motivation and Knowledge of Diabetes Management" was later on differentiated in the German Study $IS_3$ into two separate factors: F3="Motivation (and Energy)" and F4="Knowledge of Self-Care".

(3) $IS_3$: The results of the n=1,000 US Study ($IS_2$) were verified and reinforced by the third study $IS_3$ (InDiMa™ Study 3), carried out in November (Pre Studies) and December (Final Contract Study) 2010:

relevance of style for behavior, adaptation and communication (multiple correlation R=0.45);
verification of 9 (10) success factors;
classification of patients in three categories ("E & E", "C & C", "A & C").

Training Data Set 1:
15 data sets representing standard patients which eat fast carbohydrate and inject a large dose of insulin (sub-cutaneously) and describing the BG-behavior of the patient's metabolism over a 24 h period.

Training Data Set 1:

15 data sets representing standard patients which eat medium carbohydrate and inject a large dose of insulin (sub-cutaneously) and describing the BG-behavior of the patient's metabolism over a 24 h period.

Training Data Set 1:

15 data sets representing standard patients which eat slow carbohydrate and inject a large dose of insulin (sub-cutaneously) and describing the BG-behavior of the patient's metabolism over a 24 h period.

Training Data Set 1:

15 data sets representing standard patients which eat fast carbohydrate and inject a medium dose of insulin (sub-cutaneously) and describing the BG-behavior of the patient's metabolism over a 24 h period.

Training Data Set 1:

15 data sets representing standard patients which eat medium carbohydrate and inject a medium dose of insulin (sub-cutaneously) and describing the BG-behavior of the patient's metabolism over a 24 h period.

Training Data Set 1:

15 data sets representing standard patients which eat slow carbohydrate and inject a medium dose of insulin (sub-cutaneously) and describing the BG-behavior of the patient's metabolism over a 24 h period.

Training Data Set 1:

15 data sets representing standard patients which eat fast carbohydrate and inject a small dose of insulin (sub-cutaneously) and describing the BG-behavior of the patient's metabolism over a 24 h period.

Training Data Set 1:

15 data sets representing standard patients which eat medium carbohydrate and inject a small dose of insulin (sub-cutaneously) and describing the BG-behavior of the patient's metabolism over a 24 h period.

Training Data Set 1:

15 data sets representing standard patients which eat slow carbohydrate and inject a small dose of insulin (sub-cutaneously) and describing the BG-behavior of the patient's metabolism over a 24 h period.

Algorithm 1: Creation of an Individual Patient's Model

Example No. 1 provides for, without being limited thereto, a mathematical model, representing a patient, with varying eating and injecting behavior.

Algorithm 1 includes a neural net following the self-organizing-principle for sorting diverse personal status vectors (PSVs) to representing activity patterns on a closed grid. An exemplary structure of these kinds of nets is shown in FIG. 40 and an exemplary closed grid in FIG. 42.

In Algorithm 1, the first layer is constituted of 12 estimators, i.e, the 10 Core Instruments [see Annex ICS "InDiMa™ Communication System" with 10 Core Instruments (especially Core No. 1=Individual Diabetes Status and Core No.

2=IPP="Individual Personal Profile",

Core No. 11="Individual Stress Test" (IST), and

Core No. 12="Individual Measurement Behavior" (IMB)].

These estimators are comprised to 10 Success Factors and 3 Patient Categories. They are representing some (for example, but not limited to) 267 items of the "InDiMa™ Communication System"=ICS.

The second layer, which represents the neuro-mental patient's model itself, is constituted of 12 times 12 neurons/estimators. To create the patient's model, we proceed as follows.

The initial learning rate $\varepsilon^t$ was set to 0.9, the initial adoption function $\delta^t$ to 0.98. For the neighborhood function $h_{si}{}^t$ the Gaussian function was selected. The initial radius of the influence of $h_{si}{}^t$ was the grid radius.

A total of 10 data sets of every patient's type were presented in random order to the neural net structure. The weights were adapted in 1,100 conditioning operation state steps.

Detailed estimations of the validity of the neural net were made using the test data sets only.

Figure 45:
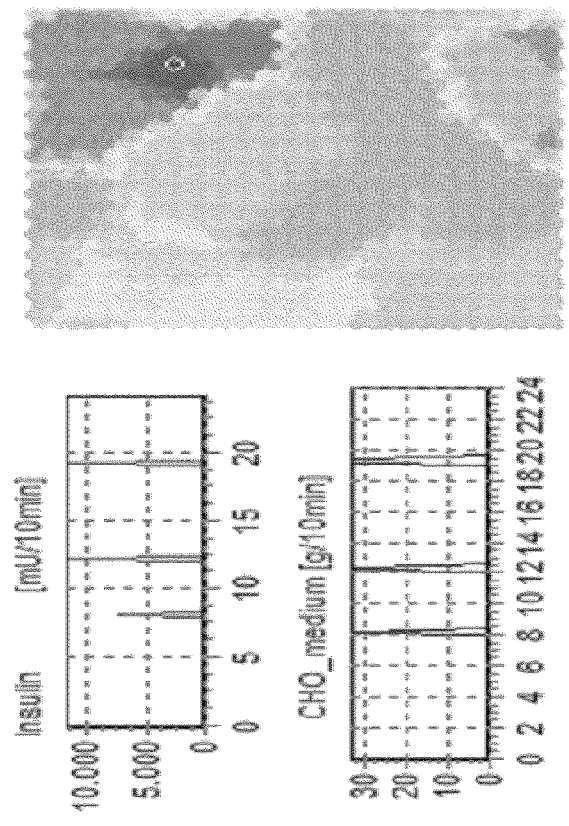
FIG. 45 is an exemplary modeled patient's physiological time behavior coded in an activity pattern in dependence of given insulin doses and ingested carbohydrates.

This separation of training and test data sets allows us to claim that the estimated preciseness of Algorithm 1 be generalized to any other data of subjects following the physical and psychical standard of the used patient category. Moreover, when we present test PSV-sets which slightly differ from the learning PSV-sets we can observe, that the activity pattern also differed only slightly, with a significance of 0.98 calculated with a standard t-test. An exemplary visualization of a PSV and the corresponding activity pattern of the neural net are shown in FIG. 45.

Algorithm 2: Calculation/Prediction of the BG in Given Time Interval

Example No. 1 provides for, without being limited thereto, an expansion of Algorithm 2 to include estimating individual probabilities for the blood glucose (BG) in a defined time in the future, which in this example, without loss of generality, was limited to a maximum to 24 hours.

Algorithm 2 includes a neural net resp. a hierarchical neural net battery, whereby all of them follow the self-organizing-principle for sorting diverse personal status vectors (PSV's) to representing activity patterns on a closed grid and a neural net integrating the estimations of the SOM's, to an overall patient behavior model, followed by a neural net, following the backpropagation algorithm to decode the activity pattern of the lower neural net hierarchy. In that way, a predicted BG-value is calculated for a defined time window.

Example (FIG. 41): An exemplary structure of these kinds of nets is shown in FIG. 41. In Algorithm 2, the first layer is constituted of 2,320 estimators.

The "number" and "power" of these estimators is extracted and "condensed" from the complete patient information of the BPPS model, for instance (but not limited hereto) 232 items of 10 Core Instruments of the InDiMa™ Communication System (but not limited to this exemplary model) with 10 Success Factors for Diabetes Management (Annex: Study $IS_2$, USA, n=1,000; $IS_3$, Germany, n=2,358).

These 2,320 neurons/estimators (defined by the BPPS model information of 232 items, 10 Core Instruments, 10 Success Factors and 3 Secondary Factors or "Patient Categories") represent the features of a patient's neuronal category/status at a given time T.

If a time scale, for example 10 minutes, is chosen and a prediction level of 4 h is selected, 24 PSV's, representing 4 hours of "history".

The second layer, which represents the neuro-mental patient's model itself, is constituted of 12 times 12 neurons/estimators. To create the patient's model, we proceed as follows.

The initial learning rate $\varepsilon^t$ was set to 0.9, the initial adoption function $h_{si}{}^t$ to 0.98. For the neighborhood function $h_{si}{}^t$ the Gaussian function was selected. The initial radius of the influence of $h_{si}{}^t$ was the grid radius.

A total of 10 data sets of every patient's history were presented in random order to the neural net structure. The weights were adapted in 1,100 conditioning operation state steps.

Detailed estimations of the validity of the neural net were made using the test data sets only.

This separation of training and test data sets allows us to claim that the estimated preciseness of Algorithm 2 be generalized to any other data of subjects following the physical and psychical standard of the used patient category. Moreover, when we present test PSV-sets which slightly differ from the learning PSV-sets, we can observe that the activity pattern also differed only slightly, with a significance of 0.96 calculated with a standard t-test.

To calculate the predictive regime of the BG we proceed further on as follows:

The activity pattern of the neural net hierarchy 1 was presented to the integration SOM of hierarchy 2 and its resulting activity pattern to the input layer of the backpropagation neural net (neural net 2), whereby the input layer of the backpropagation neural network structure has 144 neurons/estimators, the hidden layer 30, while the number of estimators in the output layer can be chosen freely and can be as many estimators as required. The initial learning rate $\varepsilon^t$ was set to 0.75.

A total of 10 data sets of every patient's history were presented in random order to the neural net 2. The weights were adapted in 2,000 conditioning operation state steps until the desired BG-value regime was decoded out of the activity pattern of the neural net 1.

Detailed estimations of the validity of the neural net were made using the desired BG-values data sets and comparing them with the BG data regimes the net-structure calculates.

Also, detailed estimations of the validity of the neural net were made using the test data sets only.

Figure 46:
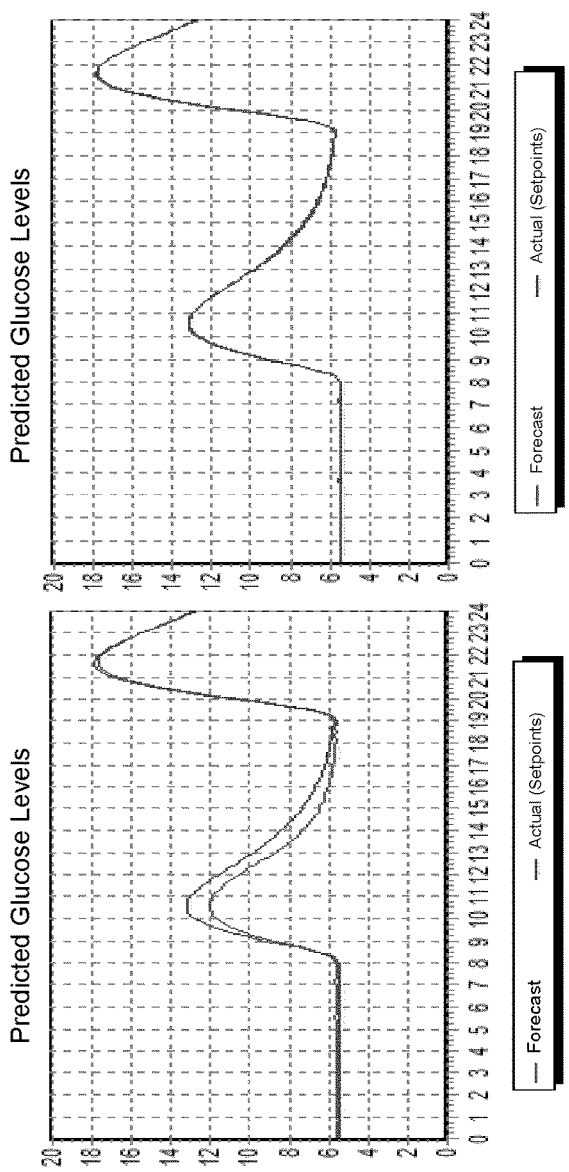
FIG. 46 is an example of predicted BG records; left-hand side: not well adapted, right-hand side: well adapted.

The separation of training and test data sets allows us to claim that the estimated preciseness of Algorithm 1 be generalized to any other data of subjects following the physical and psychical standard of the used patient category. Moreover, when we present test PSV-sets which slightly differ from the learning PSV-sets, we can observe that the activity pattern also differed only slightly, with a significance of 0.97 calculated with a standard t-test. An exemplary visualization of a not yet well predicted BG-regime (left-hand side) and a well predicted BG-regime (right-hand side) are shown in FIG. 46.

Algorithm 3: Evaluation of Long-Term Prediction of the Patient's Status

Example No. 1 provides for, without being limited thereto, an expansion of Algorithm 2 to include estimating individual probabilities for biochemically significant hypoglycemia (BSH, defined as BG reading<=39 mg/dl) or biochemically moderate hypoglycemia (BMH, defines as 39 mg/dl<BG reading<=55 mg/dl) or the development of the patient's status in the future.

Algorithm 3 is a classification algorithm. That is, based on SMBG data for a subject, it classifies the subject in a certain risk category for future BSH or MSH. In order to approximate as closely as possible future real applications of Algorithm 3, we proceed as follows:

From the individual patient's model and from the calculation/prediction of the BG in a given time interval and from the DISC/IDEA-categorization, an enlarged PSV data set is created.

As described above, a neural predictor is created to calculate the probability for biochemically significant hypoglycemia or biochemically moderate hypoglycemia, and advice is given when these events occur to a significant degree. Also, it is created to calculate the probability for patient's psychological behavior in time.

Detailed estimations of the validity of the neural net were made using the desired BG-values data sets and comparing them with the BG data regimes the net-structure calculates.

Also, detailed estimations of the validity of the neural net were made using the test data sets only.

The separation of training and test data sets allows us to claim that the estimated preciseness of Algorithm 1 be generalized to any other data of subjects following the physical and psychical standard of the used patient category. Moreover, when we present test PSV-sets which slightly differ from the learning PSV-sets, we can observe that the activity pattern also differed only slightly, with a significance of 0.93 calculated with a standard t-test.

Algorithm 4: Evaluation of Short-Term Risk for Severe Hyperglycemia and Hypoglycemia Example No. 1 provides for, without being limited thereto, an expansion of Algorithm 3 to include estimating individual probabilities for biochemically significant hypoglycemia (BSH, defined as BG reading<=39 mg/dl) or biochemically moderate hypoglycemia (BMH, defines as 39 mg/dl<BG reading<=55 mg/dl) and/or patients psychological behavior in a short time.

Algorithm 4 is a classification algorithm following the same principles as the algorithm for the long-term risk, described above. In order to approximate as closely as possible future real applications of Algorithm 4, we proceed as follows:

From the individual patient's model and from the calculation/prediction of the BG in given time interval and from the DISC/IDEA-categorization an enlarged PSV-data set is created.

As described above, a neural predictor is created to calculate the probability for biochemically significant hypoglycemia or biochemically moderate hypoglycemia, and advice is given when these events occur to a significant degree in the early next (immediate) future.

Detailed estimations of the validity of the neural net were made using the desired BG-values data sets and comparing them with the BG data regimes the net-structure calculates.

Also, detailed estimations of the validity of the neural net were made using the test data sets only.

The separation of training and test data sets allows us to claim that the estimated preciseness of Algorithm 1 be generalized to any other data of subjects following the physical and psychical standard of the used patient category. Moreover, when we present test PSV-sets which slightly differ from the learning PSV-sets, we can observe that the activity pattern also differed only slightly, with a significance of 0.945 calculated with a standard t-test.

Algorithm 5: Calculation of Necessary Insulin Doses to Fix the Patient's BG in a Favorite Interval Example No. 1 provides for, without being limited thereto, an expansion of Algorithm 4 to include calculating the individual dose for an insulin injection to fix the patient's BG in a favorite interval.

Algorithm 5 is a Calculating Module. In Order to Approximate as Closely as Possible Future Real Applications of Algorithm 5, we Proceed as Follows:

From the individual patient's model and from the calculation/prediction of the BG in given time interval and from the DISC/IDEA-categorization and from the patient's physical data like weight, drug abuses, sports activities, sex etc., an insulin dose is calculated to fix the BG in the given time window in a favorite interval.

This dose is given as input component to the individual patient's model which calculates by means of the representation of the patient's physiology the BG values in the early next future, preferably in the next 3 hours, by the help of the prediction algorithm described above.

Algorithm 6: Verification of Behavior of the Selected Groups to Optimize the DISC/IDEA-Categorization Example No. 1 provides for, without being limited thereto, an expansion of Algorithm 2 to include estimating individual probabilities for an optimal patient's model by changing the DISC/IDEA-parameters.

Algorithm 6 is a calculating module based on statistical formula methods. In order to approximate as closely as possible future real applications of Algorithm 6, we proceed as follows:

From the individual patient's model and from the calculation/prediction of the BG in a given time interval and from the DISC/IDEA-categorization and from the patient's physical data like weight, drug abuses, sports activities, sex etc., an individual adaptation of the DISC/IDEA-categories are calculated.

Algorithm 7: Verification of Therapy and Predictor to Optimize Both

Example No. 1 provides for, without being limited thereto, an expansion of Algorithm 2 to include estimating individual probabilities for an optimal patient's model by changing the DISC/IDEA-parameters.

Algorithm 7 is a calculating module based on statistical formula methods. In order to approximate as closely as possible future real applications of Algorithm 7, we proceed as follows:

An optimization module with a target function, Equation 8

$$t = \sqrt{\frac{\int (BG - BG_t)^2}{T}} \quad \text{Equation 8}$$

whereby BG describes the ideal glucose value, $BG_t$ the glucose value at time t and T the measurement period, is implemented to calculate the optimal glucose concentration for individual use or medical advice.

Using cross validation methods, it is calculated if the necessary patient records can be reduced.

The prediction correctness of the predictor is appraised by implementing the function, Equation 9:

$$t = \sqrt{\frac{\int (G - G_t)^2}{T}} \quad \text{Equation 9}$$

whereby BG describes the ideal glucose value, $BG_t$ the glucose value at time t and T the measurement period.

Missing values for patient records in a cross validation or learning process are substituted by values delivered by the predictor as described above.

Patient's records are classified into risk classes. These risk classes are comprised of parameters describing the glucose value and the controllability of the patient's behavior.

The prediction correctness for the glucose value for a patient is used as a parameter describing the risk classes.

These risk classes are returned to the patient as a feedback.

The example embodiment may be embodied in other specific forms without departing form the spirit or essential characteristics thereof. The foregoing description of examples, embodiments, etc. is therefore to be considered in all respects illustrative rather than limiting of the example embodiment described herein. Scope of the example embodiment is thus indicated by the appended claims rather than by the forgoing description, and al changes which come within the meaning and range of equivalency of the claims are therefore intended to be embraced therein.

The system according to the example embodiment may include an "Individualized Disease Management System" ("InDiMa™ System") which operates on four integrated program modules:

1. SCTWEB Module© (Survey Construction Tool Web Module)

The SCTWEB MODULE© contains a data-base tool in which we can put validated items and descriptors into categories which forms the basis of the InDiMa™ survey.

The SCTWEB MODULE© is prepared to handle all western languages and Cyrillic languages like Ukrainian and Russian languages.

Once a survey is set-up in the SCTWEB MODULE©, this tool publishes the InDiMa™ questionnaire on the internet and is approachable for the browsers: Internet Explorer (6 and 7 and higher), Firefox (2 and 3) and Safari (3,0). This accounts for 98% of the browser market.

2. The CSM Module© (Client and Survey Management Module)

The CSM Module contains several databases in which we register the healthcare provider who will participate in the InDiMa™ survey. This can be done per region, in the USA per state and in Europe per country.

At that moment, the healthcare provider is registered into the system using an e-mail with his password sent to him. As a result, the healthcare provider is able to setup his patient database.

From that moment on the healthcare provider can create a survey out of the modules that are set in the SCTWEB Module© and send that survey to the patient.

At the moment the patient is matched to the survey that the healthcare provider created the system creates and individualized ID-number that gives a patient entrance into two internet pages. The first page is the survey page and the second page is his/her personal portfolio page.

Every patient receives an individual portfolio page on the internet on which he can see his "concept-report" and can create his/her final report also with comments/remarks her/himself to send to the healthcare provider.

Also, the CSM Module automatically creates a healthcare provider control page on which—after authorization of the patient—the healthcare provider finds the report from the patient.

The InDiMa™ system is set up in in such a way that based on real-time scoring the "concept-reports" will be published on the portfolio page of the patient, instantly after filling in the questionnaire, and that there is instant publishing of the report on the healthcare provider control page after authorization and establishment of the final report of the patient.

The system will send out automatically an announcement by e-mail to the healthcare provider that the report of the patient is available.

3. The RG Module© (Report Generator Module)

The RG Module is the survey scoring program. It is designed to build the reporting template for the report lay-out. Reports are placed on management control pages and personal portfolio pages.

4. The PC Module© (Patient Communication Module)

The PC Module is integrated in the CSM module and sets the communication templates for patients, respondents and health care providers.

Based on the content of the CSM module, the PC module notifies and instructs how to approach a survey, sends out reminders, notifies respondents, reminds respondents, notifies when reports are published etc.

5. Safeguards of the InDiMa™ System

The InDiMa™ Service Centers are linked to our data centers.

Data centers are positioned in Amsterdam (we lease several dedicated servers at Denit (our provider) with a 99.8% performance service level agreement.

The back-up systems for the dedicated servers are positioned in Norway at Denit. As an extra safeguard, there are two real time extra back-up data centers on our own servers, one in Rotterdam (WVD media) and one in Zwijndrecht (InDiMa™ Service Center).

So in case of emergency in Amsterdam, we automatically switch to the back-up systems and then we have a maximum loss of data entry of 1 hour.

All processing centers are logged in to our data centers through the internet.

For the InDiMa™ project we place extra high speed/high capacity servers in the data centers which provide capacity for a minimum of 1,000,000 data entries and storage reports a year, to guarantee real time scoring and processing (January 2011).

The system according to the example embodiment may include a Report Generator Module.

The Report Generator Module is an application that works in cooperation with the portfolio system and the "Survey Construction Tool (SCT). The Report Generator Module is used to make reports for survey trajectories and is specialized in making personalized reports for surveys.

In this document, we firstly describe the key concepts and basic flow of the program. Then we go into more detail on how to use the report generator to achieve the "Basic Individual Profile" (BIP) Reports and Promptsheets.

As mentioned before, the report generator module works together with the Portfolio System and the Survey Construction Tool.

FIG. 47 shows the way the communication is constituted. Data is downloaded to the report generator, reports are generated and those reports are finally uploaded back to the portfolio system to be available online.

Report Generator Concepts

Although some aggregate functions are available, with the report generator a report is always created for a specific patient. Reports generated using the report generator can automatically be uploaded back to the portfolio system so that it is available to both participants (via the personal portfolio page) and doctors of HCP's (through the portfolio status page).

Usually, every survey can be different from the next. Hence, the resulting reports are likely to vary in structure as well. That is why the report generator works with templates/forms, i.e. partially complete documents to be filled in and that can be reused and adapted and hence provide the demanded flexibility.

Figure 48:
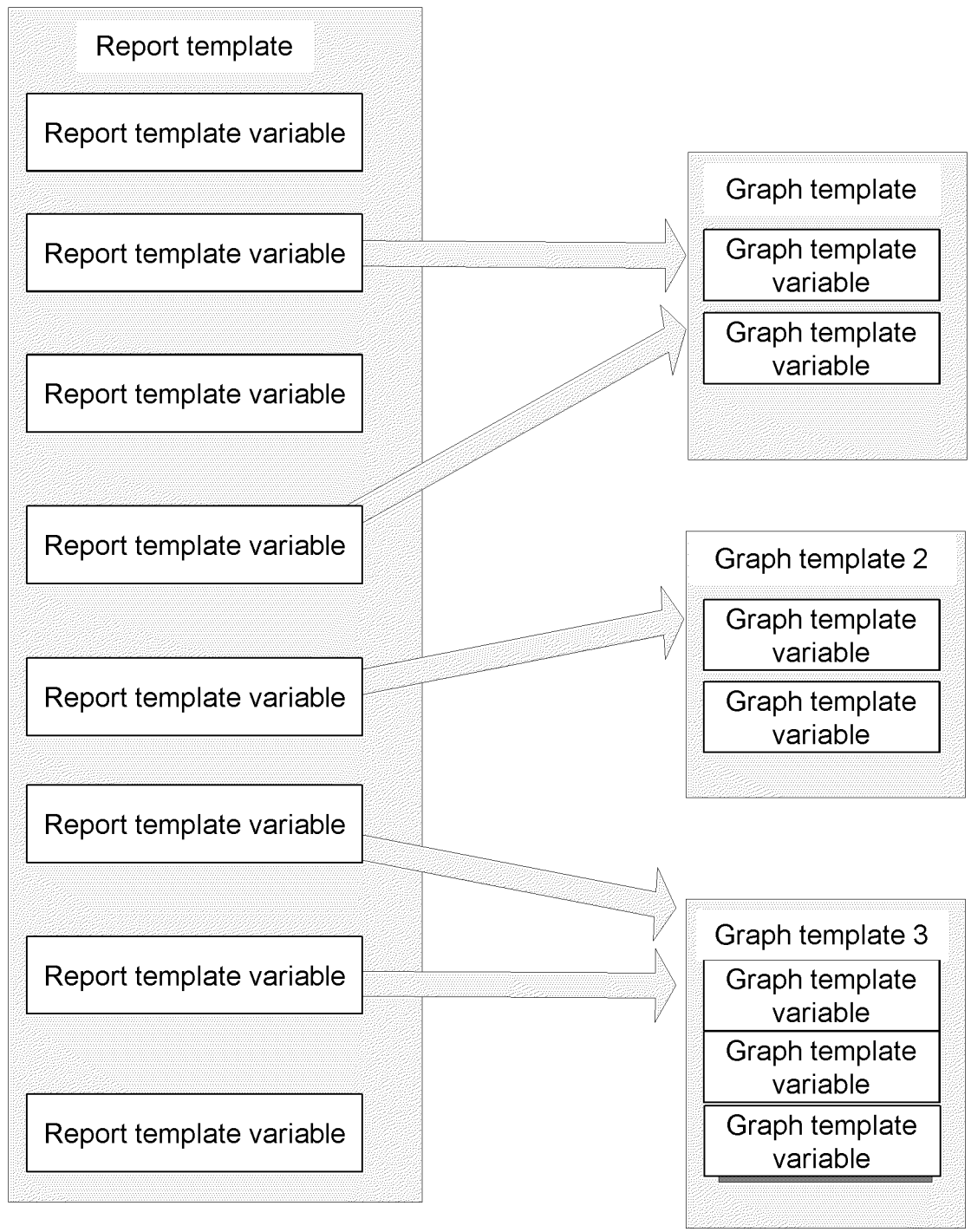
FIG. 48 is a schematic diagram showing how report templates and graph templates are related.
Figure 49:
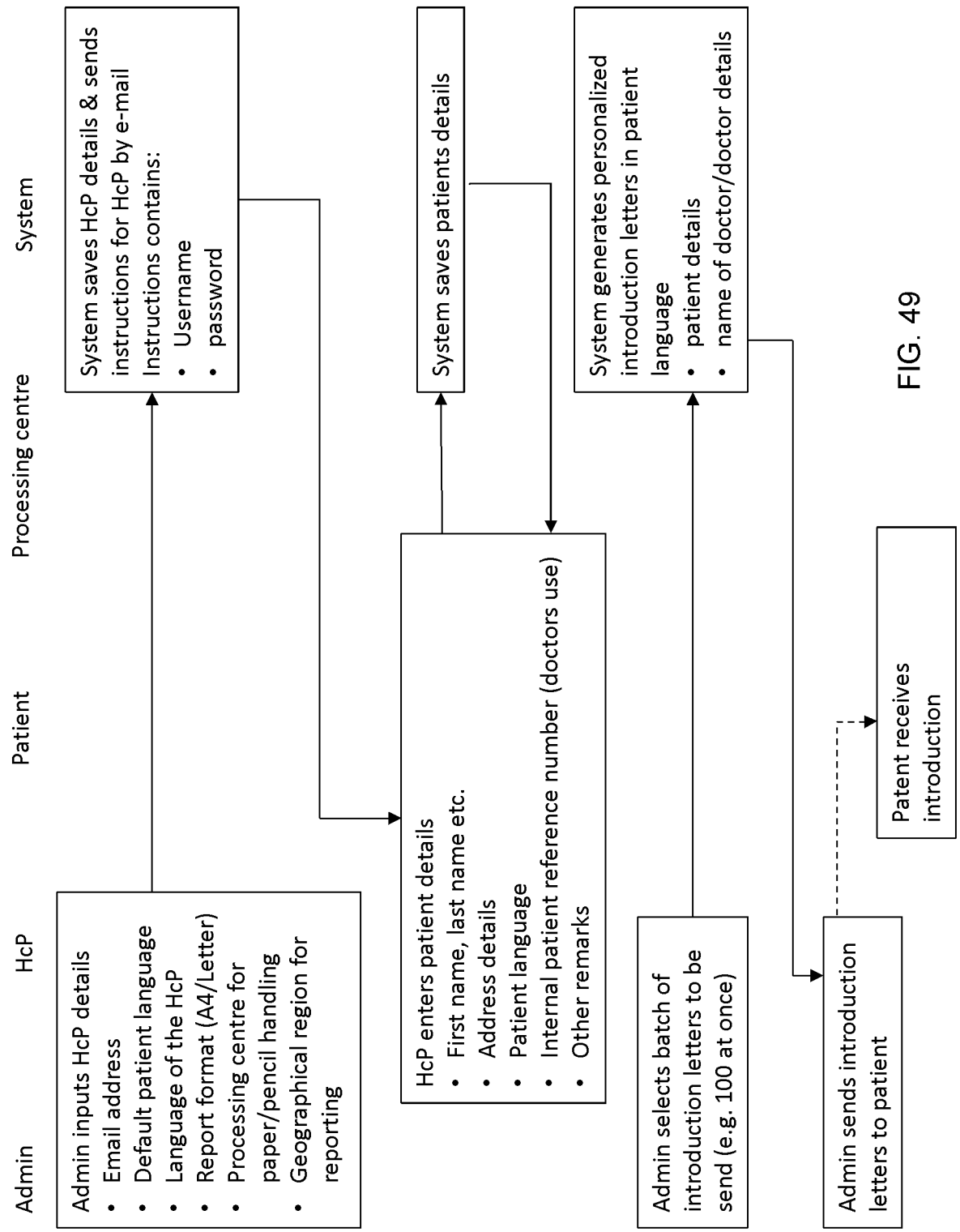
FIGS. 49-51 together constitute a flowchart describing the interaction between patients and health care professionals within the system.
Figure 50:
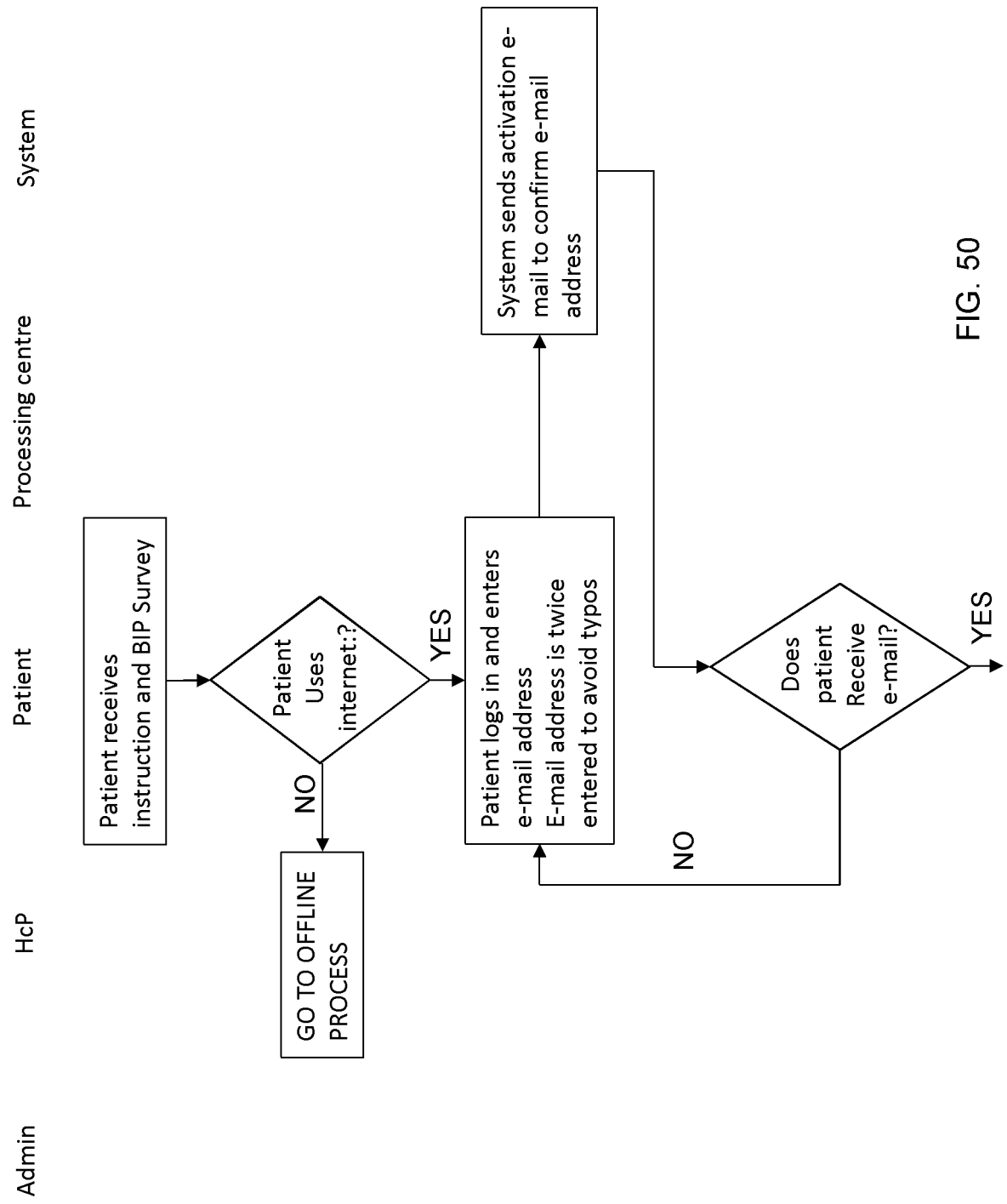
Figure 51:
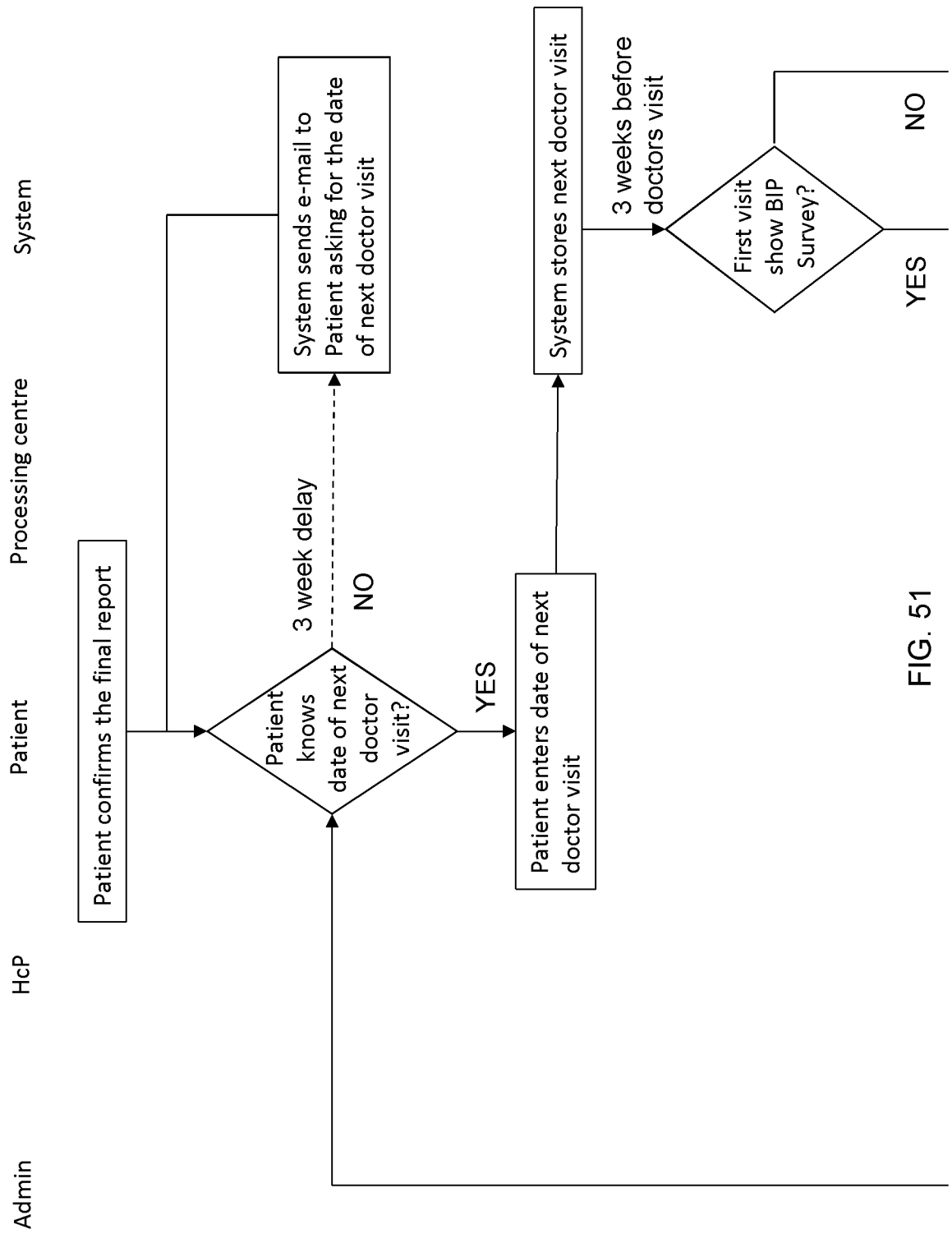

FIG. 48 is a schematic diagram showing how report templates and graph templates are related. On the basis of every report, there is a report template. A report template may be a Microsoft Word XML document and hence may be edited using the widely supported Microsoft Word XML.

A report template contains report template variables. A report template variable is a part of the report that is replaced by actual survey data once a report is generated. There are different types of report template variables. One of them is a reference to a graph template. A graph template shows information (averages, totals) about a specific survey question or a group of survey questions. A graph template is also a Microsoft Word document, but can contain embedded Excel Chart or Microsoft Chart objects. Graph template contains graph template variables. A graph template variable is replaced by a (numerical) value upon report generation.

With the report generator we can create two types of reports: individual patient reports and general reports. Individual reports are reports that are created for specific patients and doctors such as BIP profiles and prompt sheets. In those reports, data is used that is linked to a specific patient. The patients and doctors are be entered in the portfolio system under a "Client management" section. General reports are reports that use all survey data, for instance for a group of patients for one doctor. Those kinds of reports are used to report on the higher "organizational" level and not for specific patients.

Based on various settings that can be modified using the user interface, the report generator will insert one or more texts in a report.

All texts reside in separate Word XML documents that have particular, pre-set filenames. These documents all reside in a folder that should have a certain, pre-defined structure. Which texts are inserted and where, depends on the place of the variables used in the report template.

As mentioned before, the report generator also works in cooperation with the survey construction tool. Hence, it is possible to display information from the SCT.

Depending on the settings in the user interface and of course the patient's survey data, a text is inserted in the report. All individual texts are stored in separate Word documents, that reside in a predefined folder structure. There are a number of report variables, that each inserts (each of which inserts) a different text into the document.

The system and method according to the example embodiment enables clients/patients and HCP/doctors to remove typical communication barriers in existing health care systems. By providing a data communication platform within the system of the example embodiment for communicating relevant physiological (medical, biological) and psychological (personality profile determined using psychometry) information among the individuals involved in and being part of the system. Thus, the clients/patients and HCP/doctors are each enabled and motivated to contribute to the overall efficiency of the health care system of the example embodiment.

In particular, when used for managing diabetes patients, the system and method according to the example embodiment distinguish between diabetes type 1 patients and diabetes type 2 patients.

3 Detailed Description of the Application "InDiMa™ Apparatus" Example 3: Improved Risk Detection and First Management for Cardiovascular Patients (Including Multimorbidity Patients with Diabetes Through the Comprehensive Empowerment by the InDiMa™ System)

3.1 InDiMa™ Empowerment and a Collaborative Cardiovascular Risk-Patients as described in Part I and in Part II (Claims), the comprehensive BPPS approach, integrating Bio-Medical Factors (InDiMa™ "Bio-Marker"),
Psychological Factors (InDiMa™ "Psycho-Marker"),
Personal Characteristics and Traits (InDiMa™ "Perso-Marker"), and
Socio-Economic Factors (InDiMa™ "Socio-Marker")

is combined through the Neuronal Network System of the InDiMa™ Apparatus with an activation of the patient with (the innovative embodiment of) the Three Step Model:

TABLE 6

Step 1 "Self-Assessment" of the Patient
Step 2 "Reality Check" and (Lab Results) Feedback as well as Diagnosis of the Physician/Medical Experts
Step 3 "Collaborative Care": Patient and Physician cooperating in the use of the EEG (Electroencephalogram) and ECG (Electrocardiogramm)

This is creating the (innovative and significantly improved) empowerment and preparation of the patient with cardiovascular risks for a significantly improved cardiovascular risk management, using the EEC and ECG measurement ranges with the NNS (Neuronal Network System) of Prof. Reuter as risk indicator.

3.2 The Nns Apparatus for the Classification of Brain and Cardiovascular Conditions in Risk Management Patent Application in Cardiovascular Therapy for Detection of Low-Intensity Signals by NNS This installation is an entitlement (patent application) to the utilization of the procedure contained in and protected by patent DE 39 29 077 C2, the contents of which are incorporated herein by reference.

With the introduction of digital calculators that become ever smaller in size and faster it is now possible to measure, to process and to analyze in the online-modus highly complex and weak electromagnetic amplitudes. This offers the possibility to also include, to process and to analyze signals that are by their nature low-intensity biological or physiological signals of high relevance in cardiovascular therapy.

Simultaneous Classification of Brain and Heart Signals of Low Intensity

Especially the simultaneous classification and identification of brain and heart signatures is an essential parameter to monitor the vital condition of individuals under changing and life-threatening circumstances.

Today it is the state of the art to apply a standardized measurement procedure of the pulse rate by analyzing its exact frequency over time with the electrocardiogram (ECG) and the brain activity through the electromagnetic activity of its neurons via electroencephalogram (EEG): This standardized procedure is applied to classify and to identity the 'activity status' of these two organs.

Simultaneous Medical Monitoring of Pulse Rate and Brain Activity

Especially with the more and more complex medically indicated interventions relating to vital cardiovascular functions or operations caused by traumata a simultaneous combined monitoring of these two vital parameters (brain and heart) is necessary. This is the only way to realize an effective classification and identification of the activity status of this vital combination: cardiovascular system and central nervous system (CNS).

NNS—Supported Brain and Pulse Monitor

This simultaneous monitoring combined with an equally simultaneous classification/identification of brain and heart status by their activity behavior of the innervating neurons is the object of the present patent application.

The reason for this is mainly the insufficient separation of low-intensity bio-signals from the noise that is masking the low-intensity bio-signals. The low-intensity bio-signals also can be separated from frequencies of other electromagnetically active organs and in case of the brain the 'masking' of the electromagnetic signals of the lower brain structures coordinating the vitality of the individual which is caused by the large tissue mass of the neocortex.

Failure of Existing Signal Identification and Monitoring Methods

Because of these obstacles the existing signal processing, classification and identification procedures (that have been favored so far) fail an identification of low-intensity or 'masked' or screened activity centers is not possible or requires an enormous attention and routine of the respective applicant.

On the other hand many medical studies show that the pulse rate frequently is changing in the tenth or hundredth Hertz range while this pulse rate variability is equivalent to the permanent adjustment of the default offered by the brainstem. This makes the pulse rate range of minor variations the central parameter of the vitality of the cardiovascular monitoring system located in the brainstem which is always active. When it extinguishes and/or sways without adequate correction in wide ranges, this is an indicator for severe damages and/or poisonings and/or malfunctions of the Central Nervous System (CNS) which can lead to the death of an individual.

Separate Analysis of ECG and EEG

Furthermore, the latest medical analyses show that a successfully combined standardization of EEC- and ECG-values cannot be expected in the future. They have to be considered rather as highly individual and dependent upon Lifestyle and bio-medical life history. The two parameters depend for example upon age, gender, physical and mental health, diabetes and other permanent diseases affecting the metabolism. Also climate and other not mentioned parameters might have an influence.

In addition, one can see that therapeutic actions can influence the 'normal' EEC- and ECG-values of an individual which has consequences for the classification of the vital parameters.

Existing Monitoring Monitoring Results: Only a 'Rough Guideline'

The values and results shown in the literature are therefore merely a rough guideline. In addition to a constant gathering of the vital parameters heart and brain activity modern 'Analyzers' have to be subject to conditioning—thus offering individual adjustability—if one is aiming at an adequate analysis of heart and brain activity.

'Conditioning' for Exact Monitoring by NNS-Technology of InDiMa™-System

This conditioning can be realized by using neuronal networks, adaptive fuzzy-classificators or re-writeable media such as ROM, PROM, EPROM, EEPROM, in which the individual heart and brain activity pattern can be stored in form of learning patterns that are used as references for the current individual status.

All these guidelines have not been sufficiently solved by the existing 'state of the art' technology since the standard procedures separate data gathering and data analysis of EEC- and ECG-values; the values of the pulse rate are not analyzed in the tenth or hundredth Hertz range and no 'micro changes' of the individual heart and brain activity patterns are taken into consideration to classify the individual status. The InDiMa™ NNS-Classificator for 'Cardio-Vascular Risk Management'

The example embodiment described here is covering and integrating all these focal aspects since it achieves and secures the simultaneous continuous and individual gathering of heart and brain activity data, analyzed in the tenth or hundredth Hertz range and establishes a very exact categorization and identification.

In an additional Example embodiment the present installation of the InDiMa™-system allows for a readjustment of the individual heart and brain activity patterns and allows defaults that can be altered. Therefore the InDiMa™ NNS-system is individualizing the evaluation criteria for the classification/identification of the activity status of the associations of neurons that are gathered and individualized. Additionally the InDiMa™ NNS-system is tracing the status alterations that have been produced by therapeutic measures, for example.

Summary: Example Embodiment of an 'InDiMa™ Medical Risk Management Monitoring System in Cardiovascular Therapy'

All these tasks are for the first time ever solved by the characteristics of this patent claim in the presented way of the 'InDiMa™ NNS System' for 'Monitoring of High Risk Cardiovascular and Diabetes Patients'.

Many modifications and variations of the example embodiment will be apparent to those of ordinary skill in the art in light of the foregoing disclosure. Therefore, it is to be understood that, within the scope of the appended claims, the example embodiment can be practiced otherwise than has been specifically shown and described.

Figure 10:
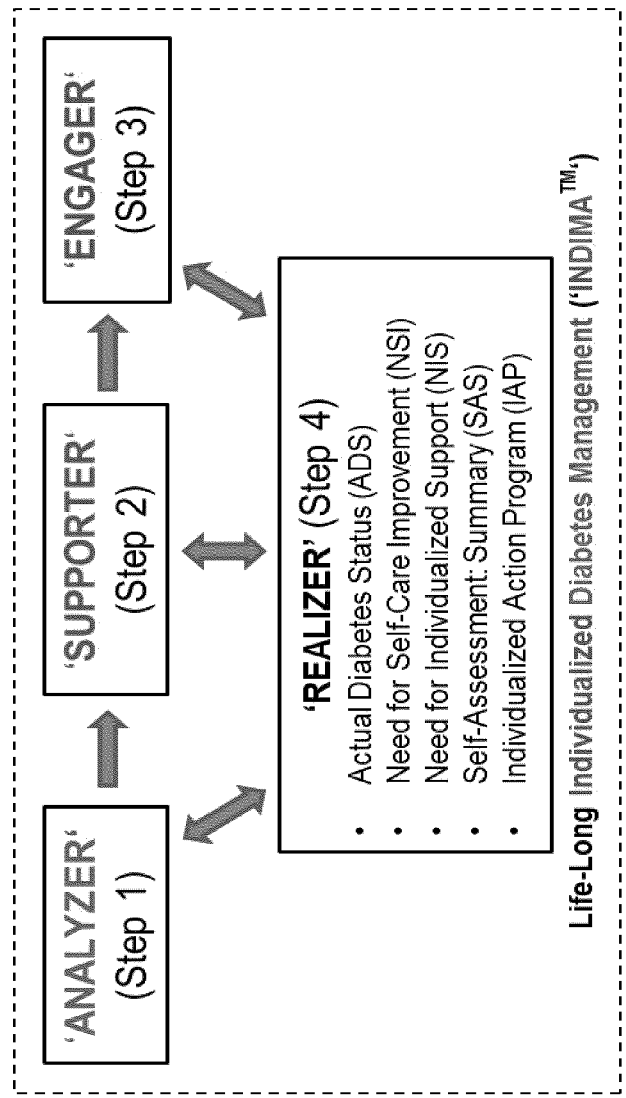
FIG. 10 is a schematic diagram of an example of four steps of the present technology model for individual diabetes management.
Figure 11:
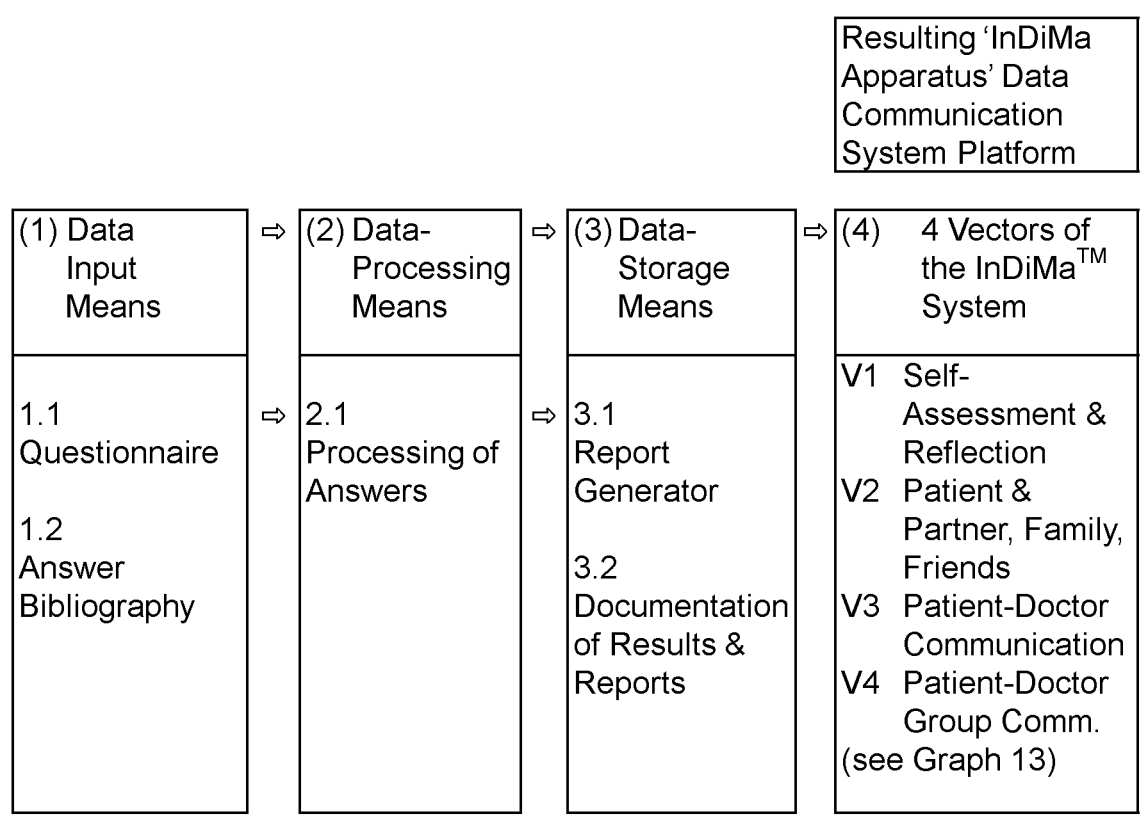
FIG. 11 is a schematic diagram of an example of the communication system and apparatus utilizable in the present technology for input, processing, storage and output.
Figure 13:
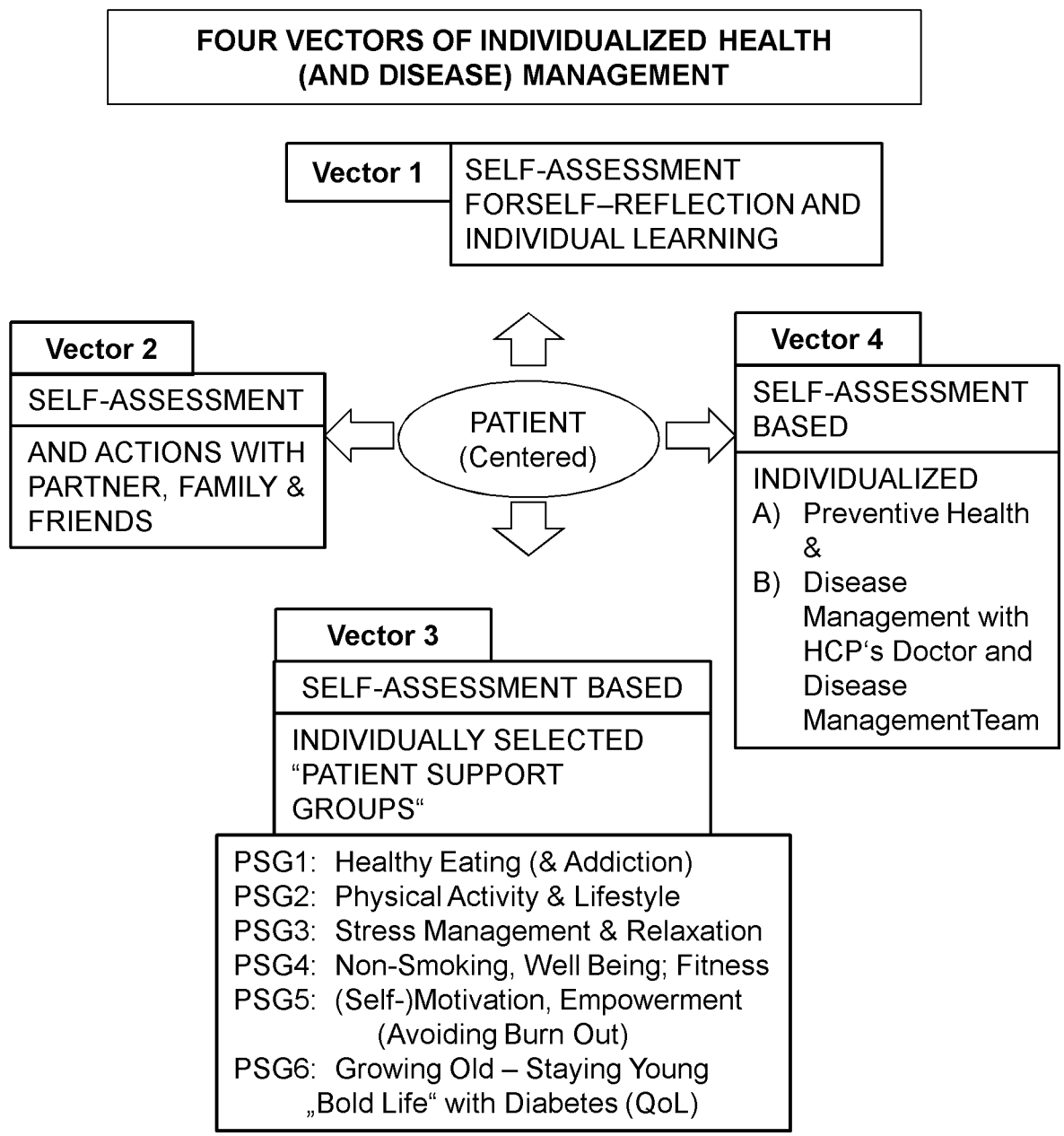
FIG. 13 is a schematic diagram of an example of four vectors individualized diabetes management and public cost transfer.
Figure 14:
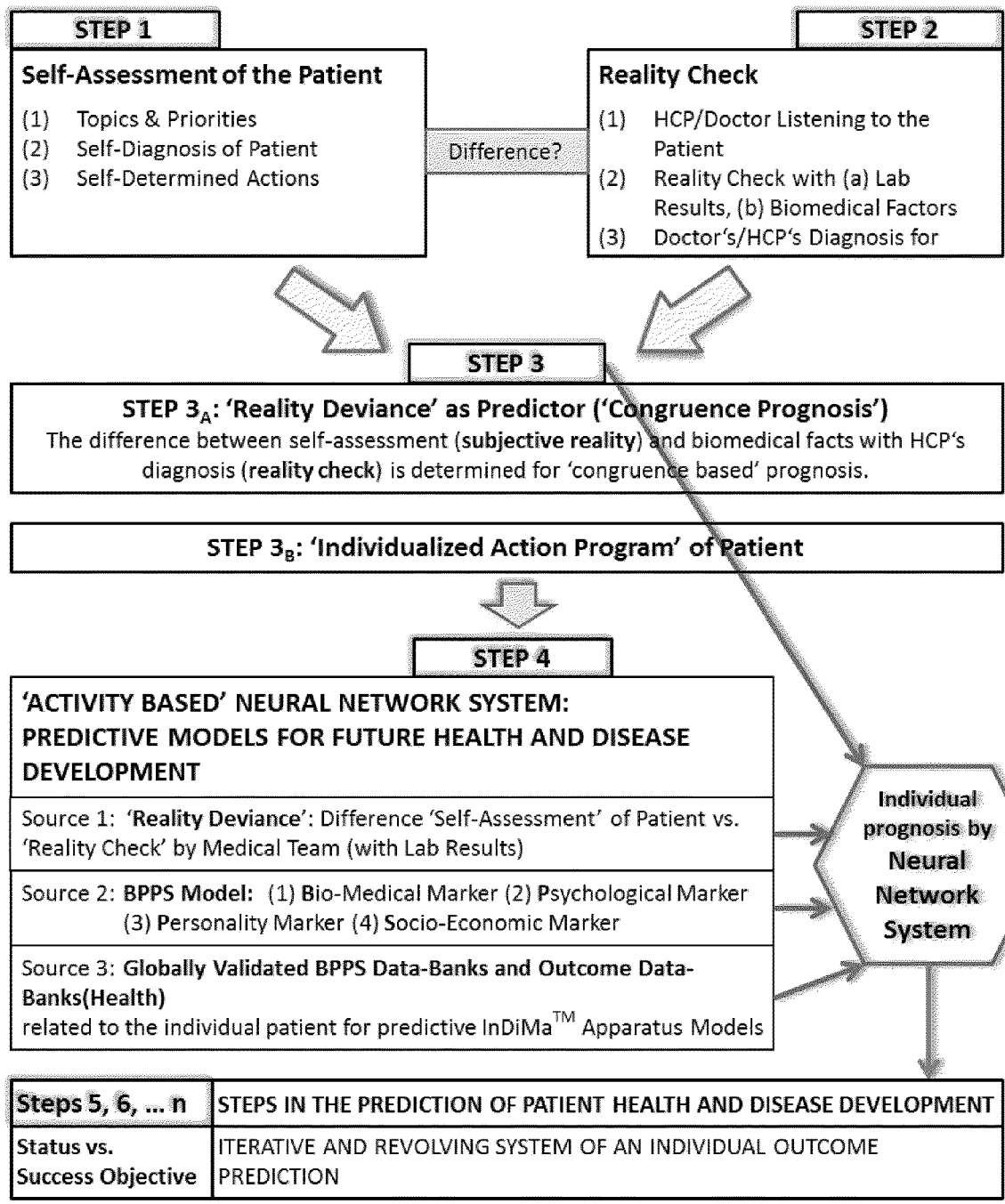
FIG. 14 is a schematic diagram of an example of predictive models of the present technology by activity-based Neural Network Systems.

All of the systems, methods, and computer programs described above and in the claims can be applied and have been applied successfully to "Individualized Health Management" or can be applied to any of the other five areas of application described in the introduction and in FIG. 10:

'IHM': 'Individualized Health Management',
'IFM': 'Individualized Finance Management',
'ISD': 'Individualized Social Development,
'IPD': 'Individualized People Management',
'ISM': 'Individualized Sales & Marketing',
'ILD': 'Individualized Lifestyle & Design'.

The invention claimed is:

1. A system for individualized and collaborative health care involving a plurality of individuals, using groups of state parameters for defining a state of each individual, and using groups of action parameters for defining treatment options, support options and/or behavior options targeted at an individual within said plurality of individuals, the system comprising:

at least one sensor configured to ascertain physiological or psychological sensor data of said targeted individual; and a computer system in communication with said sensor, said computer system comprises one or more physical processors programmed with computer program instructions which, when executed cause the computer system to:

convert said sensor data to a sensor data vector in a defined sequence;

process input data that is based on said groups of state parameters and said sensor data vector, into output data, which are the basis for said groups of action parameters, using defined relationships/assignments between groups of state parameters and groups of action parameters;

process one or more estimators based on said sensor data vector in a hierarchical manner, the estimators each represents one patient status;

store, on at least one data storage device, said groups of state parameters, said groups of action parameters and said defined relationships/assignments between groups of state parameters and groups of action parameters;

define at least one state of each of said individuals using said output data, said state of said individuals being in part defined from a social module, a personal module and a psychological module that are implemented by said computer system;

receive medical information about said individuals;

compare said state of said individuals and said medical information by determining a deviation from at least part of said state of said individuals and at least part of said medical information;

define at least one treatment or behavior option using said groups of action parameters, said action parameters being defined in part from said social module, said personal module, said psychological module, and said deviation;

target said treatment or behavior option to a targeted individual within said plurality of individuals;

generate a predicted state of health of said targeted individual at a pre-determined time period utilizing a neural chain of said estimators, and classifying said targeted individual to a category of a plurality of categories according to said predicted state, and providing said predicted state of health with said treatment or behavior option; and communicate to said targeted individual, by way of a data communication system, said treatment or behavior option, state parameters selected from said groups of state parameters and/or action parameters selected from said groups of action parameters among said plurality of individuals.

2. The system according to claim 1, wherein said computer program instructions comprises an adaptive structure where said defined relationships/assignments between groups are redefined/updated using empirical or by neural network analysis defined relations and correspondences pairs of action parameter groups and state parameter groups.

3. The system according to claim 2, wherein said adaptive structure is selected from the group consisting of expert systems, fuzzy logic, neural networks, genetic and/or evolutionary algorithms and combinations thereof.

4. The system according to any one of the preceding claims, wherein the system is web-based including one or more of PC-application, tablet application, smartphone-technology and other electronic communication devices.

5. The system according to any one of the preceding claims, wherein said groups of state parameters are selected from the group consisting of biomedical/physiological, psychological, persona and socio-economic characteristics/attributes of health care clients.

6. The system according to any one of the preceding claims, wherein a health care client-specific said state parameter group is based on observation, evaluation and assessment of said health care client using a questionnaire for said self-assessment.

7. A method for individualized and collaborative health care involving a plurality of individuals, using groups of state parameters that define a state of each individual, and using groups of action parameters that define individualized treatment options, individualized support options and/or individualized behavior options targeted at a targeted individual within said plurality of individuals, the method being implemented in a computer system that includes one or more physical processors configured to execute one or more computer program modules, the method comprising the steps of:

ascertaining physiological or psycho-medical sensor data of said targeted individual utilizing at least one sensor;

converting, using said processors, said sensor data to a sensor data vector in a defined sequence;

processing, using said processors of said computer system, input data received by said computer system and said sensor data vector, which are based on said groups of state parameters, into output data, which are the basis for said groups of action parameters, using defined relationships/assignments between groups of state parameters and groups of action parameters;

storing, on at least one data storage device of said computer system, said groups of state parameters, said groups of action parameters and said defined relationships/assignments between groups of state parameters and groups of action parameters;

defining, using said processors of said computer system, at least one state of each of said individuals using said output data, said state of said individuals being in part defined from a social module, a personal module and a psychological module;

processing, using said processors of said computer system, medical information associated with said individuals;

comparing, using said processors, said state of said individuals and said medical information by determining a deviation from at least part of said state of said individuals and at least part of said medical information;

defining, using said processors of said computer system, at least one treatment or behavior option or an individualized action program using said groups of action parameters, said action parameters being defined in part from said social module, said personal module, said psychological module, and said deviation;

processing, using said processors of said computer system, one or more estimators based on said sensor data vector in a hierarchical manner, the estimators each represents one patient status;

generate a predicted state of health of said targeted individual at a pre-determined time period utilizing a neural chain of said estimators, and classifying said targeted individual to a category of a plurality of categories according to said predicted state, and providing said predicted state of health with said treatment or behavior option or said individualized action program; and communicating to said targeted individual said treatment or behavior option using a communication interface of said computer system, state parameters selected from said groups of state parameters and/or action parameters selected from said groups of action parameters among said plurality of individuals.

8. The method according to claim 7, wherein said defined relationships/assignments between groups are redefined/updated using empirical pairs/empirically defined relations and neural networks determined relations of action parameter groups and state parameter groups.

9. The method according to claim 7 or 8, wherein said groups of state parameters are selected from the group consisting of biomedical/physiological, psychological, personal and socio-economic characteristics/attributes of health care clients.

10. The method according to any one of claims 7 through 9, wherein a health care client-specific said state parameter group is determined by assessing said health care client using a questionnaire.

11. The method according to claim 10, wherein said health care client-specific state parameter group is repeatedly determined throughout said health care client's affiliation to said plurality of individuals.

12. The method according to any one of claims 7 through 11, wherein communication and information exchange is made available: among individuals belonging to a first subset health care client (HCC), and family, friends, social environment of said plurality of individuals; among individuals belonging to a second subset health care professional (HCP) of said plurality of individuals; and between individuals belonging to said first subset (HCC) and individuals belonging to said second subset (HCP).

13. The method according to any one of claims 7 through 12, wherein defined relationships/assignments between action parameter groups and state parameter groups are made available for communication and information exchange among said plurality of individuals.

14. The method according to any one of claims 7 through 13, wherein individuals of said plurality of individuals are categorized into different categories of individuals based on their respective state parameter groups and corresponding action parameter groups.

15. The method according to claim 10, wherein said questionnaire is a web-based questionnaire sent to said targeted individual by way of said communication interface of said computer system.

16. The method according to claim 10, wherein said questionnaire is configured or configurable to provide information regarding self-assessments of a medical and physiological condition of said targeted individual, information regarding a psychological condition of said targeted individual, information regarding a personality trait, communication style, genetic factors, and/or behavior patterns of said targeted individual, and information regarding fitness, activities, and/or lifestyle of said targeted individual.

17. The method according to claim 16, wherein said treatment or behavior option or said individualized action program is at least in part dependent on said information provided by said questionnaire.

18. The method according to claim 16 further comprising the steps of:

defining at least one parameter in said group of state parameters by in part using said information from said questionnaire to assign a marker or value for said targeted individual; and creating said client-specific action parameter group where each parameter in said client-specific action parameter group is assigned a marker or value for said targeted individual.

19. The method according to claim 10 further comprises the step of creating at least one report and associating said report with said treatment or behavior option, said report being selected from the group consisting of rating said targeted individual condition associated with groups of success factors relating to at least one question in said questionnaire, supporting further detailed self-assessment of said targeted individual, and categorizing an action to be conducted by said targeted individual.

20. The method according to claim 7, wherein said medical information is associated with said targeted individual, and is provided by at least one health care professional associated with said targeted individual.

21. The method according to claim 7 further comprises the step of determining need-for-action levels and associating said need-for-action levels with said treatment or behavior option, said need-for-action levels includes a first level where said deviation is determined to be at a first predetermined value, a second level where said deviation is determined to be at a second predetermined value that is less than said first predetermined value, a third level where said deviation is determined to be a third predetermined value that is less than said second predetermined value, and a fourth level where no deviation is found.

22. The method according to claim 7 further comprises the step of receiving biomedical information using a data interface of said computer system, said data interface is configured or configurable for data acquisition, said biomedical information being selected from the group consisting of blood pressure, lipids, and blood glucose level.

23. The method according to claim 22, wherein said treatment or behavior option is at least in part dependent on said biomedical information.

24. The method according to claim 7 further comprising a neural network system to generate said predicted state of health, wherein said neural network system comprises a learning system based upon a self-organizing map constructed from a set of said action parameters, a set of predetermined action levels, and corresponding predetermined disease progression data.

25. The method according to claim 7, wherein: said social module is configured or configurable to process in part said input data with respect to a social aspect selected from the group consisting of social situation, social history, social environment, socio-economic status, social and financial status, and challenges of said individuals; said personal module is configured or configurable to process in part said input date with regard to a personality aspect selected from the group consisting of personality traits, characteristics of the person, personal life history, communication and interaction style, and preferences, customs and habits which said individuals acquired up to present day; and said psychological module is configured or configurable to process in part said input data with regards to a psychological aspect selected from the group consisting of energy level, psychological status, stress management, personal preferences, likes and dislikes.

26. The system according to claim 6, wherein said questionnaire is a web-based questionnaire sent to said targeted individual by way of a communication interface of said computer system.

27. The system according to claim 6, wherein said questionnaire is configured or configurable to provide information regarding self-assessments of a medical and physiological condition of said targeted individual, information regarding a psychological condition of said targeted individual, information regarding a personality trait, communication style, genetic factors, and/or behavior patterns of said targeted individual, and information regarding fitness, activities, and/or lifestyle of said targeted individual.

28. The system according to claim 27, wherein said treatment or behavior option is at least in part dependent on said information provided by said questionnaire.

29. The system according to claim 27, wherein said information from said questionnaire is used in part by said processor to define at least one parameter in said group of state parameters by assigning a marker or value for said targeted individual, and wherein said client-specific action parameter group is created by said processor where each parameter in said client-specific action parameter group is assigned a marker or value for said targeted individual.

30. The system according to claim 6, wherein said treatment or behavior option includes at least one report selected from the group consisting of rating said targeted individual condition associated with groups of success factors relating to at least one question in said questionnaire, supporting further detailed self-assessment of said targeted individual, and categorizing an action to be conducted by said targeted individual.

31. The system according to claim 1, wherein said medical information is associated with said targeted individual, and is provided by at least one health care professional associated with said targeted individual.

32. The system according to claim 1, wherein said treatment or behavior option further includes need-for-action levels selected from the group consisting of a first level where said deviation is determined to be at a first predetermined value, a second level where said deviation is determined to be at a second predetermined value that is less than said first predetermined value, a third level where said deviation is determined to be a third predetermined value that is less than said second predetermined value, and a fourth level where no deviation is found.

33. The system according to claim 1, wherein said computer system further includes a data interface for data acquisition, said data interface is configured or configurable to receive biomedical information selected from the group consisting of blood pressure, lipids, and blood glucose level.

34. The system according to claim 33, wherein said treatment or behavior option is at least in part dependent on said biomedical information.

35. The system according to claim 1 further comprising a neural network system to generate said predicted state of health, wherein said neural network system comprises a self-organizing map constructed from a set of said action parameters, a set of predetermined action levels, and corresponding predetermined disease progression data.

36. The system according to claim 1, wherein: said social module is configured or configurable to process in part said input data with respect to a social aspect selected from the group consisting of social situation, social history, social environment, socio-economic status, social and financial status, and challenges of said individuals; said personal module is configured or configurable to process in part said input date with regard to a personality aspect selected from the group consisting of personality traits, characteristics of the person, personal life history, communication and interaction style, and preferences, customs and habits which said individuals acquired up to present day; and said psychological module is configured or configurable to process in part said input data with regards to a psychological aspect selected from the group consisting of energy level, psychological status, stress management, personal preferences, likes and dislikes.

37. The system according to claim 1, wherein said estimators are coded to be placed on a topologically closed, two-dimensional surface on a regular or irregular grid formed of said estimators configured to assign capable of assigning a same number of adjacent estimators to every said estimator.

38. The method according to claim 7 further comprises the step of coding said estimators and placing said coded estimators on a topologically closed, two-dimensional surface on a regular or irregular grid formed of said estimators, and assigning a same number of adjacent estimators to every said estimator.

* * * * *